United States Patent
Cabiri et al.

(10) Patent No.: US 12,138,168 B2
(45) Date of Patent: Nov. 12, 2024

(54) ADJUSTABLE ANNULOPLASTY DEVICES AND ADJUSTMENT MECHANISMS THEREFOR

(71) Applicant: Edwards Lifesciences Innovation (Israel) Ltd., Caesarea (IL)

(72) Inventors: Oz Cabiri, Hod Hasharon (IL); Tal Sheps, Givat Shmuel (IL); Meir Kutzik, Kfar Saba (IL); Amir Gross, Tel Aviv-Jaffa (IL); Yuval Zipory, Modi'in (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 879 days.

(21) Appl. No.: 17/112,283

(22) Filed: Dec. 4, 2020

(65) Prior Publication Data
US 2021/0085464 A1    Mar. 25, 2021

Related U.S. Application Data

(63) Continuation of application No. 15/642,861, filed on Jul. 6, 2017, now Pat. No. 10,856,986, which is a
(Continued)

(51) Int. Cl.
*A61F 2/24* (2006.01)
*A61B 17/00* (2006.01)
(Continued)

(52) U.S. Cl.
CPC .......... *A61F 2/2466* (2013.01); *A61F 2/2442* (2013.01); *A61F 2/2445* (2013.01);
(Continued)

(58) Field of Classification Search
CPC ........ A61F 2/2442–2448; A61F 2/2466; A61F 2250/001; A61F 2250/0004; A61F 2250/0007; A61F 2250/0018
See application file for complete search history.

(56) References Cited

U.S. PATENT DOCUMENTS 3,604,488 A    9/1971  Wishart et al.
3,656,185 A    4/1972  Carpentier
(Continued)

FOREIGN PATENT DOCUMENTS

CN    113331995 A    9/2021
EP    1034753 A1    9/2000
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — William H Matthews
(74) *Attorney, Agent, or Firm* — Thomas C. Richardson

(57) ABSTRACT

An annuloplasty implant comprises a flexible member, helical anchors, and non-compressible portions. The helical anchors are configured to anchor the flexible member at least partway around the valve by being screwed into tissue of the heart of a subject. Each of the non-compressible portions comprises a helical coil having a plurality of turns, and at rest has a helix pitch that contacts each turn of the coil with an adjacent turn of the coil. The flexible member extends through the non-compressible portions. The implant is configured such that applying tension to the flexible member from one end thereof contracts the implant, thereby drawing the anchors closer to each other, the helical coil of each of the non-compressible portions inhibiting contraction of the implant at the non-compressible portion.

19 Claims, 28 Drawing Sheets

Related U.S. Application Data continuation of application No. 14/567,472, filed on Dec. 11, 2014, now Pat. No. 9,713,530, which is a continuation of application No. 13/141,606, filed as application No. PCT/IL2009/001209 on Dec. 22, 2009, now Pat. No. 8,926,696, which is a continuation-in-part of application No. 12/435,291, filed on May 4, 2009, now Pat. No. 8,147,542, and a continuation-in-part of application No. 12/341,960, filed on Dec. 22, 2008, now Pat. No. 8,241,351.

(60) Provisional application No. 61/283,445, filed on Dec. 2, 2009.

(51) Int. Cl.
*A61B 17/04* (2006.01)
*A61B 17/064* (2006.01)
*A61B 17/12* (2006.01)

(52) U.S. Cl.
CPC . *A61B 2017/00243* (2013.01); *A61B 17/0401* (2013.01); *A61B 2017/0409* (2013.01); *A61B 2017/0414* (2013.01); *A61B 2017/0441* (2013.01); *A61B 2017/0464* (2013.01); *A61B 2017/0496* (2013.01); *A61B 2017/0649* (2013.01); *A61B 2017/12095* (2013.01); *A61F 2250/0004* (2013.01); *A61F 2250/001* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,501,683 A | 3/1996 | Trott |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavonik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,782,862 A | 7/1998 | Bonutti |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |

(56) References Cited

U.S. PATENT DOCUMENTS

| | | |
|---|---|---|
| 6,592,619 B2 | 7/2003 | Melvin |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,988,982 B2 | 1/2006 | Melvin et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,089 B2 | 2/2009 | Lau et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,601,117 B2 | 10/2009 | Kute et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojelbane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |

(56) References Cited

U.S. PATENT DOCUMENTS

| | | |
|---|---|---|
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Herniund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,724,084 B2 | 8/2017 | Groothuis et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 9,937,042 B2 | 4/2018 | Cabiri et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0095139 A1 | 7/2002 | Keogh et al. |
| 2002/0103532 A1 | 8/2002 | Langberg et al. |

(56) References Cited

U.S. PATENT DOCUMENTS

| | | |
|---|---|---|
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0208208 A1 | 11/2003 | Chu |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0193193 A1 | 9/2004 | Laufer et al. |
| 2004/0220593 A1 | 11/2004 | Greenhalgh |
| 2004/0236419 A1* | 11/2004 | Milo .................. A61B 17/0644 606/155 |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0187613 A1 | 8/2005 | Bolduc et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0245821 A1 | 11/2005 | Govari et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0173251 A1 | 8/2006 | Govari et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |

(56) References Cited

U.S. PATENT DOCUMENTS

| | | |
|---|---|---|
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1* | 10/2007 | Rafiee ............... A61F 2/2466 623/2.37 |
| 2007/0255397 A1 | 11/2007 | Ryan et al. |
| 2007/0255400 A1 | 11/2007 | Parravicini et al. |
| 2007/0265491 A1 | 11/2007 | Krag et al. |
| 2007/0270679 A1 | 11/2007 | Nguyen et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0082132 A1 | 4/2008 | Annest et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0208328 A1 | 8/2008 | Antocci et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissi |
| 2009/0177266 A1 | 7/2009 | Powell et al. |
| 2009/0177274 A1 | 7/2009 | Scorsin et al. |
| 2009/0187216 A1 | 7/2009 | Schmieding et al. |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0049313 A1 | 2/2010 | Alon et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0161047 A1 | 6/2010 | Cabiri |
| 2010/0168827 A1 | 7/2010 | Schultz |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1 | 11/2010 | Zipory et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |

(56) References Cited

U.S. PATENT DOCUMENTS

| | | |
|---|---|---|
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0022557 A1 | 1/2012 | Cabiri et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351906 A1 | 12/2015 | Hammer et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1 | 9/2016 | Zipory et al. |
| 2016/0302917 A1 | 10/2016 | Schewel |
| 2016/0317301 A1 | 11/2016 | Quadri et al. |
| 2016/0317302 A1 | 11/2016 | Madjarov et al. |
| 2016/0346084 A1 | 12/2016 | Taylor et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2017/0325959 A1 | 11/2017 | Sheps et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |

(56) References Cited

U.S. PATENT DOCUMENTS

| | | | |
|---|---|---|---|
| 2019/0117400 | A1 | 4/2019 | Medema et al. |
| 2019/0125325 | A1 | 5/2019 | Sheps et al. |
| 2019/0151093 | A1 | 5/2019 | Keldar et al. |
| 2019/0159898 | A1 | 5/2019 | Kutzik et al. |
| 2019/0175344 | A1 | 6/2019 | Khairkhahan |
| 2019/0175345 | A1 | 6/2019 | Schaffner et al. |
| 2019/0175346 | A1 | 6/2019 | Schaffner et al. |
| 2019/0183648 | A1 | 6/2019 | Trapp et al. |
| 2019/0240023 | A1 | 8/2019 | Spence et al. |
| 2019/0290260 | A1 | 9/2019 | Caffes et al. |
| 2019/0290431 | A1 | 9/2019 | Genovese et al. |
| 2019/0321049 | A1 | 10/2019 | Herman et al. |
| 2019/0336288 | A1 | 11/2019 | Gross et al. |
| 2019/0343633 | A1 | 11/2019 | Garvin et al. |
| 2020/0015971 | A1 | 1/2020 | Brauon et al. |
| 2020/0289267 | A1 | 9/2020 | Peleg et al. |
| 2020/0337840 | A1 | 10/2020 | Reich |
| 2021/0015475 | A1 | 1/2021 | Lau |
| 2021/0052387 | A1 | 2/2021 | Greenan et al. |
| 2021/0059820 | A1 | 3/2021 | Clark et al. |
| 2021/0085461 | A1 | 3/2021 | Neumark et al. |
| 2021/0093453 | A1 | 4/2021 | Peleg et al. |
| 2021/0145584 | A1 | 5/2021 | Kasher et al. |
| 2022/0071620 | A1 | 3/2022 | Brauon et al. |
| 2022/0096232 | A1 | 3/2022 | Skaro et al. |
| 2022/0142779 | A1 | 5/2022 | Sharon |
| 2022/0176076 | A1 | 6/2022 | Keidar |
| 2022/0233316 | A1 | 7/2022 | Sheps et al. |
| 2022/0273436 | A1 | 9/2022 | Aviv et al. |
| 2022/0313438 | A1 | 10/2022 | Chappel-Ram |
| 2022/0323221 | A1 | 10/2022 | Sharon et al. |
| 2023/0016867 | A1 | 1/2023 | Tennenbaum |
| 2023/0218291 | A1 | 7/2023 | Zarbatany et al. |

FOREIGN PATENT DOCUMENTS

| | | | |
|---|---|---|---|
| EP | 3531975 | A1 | 9/2019 |
| WO | 9205093 | A1 | 4/1992 |
| WO | 9846149 | A1 | 10/1998 |
| WO | 02085250 | A3 | 2/2003 |
| WO | 03047467 | A1 | 6/2003 |
| WO | 2007098512 | A1 | 9/2007 |
| WO | 2010000454 | A1 | 1/2010 |
| WO | 2012176195 | A3 | 3/2013 |
| WO | 2014064964 | A1 | 5/2014 |
| WO | 2019145941 | A1 | 8/2019 |
| WO | 2019145947 | A1 | 8/2019 |
| WO | 2019182645 | A1 | 9/2019 |
| WO | 2019224814 | A1 | 11/2019 |
| WO | 2020240282 | A2 | 12/2020 |
| WO | 2021014440 | A2 | 1/2021 |
| WO | 2021038559 | A1 | 3/2021 |
| WO | 2021038560 | A1 | 3/2021 |
| WO | 2022064401 | A2 | 3/2022 |
| WO | 2022090907 | A1 | 5/2022 |
| WO | 2022101817 | A2 | 5/2022 |
| WO | 2022153131 | A1 | 7/2022 |
| WO | 2022157592 | A1 | 7/2022 |
| WO | 2022172108 | A1 | 8/2022 |
| WO | 2022172149 | A1 | 8/2022 |
| WO | 2022200972 | A1 | 9/2022 |
| WO | 2022224071 | A1 | 10/2022 |
| WO | 2022229815 | A1 | 11/2022 |
| WO | 2022250983 | A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al. "Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischernic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

Odell JA et al., "Early Results o4yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology. 15(5), pp. 389-391.

Swenson, Orvar, "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

* cited by examiner

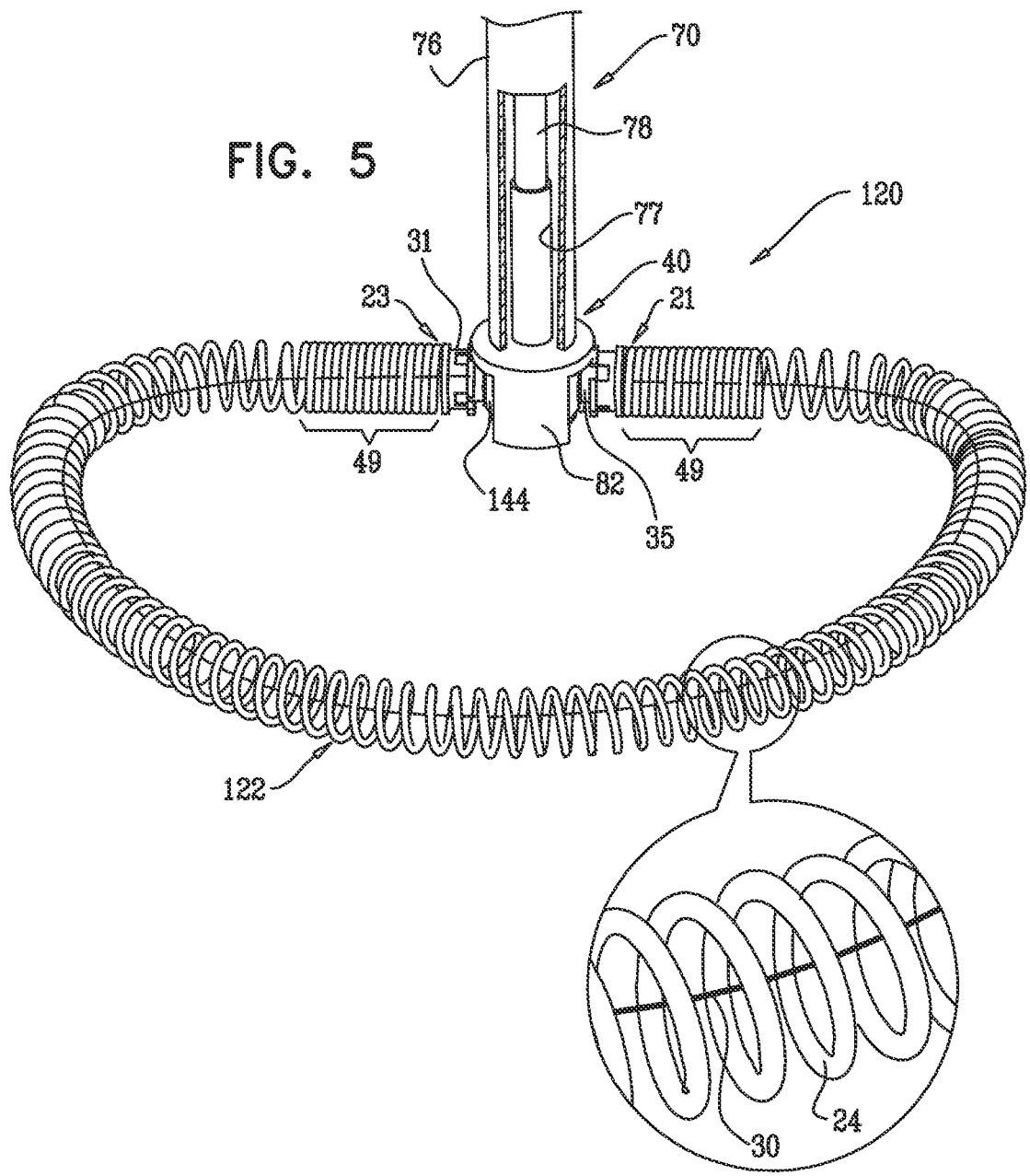

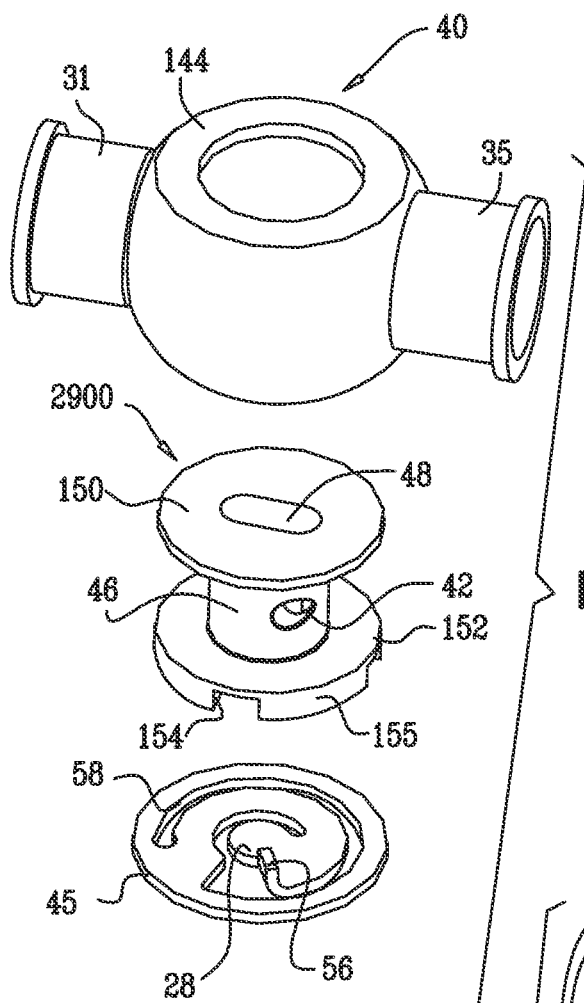
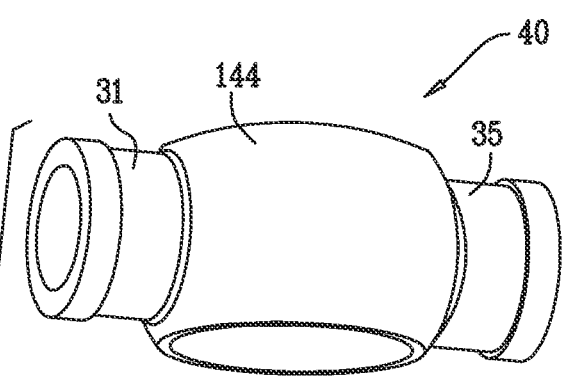
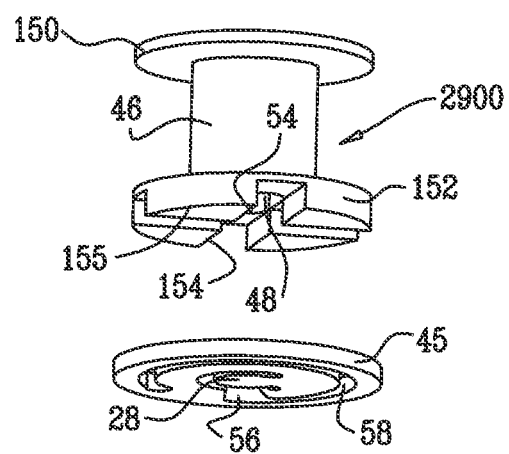
FIG. 6A
FIG. 6B

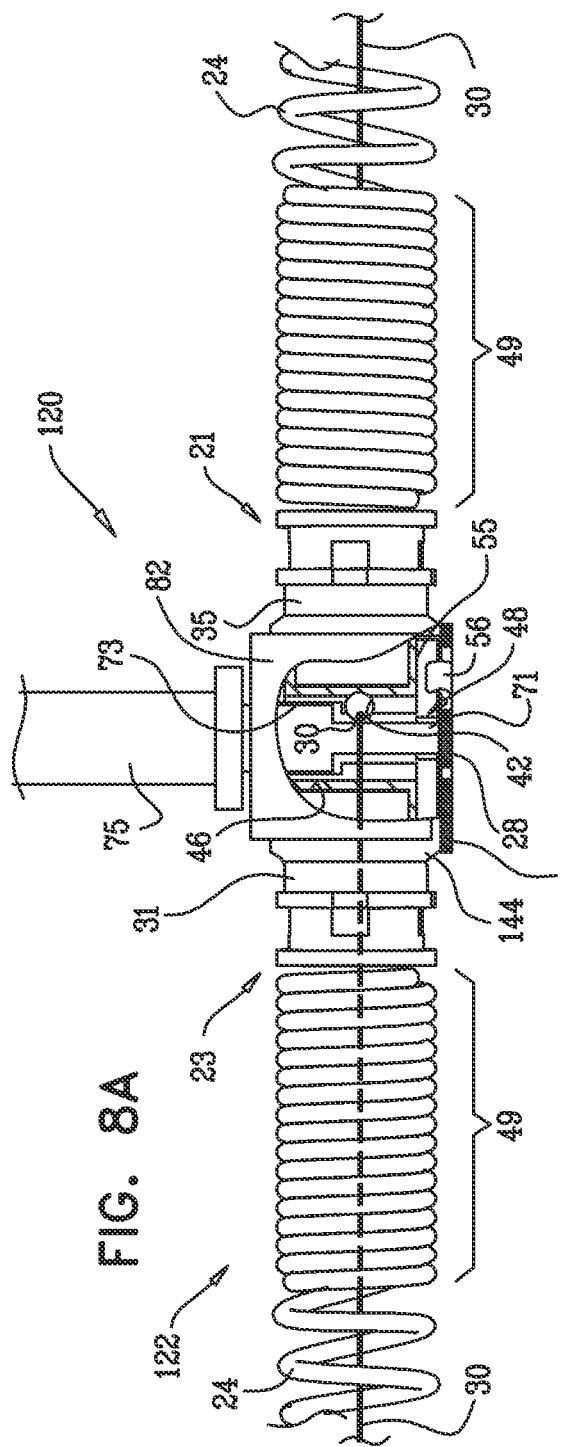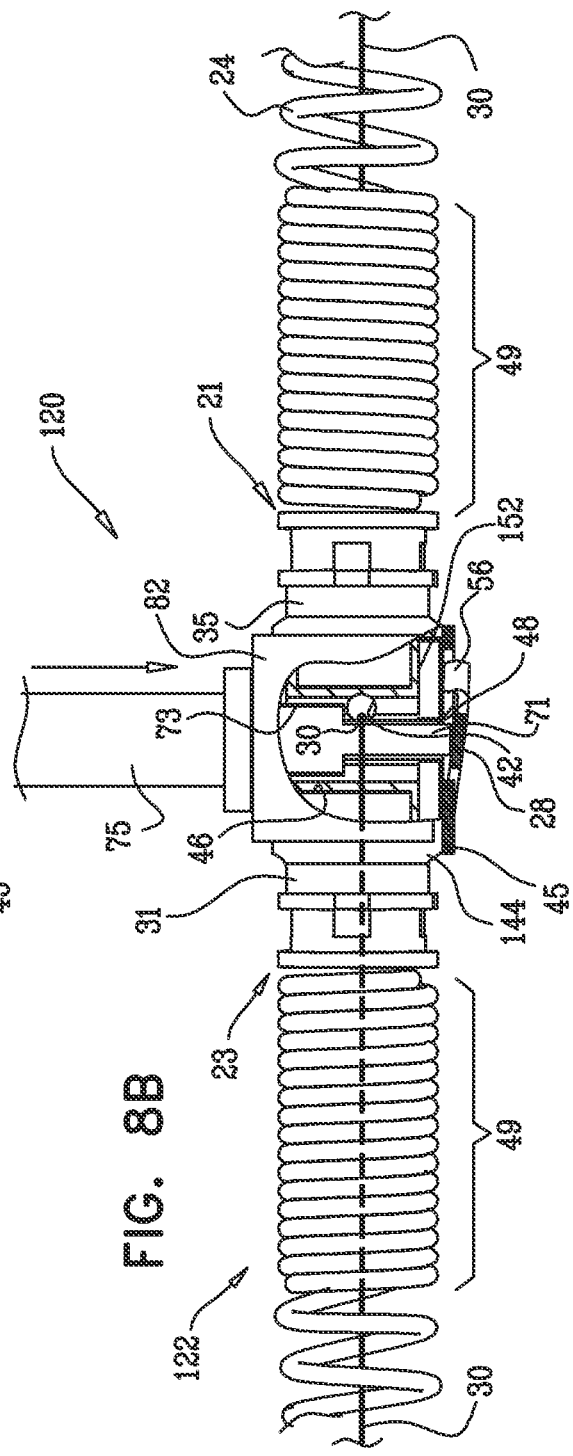

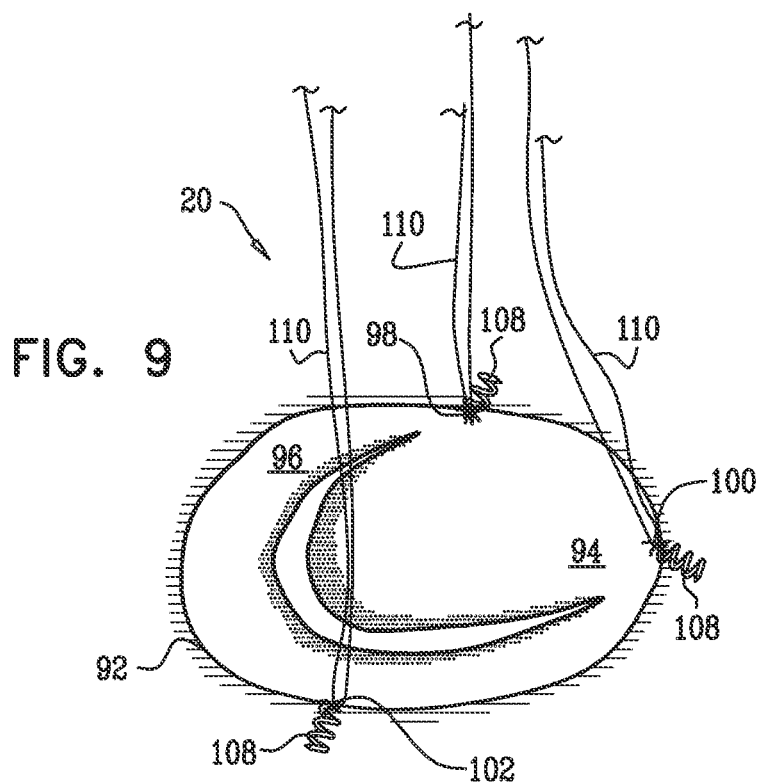

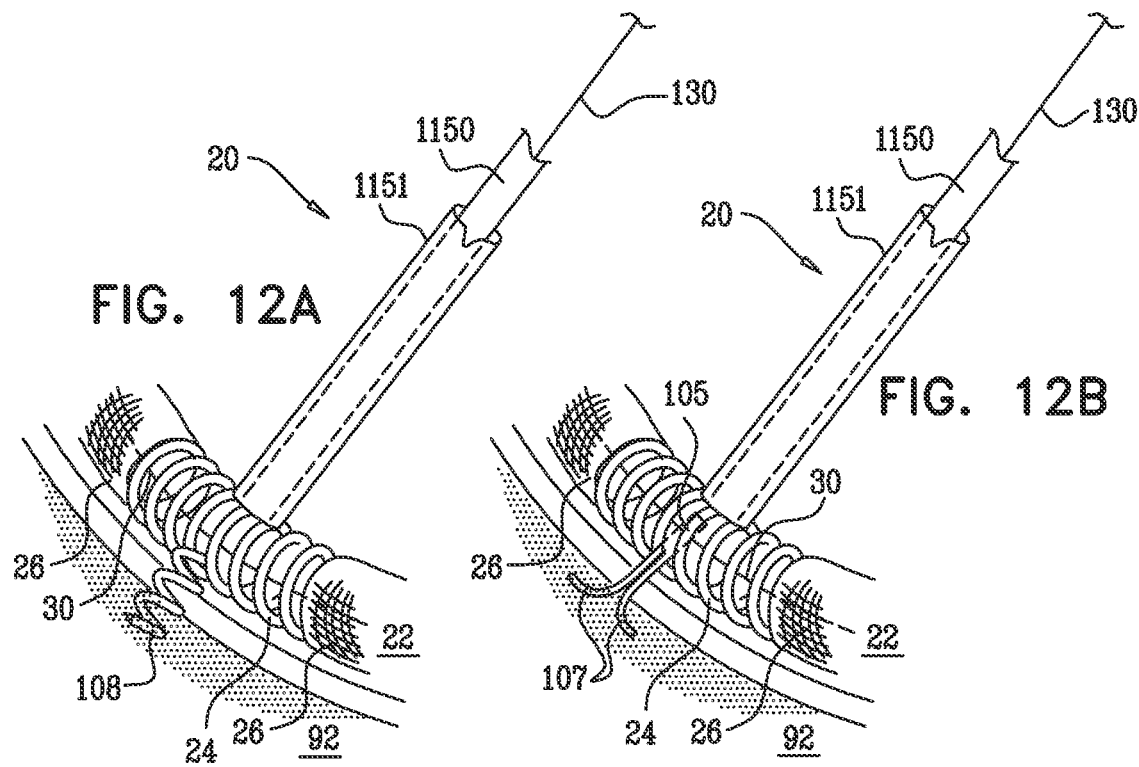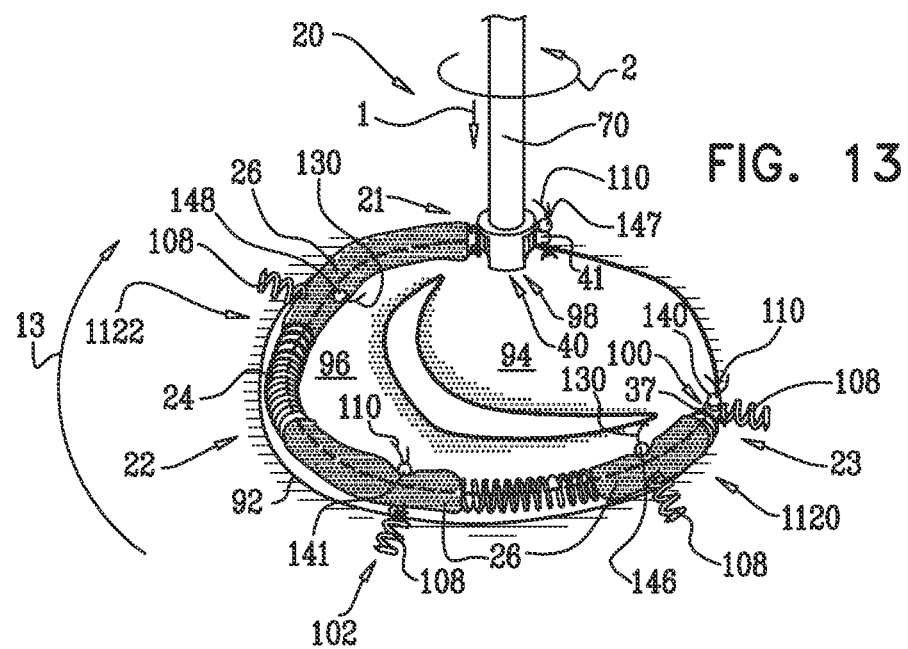

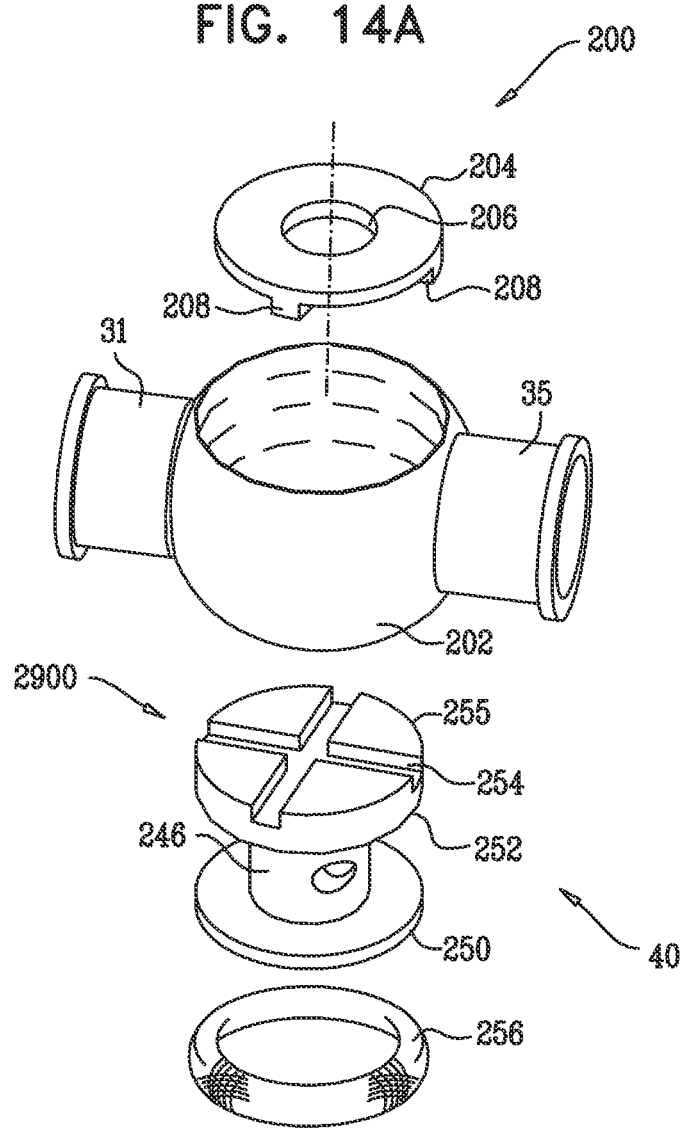

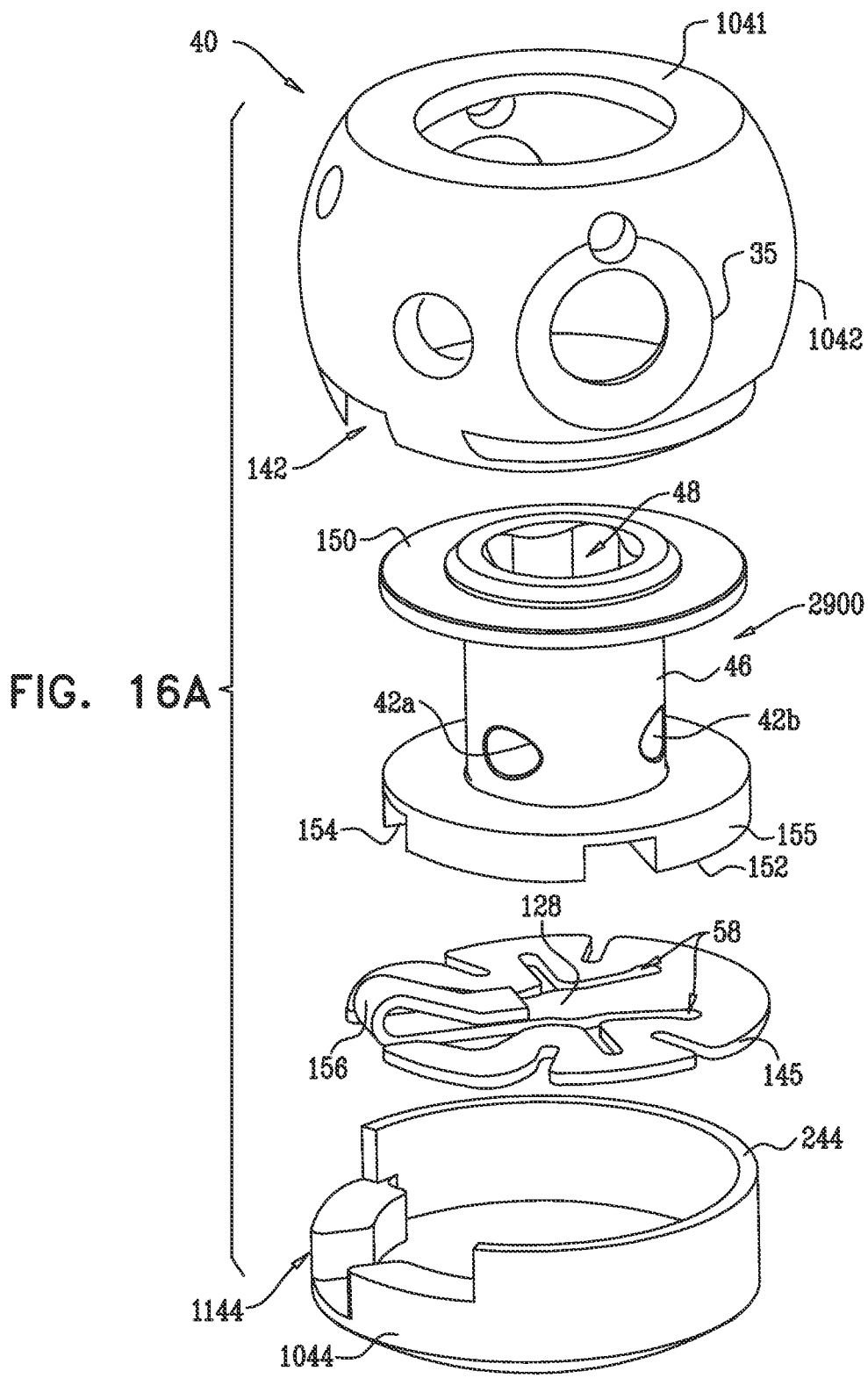

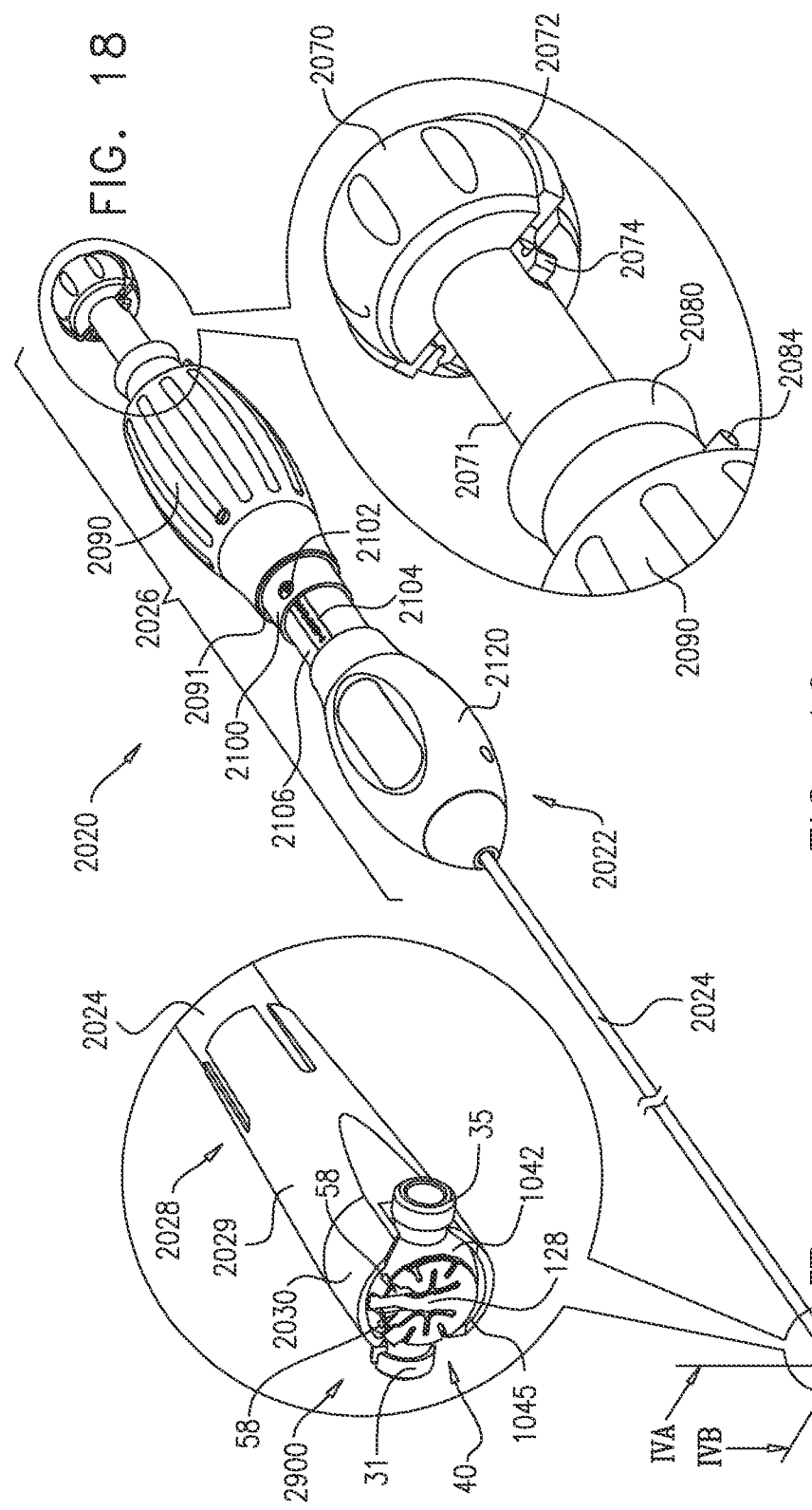
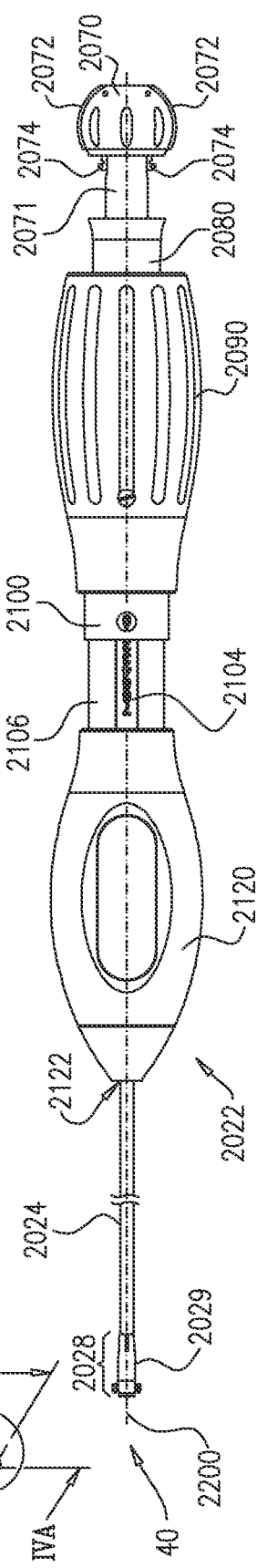
FIG. 18
FIG. 19

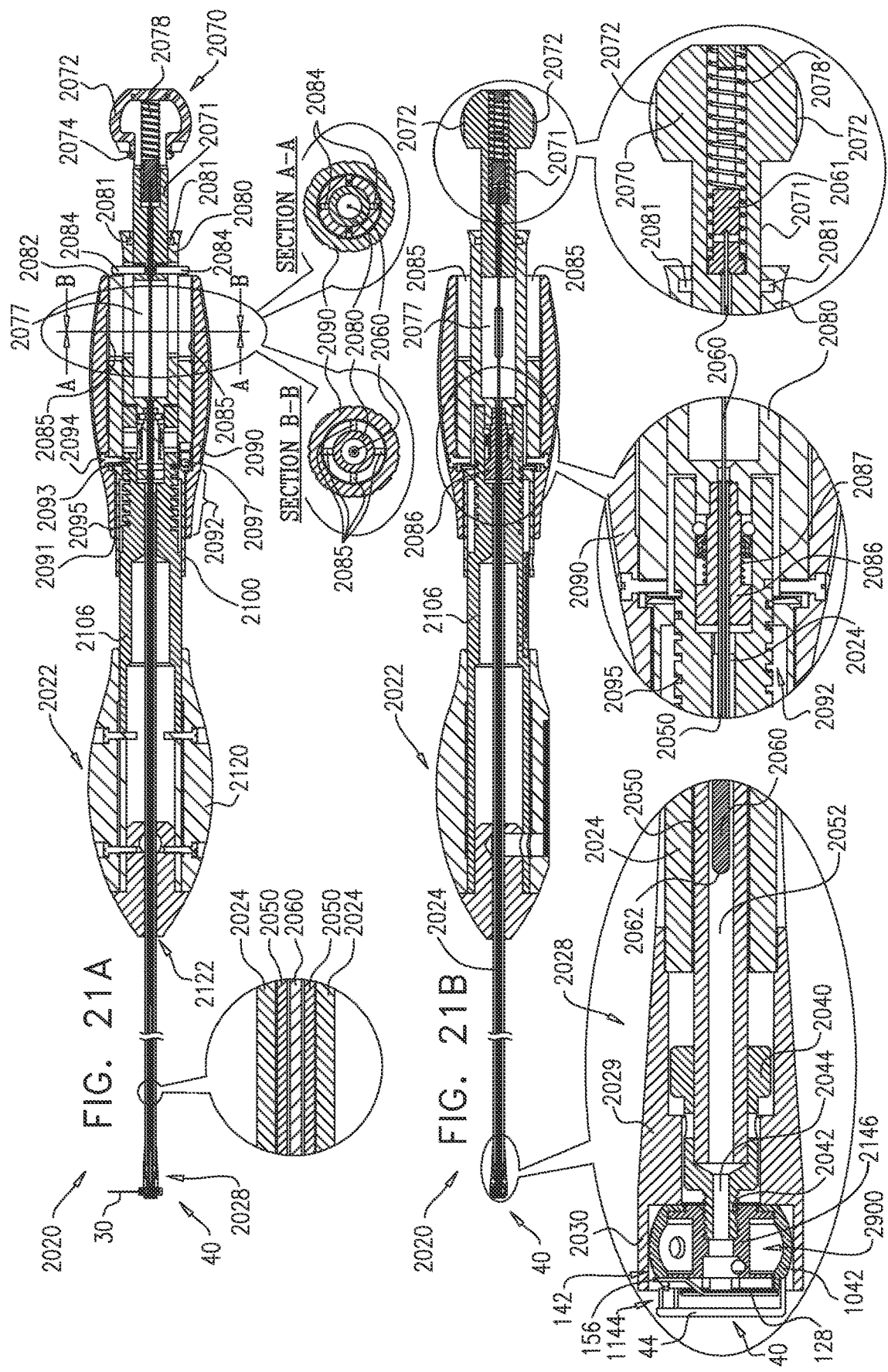

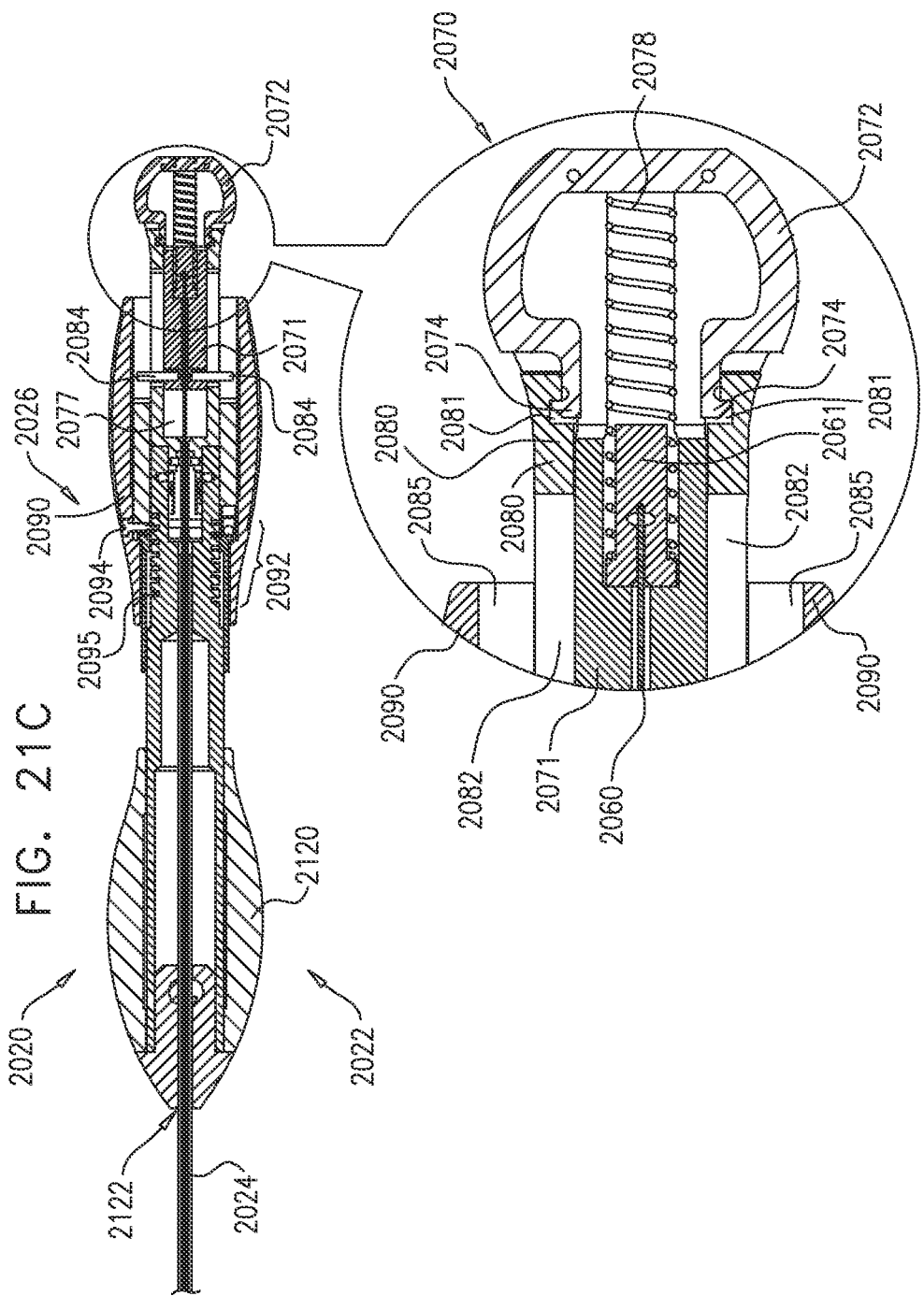

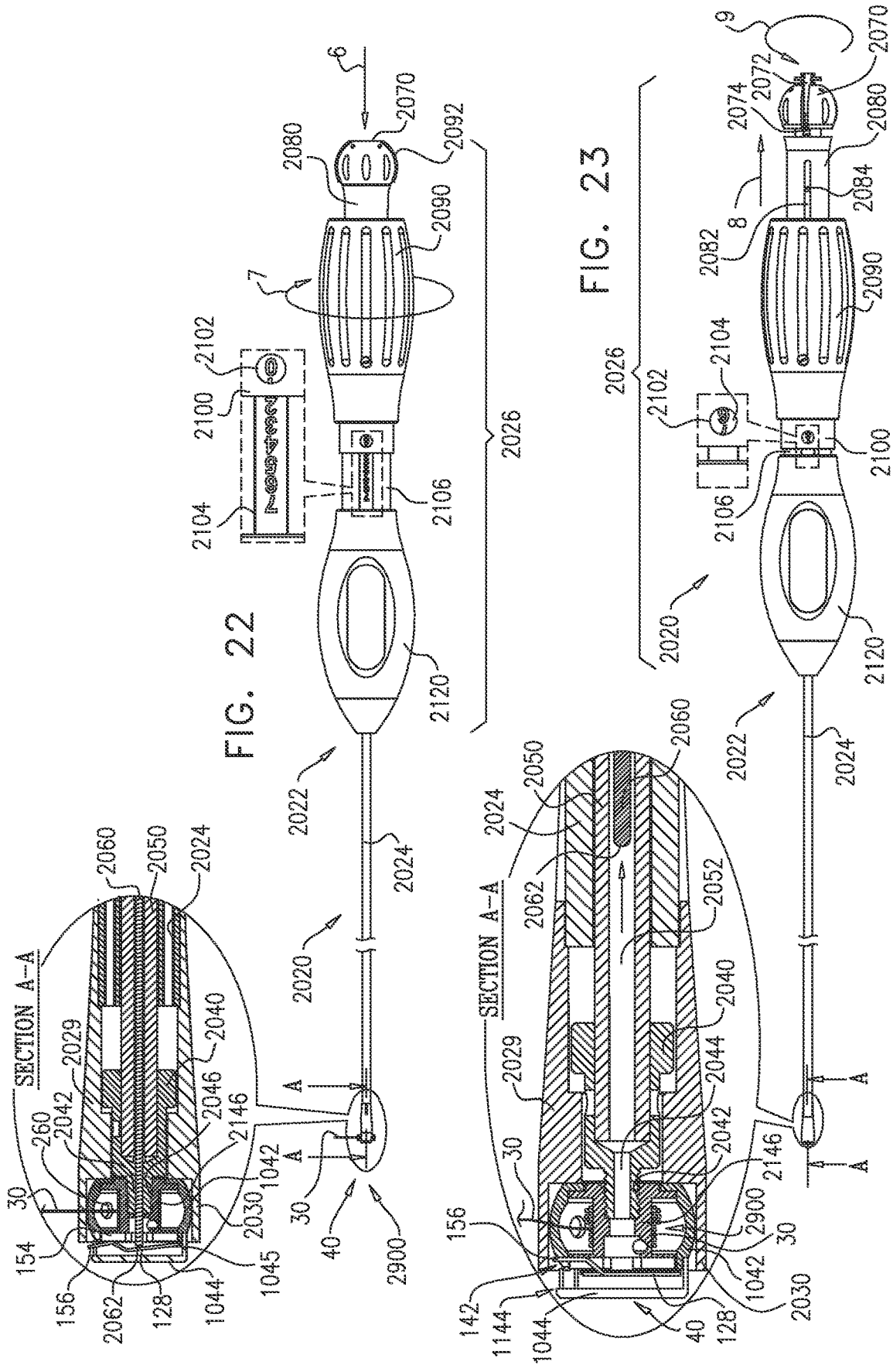

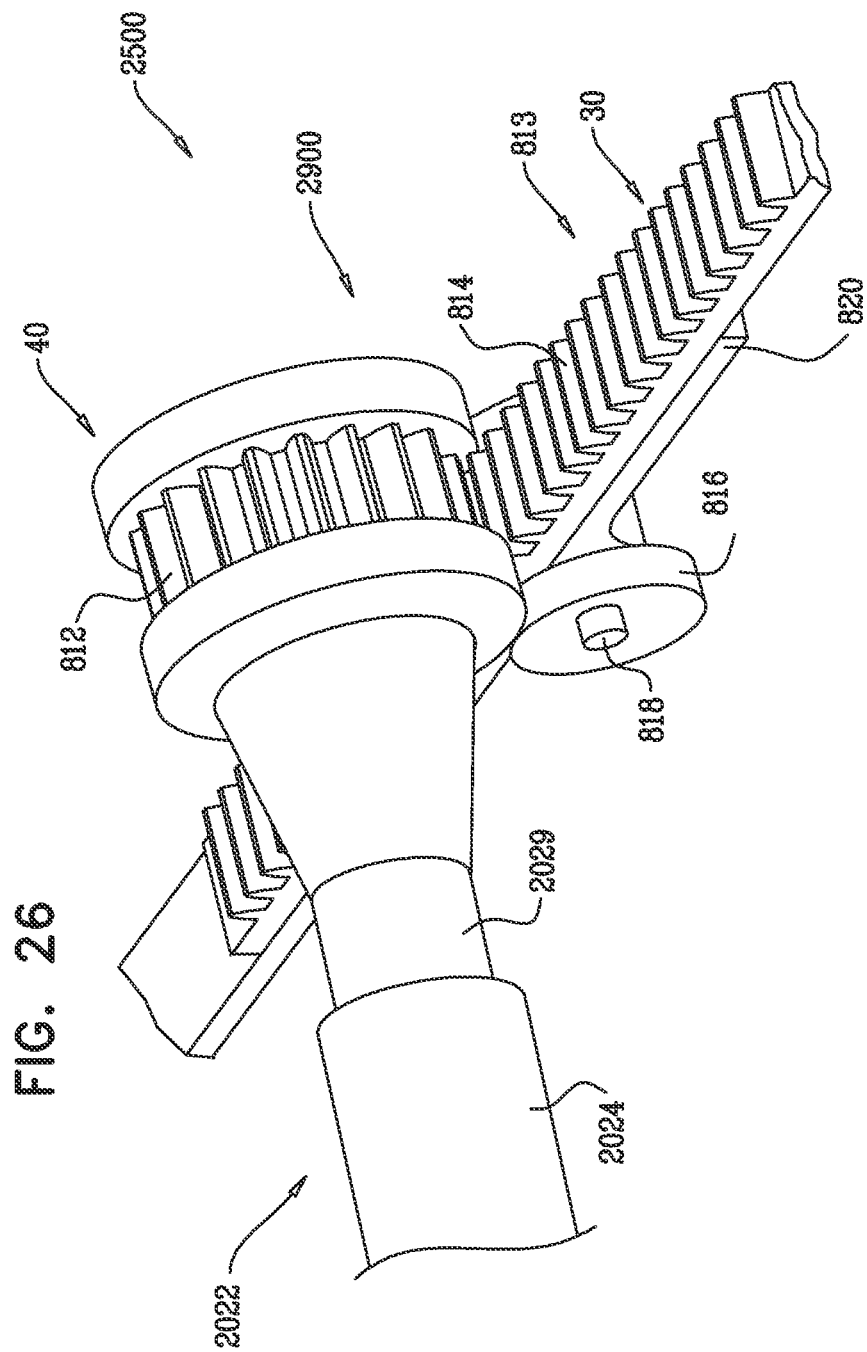

ADJUSTABLE ANNULOPLASTY DEVICES AND ADJUSTMENT MECHANISMS THEREFOR

CROSS-REFERENCES TO RELATED APPLICATIONS

The present application is a continuation of U.S. patent application Ser. No. 15/642,861 to Cabiri et al., filed Jul. 6, 2017, and entitled "Adjustable annuloplasty devices and adjustment mechanisms therefor," which published as US 2017/0367825; which is a continuation of U.S. patent application Ser. No. 14/567,472, filed on Dec. 11, 2014, and entitled "Adjustable annuloplasty devices and adjustment mechanisms therefor," (now U.S. Pat. No. 9,713,530); which is a continuation of U.S. patent application Ser. No. 13/141,606, filed on Aug. 1, 2011, and entitled "Adjustable annuloplasty devices and adjustment mechanisms therefor," (now U.S. Pat. No. 8,926,696); which is a US national phase of PCT Patent Application PCT/IL2009/001209 filed on Dec. 22, 2009, which published as WO 2010/073246, and which:
(a) is a continuation-in-part of and claims the priority from U.S. patent application Ser. No. 12/341,960 to Cabiri, entitled "Adjustable partial annuloplasty ring and mechanism therefor," filed Dec. 22, 2008 (now U.S. Pat. No. 8,241,351);
(b) is a continuation-in-part of and claims the priority from U.S. patent application Ser. No. 12/435,291 to Maisano et al., entitled "Adjustable repair chords and spool mechanism therefor," filed on May 4, 2009 (now U.S. Pat. No. 8,147,542);
(c) claims the priority from U.S. Provisional Patent Application 61/283,445 to Sheps et al., entitled "Delivery tool for rotation of spool and adjustment of annuloplasty device," filed Dec. 2, 2009; and
(d) is related to:
  (1) PCT Publication WO 06/097931 to Gross et al., entitled "Mitral Valve treatment techniques," filed Mar. 15, 2006;
  (2) U.S. patent application Ser. No. 12/548,991 to Maisano et al., entitled "Implantation of repair chords in the heart," filed on Aug. 27, 2009 (now U.S. Pat. No. 8,808,368); and
  (3) U.S. Provisional Patent Application 61/265,936 to Miller et al., entitled "Delivery tool for implantation of spool assembly coupled to a helical anchor," filed on Dec. 2, 2009.

Each of the above applications is incorporated herein by reference.

FIELD OF THE INVENTION

Some applications of the present invention relate in general to valve repair. More specifically, some applications of the present invention relate to repair of a mitral valve of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

U.S. Pat. No. 7,431,692 to Zollinger et al. describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

US Patent Application Publication 2007/0016287 to Cartledge et al. describes an implantable device for controlling shape and/or size of an anatomical structure or lumen. The implantable device has an adjustable member configured to adjust the dimensions of the implantable device. The implantable device is housed in a catheter and insertable from a minimally invasive surgical entry. An adjustment tool actuates the adjustable member and provide for adjustment before, during or after the anatomical structure or lumen resumes near normal to normal physiologic function.

US Patent Application Publication 2004/0236419 to Milo describes methods for reconfiguring an atrioventricular heart valve that may use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various ones of these systems are described as being implanted non-invasively using a delivery catheter.

US Patent Application Publication 2005/0171601 to Cosgrove et al. describes an annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring is especially suited for minimally-invasive surgeries in which the combination is delivered to an implantation site through a small access incision with or without a cannula, or through a catheter passed though the patient's vasculature.

The following patents and patent application publications, relevant portions of which are incorporated herein by reference, may be of interest:

PCT Patent Application Publication WO 07/136783 to Cartledge et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,626,930 to Allen et al.
U.S. Pat. No. 6,629,534 to St. Goar et al.
U.S. Pat. No. 6,752,813 to Goldfarb et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
US Patent Application Publication 2003/0050693 to Quijano et al
US Patent Application Publication 2003/0105519 to Fasol et al.
US Patent Application Publication 2003/0167062 to Gambale et al.
US Patent Application Publication 2004/0024451 to Johnson et al.
US Patent Application Publication 2004/0122514 to Fogarty et al.
US Patent Application Publication 2004/0148021 to Cartledge et al.
US Patent Application Publication 2004/0236419 to Milo
US Patent Application Publication 2005/0171601 to Cosgrove et al.
US Patent Application Publication 2005/0216039 to Lederman
US Patent Application Publication 2005/0288781 to Moaddeb et al.
US Patent Application Publication 2007/0080188 to Spence et al.
US Patent Application Publication 2007/0118151 to Davidson
US Patent Application Publication 2007/0162111 to Fukamachi et al.
US Patent Application Publication 2009/0177266 to Powell et al.
US Patent Application Publication 2007/0255400 to Parravicini et al.
US Patent Application Publication 2008/0004697 to Lichtenstein et al.

The following articles, which are incorporated herein by reference, may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

SUMMARY OF EMBODIMENTS

In some applications of the present invention, apparatus is provided comprising an adjustable annuloplasty structure configured to repair a dilated mitral valve of a patient. At least a portion of the annuloplasty structure comprises a flexible, longitudinally-compressible segment (e.g., coiled structures, stent-like struts, or a braided mesh). The annuloplasty structure is shaped to define a lumen thereof that houses a flexible member, e.g., a contracting wire. The annuloplasty structure comprises a contracting mechanism which facilitates contracting of the annuloplasty structure. The contracting mechanism comprises a spool to which a first end of the flexible member is coupled. Typically, a second end of the flexible member is not coupled to the spool, but rather is coupled to a portion of the annuloplasty structure.

In some applications of the present invention, the annuloplasty structure is shaped to provide an adjustable partial annuloplasty structure. In these applications, the annuloplasty structure comprises an elongate structure which is coupled at a first end thereof to the contracting mechanism. The first end of the flexible member is coupled to the spool while the second end of the flexible member is coupled to a second end of the elongate structure.

Typically, during a resting state thereof, the elongate structure assumes a linear configuration. The elongate structure is made to assume a curved configuration in which the elongate structure provides a partial annuloplasty ring. In some applications of the present invention, the first and second ends of the elongate structure are coupled together such that the elongate structure forms an annuloplasty ring. For example, the first and second ends of the elongate element are each coupled to a housing surrounding the contracting mechanism. In either application of the present invention, the annuloplasty structure is contracted by the contracting mechanism such that the dimensions of the annuloplasty structure are reduced and the structure contracts radially, thereby contracting the annulus.

As the operating physician rotates the spool of the contracting mechanism, a portion of the flexible member is wound around the spool. In response to continued rotation of the spool, increasing portions of the flexible member are wrapped around the spool, which causes the flexible member to pull on the second end of the elongate structure toward the contracting mechanism. Responsively, the compressible element is compressed between the first and second ends of the elongate structure. Thus, the flexible member helps regulate a spatial configuration of the annuloplasty structure.

In some applications of the present invention, during a resting state, the annuloplasty structure defines a linear shape. Subsequently, during implantation, the annuloplasty structure is made to assume at least part of a ring-shaped structure. The annuloplasty structure may be advanced toward the annulus of a valve in any suitable procedure, e.g., transcatheter, minimally invasive, or in an open heart procedure.

In some applications of the present invention, a delivery tool is provided for reversible coupling of a rotatable adjusting mechanism thereto, delivery of the adjusting mechanism to tissue of a patient, and rotation of a rotatable structure of the adjusting mechanism. Typically, the delivery tool facilitates implantation of the adjusting mechanism in cardiac tissue of the patient. Typically, the adjusting mechanism is coupled to an implant, e.g., an annuloplasty device, and facilitates contraction and expansion of the implant. For such applications in which the implant comprises an annuloplasty device, this contraction and expansion of the annuloplasty device facilitates, in turn, contraction and expansion of the annulus of an atrioventricular valve of the patient.

The rotatable structure of the adjusting mechanism is shaped to define proximal and distal openings and a channel extending between the proximal and distal openings. A proximal portion of an inner wall of the rotatable structure that surrounds the channel is shaped to define a threaded portion, e.g., a tapered threaded portion that decreases in diameter from the proximal opening.

The delivery tool has a distal end which is reversibly couplable to the adjusting mechanism and comprises a manipulator, e.g., a screwdriver tool. The manipulator is shaped to define a threaded portion that screws into the threaded portion of the rotatable structure. The delivery tool comprises an ergonomic proximal handle portion that comprises at least two separate rotating members which control separate functions of the manipulator at the distal end of the tool. A proximal-most first knob rotates the manipulator sufficiently to couple together the respective threaded portions of the manipulator and the rotatable structure. A second knob that is distal to the proximal-most knob facilitates rotation of the manipulator sufficiently to rotate the rotatable structure following the coupling of the manipulator to the rotatable structure. The second knob is coupled to a visual indicator which indicates the number of rotations of the screwdriver, and thereby, the number of rotations of the rotatable structure. Rotating the second knob in a first direction rotates the second knob such that it advances distally along a helical rotation path. The distal end of the helical rotation path restricts rotation of the second knob and thereby restricts rotation of the rotatable structure beyond a predetermined amount.

The rotatable structure is coupled to a locking mechanism which restricts rotation of the rotatable structure in a resting state of the locking mechanism. The delivery tool comprises an elongate locking mechanism release rod which is slidable within a lumen of the delivery tool in order to release the locking mechanism from the rotatable structure prior to the rotating of the rotatable structure responsively to the rotation of the second knob.

There is therefore provided, in accordance with some applications of the present invention, apparatus configured to be implanted in a body of a subject, including:
  an implant structure having first and second portions thereof;
  a rotatable structure coupled to the implant structure in a vicinity of the first portion thereof; and
  a flexible member having a first portion and at least one end portion thereof, at least the first portion being disposed in contact with the rotatable structure, and the at least one end portion of the flexible member being not disposed in contact with the rotatable structure, and, in response to rotation of the rotatable structure in a first direction thereof, successive portions of the flexible member contact the rotatable structure to pull the at least one end portion of the flexible member toward the first portion of the implant structure, and responsively to draw the first and second portions of the implant structure toward each other.

In some applications of the present invention, the rotatable structure includes a spool,
  the flexible member includes a longitudinal member selected from the group consisting of: a wire, a thread, a cable, and a rope, and
  in response to rotation of the spool in a first direction, successive portions of the longitudinal member wind around the spool.

In some applications of the present invention, the rotatable structure includes a rotatable structure having a plurality of teeth,
  the flexible member includes a longitudinal member selected from the group consisting of: a band and a ribbon,
  the flexible member is shaped so as to define a plurality of engaging elements, and
  in response to rotation of the rotatable structure, the plurality of teeth matingly engage the plurality of engaging elements.

In some applications of the present invention, the first and second portions of the implant structure include first and second end portions,
  the first portion of the flexible member is disposed at the first end portion of the implant structure, and
  the at least one end portion of the flexible member is disposed at the second end portion of the implant structure.

In some applications of the present invention, the flexible member includes first and second end portions,
  the at least one end portion of the flexible member defines at least one end selected from the group consisting of: the first end portion and the second end portion of the flexible member; and
  the flexible member defines the first portion thereof in a vicinity of the flexible member that is between the first and second end portions thereof.

In some applications of the present invention, the implant structure includes first and second end portions, and the implant structure defines the first portion thereof in a vicinity of the implant structure that is between the first and second end portions thereof.

In some applications of the present invention, the flexible member includes first and second end portions,
  the flexible member defines the first portion thereof in a vicinity of the flexible member that is between the first and second end portions thereof,
  the first end portion of the flexible member is coupled to the first end portion of the implant structure, and
  the second end portion of the flexible member is coupled to the second end portion of the implant structure.

In some applications of the present invention, the flexible member defines a first flexible member including first and second end portions and the first portion, and the first portion of the first flexible member defines the first end portion thereof, and
  the first end portion of the first flexible member is coupled to the rotatable structure.

In some applications of the present invention, the apparatus includes a second flexible member including first and second end portions thereof, and
  the first end portion of the second flexible member is coupled to the rotatable structure, and
  the second end portion of the flexible member is coupled to the second end portion of the implant structure.

There is additionally provided, in accordance with some applications of the present invention, a method for adjusting a dimension of an implant structure having first and second portions, including:

rotating in a first direction a rotatable structure coupled to the first portion of the implant structure;

by the rotating, contacting with the rotatable structure successive portions of a flexible member;

by the rotating, pulling an end portion of the flexible member toward the first portion of the implant structure; and responsively to the pulling, drawing the first and second portions of the implant structure toward each other.

There is further provided, in accordance with some applications of the present invention, apparatus configured to be implanted in a body of a subject, including:

an implant structure having first and second portions thereof;

a spool coupled to the implant structure in a vicinity of the first portion thereof; and a flexible member coupled at a first end thereof to the spool, and not attached at a second end thereof to the spool, the flexible member:

in response to rotation of the spool in a first direction thereof, configured to be wound around the spool, and, responsively, to pull the second end of the flexible member toward the first portion of the implant structure, and responsively to draw the first and second portions of the implant structure toward each other.

In some applications of the present invention, the flexible member is configured to be unwound from around the spool and to facilitate expansion of the implant structure in response to rotation of the spool in a second direction thereof that is opposite the first direction.

In some applications of the present invention, the implant structure includes expanded polytetrafluoroethylene (ePTFE).

In some applications of the present invention, the implant structure is coated with polytetrafluoroethylene.

In some applications of the present invention, the implant structure is configured to be implanted along an annulus of a mitral valve of the subject, the flexible member is configured to contract the implant structure in response to the rotation of the spool in the first direction, and the implant structure is configured to contract the annulus in response to the contraction thereof.

In some applications of the present invention, the second portion of the implant structure is coupled to the spool in a manner that causes the implant structure to be shaped to define an annuloplasty ring.

In some applications of the present invention, the apparatus is configured to be implanted along an annulus of a mitral valve of the subject, and the apparatus is configured to be transcatheterally advanced toward the annulus.

In some applications of the present invention, the apparatus includes a locking mechanism coupled to the implant structure and configured to restrict rotation of the spool.

In some applications of the present invention, the first and second portions are disposed adjacently to first and second ends of the implant structure, respectively, the apparatus is configured to be implanted along an annulus of a mitral valve of the subject in a manner in which the first end of the structure is distanced from the second end of the structure, and the implant structure in its implanted state defines a partial annuloplasty ring.

In some applications of the present invention, the apparatus is configured to be implanted along an annulus of a mitral valve of the subject, the first portion of the implant structure is configured to be coupled to a first location along the annulus in a vicinity of a first trigone adjacent to the mitral valve, and the second portion of the implant structure is configured to be coupled to a second location along the annulus in a vicinity of a second trigone adjacent to the mitral valve.

In some applications of the present invention, the implant structure is shaped to provide first and second ends in communication with the first and second portions, respectively, the first end is configured to be coupled to the first location along the annulus in the vicinity of the first trigone adjacent to the mitral valve, and the second end of the implant structure is configured to be coupled to the second location along the annulus in the vicinity of the second trigone adjacent to the mitral valve.

In some applications of the present invention, the first portion has first and second ends, the first end of the first portion being coupled to the spool, the second portion has first and second ends, the first end of the second portion being coupled to the spool, the apparatus includes first and second flexible members each having first and second ends, the first end of the first flexible member is coupled to the spool, and the second end of the first flexible member is coupled to the second end of the first portion, and the first end of the second flexible member is coupled to the spool, and the second end of the second flexible member is coupled to the second end of the first portion.

In some applications of the present invention, in response to rotation of the spool in a first direction thereof, respective portions of the first and second flexible members are configured to be wound around the spool, and, responsively, to pull the respective second ends of the first and second flexible members toward the spool, and responsively to draw the first and second portions of the implant structure toward each other.

In some applications of the present invention, the apparatus is configured to be implanted along an annulus of a mitral valve of a heart of the subject, a first section of the implant structure is flexible and longitudinally compressible, and a second section in series with the first section of the implant structure, the second section being flexible and less longitudinally compressible than the first section.

In some applications of the present invention, the second section is not longitudinally compressible.

In some applications of the present invention, a radius of curvature at a center of the first section is smaller than a radius of curvature at a center of the second section, when no external force is applied to the implant structure.

In some applications of the present invention, the second section of the implant structure has first and second ends thereof and a body portion disposed between the first and second ends, the second section of the implant structure being configured to be disposed along a portion of the annulus in a manner in which:

the first end of the second section is configured to be coupled to the annulus in a vicinity of a left trigone of the heart that is adjacent to a mitral valve of the subject, the second end of the second section is configured to be coupled to the annulus in a vicinity of a right trigone of the heart that is adjacent to the mitral valve, and the body portion is configured to be disposed along the annulus in a vicinity of the annulus that is between the left and right trigones.

In some applications of the present invention, the body portion disposed between the first and second ends of the second section of the implant structure has a length of 10-50 mm.

In some applications of the present invention, in the apparatus is configured to be implanted along an annulus of a mitral valve of the subject in a manner in which the implant structure is formed into at least a portion of an annuloplasty ring.

In some applications of the present invention, the apparatus includes a plurality of sutures, each suture of the plurality of sutures being configured to be fastened to a respective location along a circumference of the annulus of the subject, the plurality of sutures being configured to facilitate advancement of the implant structure toward the annulus.

In some applications of the present invention, the plurality of sutures are configured to be coupled to the implant structure at respective locations thereof that are in parallel with the respective locations along the circumference of the annulus of the subject, and the implant structure is formed into the annuloplasty ring in response to the coupling.

In some applications of the present invention, the implant structure is compressible along a longitudinal axis of the implant structure.

In some applications of the present invention, the implant structure includes a coiled structure having a lumen thereof.

In some applications of the present invention, the flexible member is disposed within the lumen of the coiled structure.

In some applications of the present invention, in response to rotation of the spool, the flexible member is configured to longitudinally compress the implant structure.

In some applications of the present invention, the apparatus includes a plurality of sutures configured to be coupled to an annulus of a mitral valve of the subject and to facilitate implantation of the implant structure along the annulus.

In some applications of the present invention, the apparatus includes a plurality of anchors respectively coupled to the plurality of sutures and configured to be anchored to tissue of the annulus of the subject.

In some applications of the present invention, the plurality of anchors are configured to lock the implant structure in place with respect to the annulus.

In some applications of the present invention, the plurality of anchors are configured to be implanted along a circumference of the annulus, and to be coupled to the implant structure in a manner which forms the implant structure into a curved configuration.

In some applications of the present invention, the spool has a first end shaped to define a first opening, and a second end shaped to define a second opening, the spool being shaped to define a channel extending from the first opening to the second opening, the channel being configured for passage therethrough of an elongate tool, and the second end of the spool has a lower surface thereof shaped to:
provide at least a portion thereof having a circumference, and
define one or more recesses at locations along the circumference.

In some applications of the present invention, the apparatus includes a mechanical element having a planar surface coupled to the lower surface of the spool, the mechanical element being shaped to provide:
a protrusion protruding out of a plane of the planar surface of the mechanical element, the protrusion being disposed within one of the recesses during a resting state of the mechanical element, in a manner that restricts rotation of the spool, and
a depressible portion coupled to the protrusion, the depressible portion being disposed in communication with the second opening of the lower surface, and configured to dislodge the protrusion from within the recess in response to a force applied thereto by the elongate tool.

In some applications of the present invention, the spool has a first end and a second end, the first end being shaped to receive a portion of a tool, and the first end of the spool has an upper surface thereof shaped to:
provide at least a portion thereof having a circumference, and
define one or more recesses at respective locations along the circumference.

In some applications of the present invention, the apparatus includes:
a mechanical element having a planar surface coupled to the upper surface of the spool, the mechanical element being shaped to provide at least one protrusion protruding out of a plane of the planar surface of the mechanical element, the protrusion being disposed within one of the recesses during a resting state of the mechanical element, in a manner that restricts rotation of the spool; and
a compressible element coupled to the second end of the spool, the compressible element being configured to be compressed and facilitate dislodging of the protrusion from within the recess in response to a force applied to the spool by the elongate tool.

There is also provided, in accordance with some applications of the present invention, apparatus for adjusting at least one dimension of an implant, including:
a rotatable structure having a first end shaped to define a first opening, and a second end shaped to define a second opening, the rotatable structure being shaped to define a channel extending from the first opening to the second opening, the channel being configured for passage therethrough of an elongate tool, and the second end of the structure having a lower surface thereof shaped to define one or more recesses; and
a mechanical element having a surface coupled to the lower surface of the rotatable structure, the mechanical element being shaped to provide:
a protrusion protruding out of a plane of the surface of the mechanical element, the protrusion being disposed within one of the recesses during a resting state of the mechanical element, in a manner that restricts rotation of the rotatable structure, and
a depressible portion coupled to the protrusion, the depressible portion being disposed in communication with the second opening of the lower surface, and configured to dislodge the protrusion from within the recess in response to a force applied thereto by the elongate tool.

In some applications of the present invention, the lower surface is shaped to provide at least a portion thereof having a circumference, and the one or more recesses are disposed along the circumference.

In some applications of the present invention, during a first period:
   the elongate tool is configured to maintain the protrusion in a position in which it is dislodged from the recess, and
   the elongate tool is configured to rotate the rotatable structure, and during a second period:
   the elongate tool is configured to remove the elongate tool from the channel and to position the protrusion in the recess, and
   the rotatable structure is restricted from being rotated.

In some applications of the present invention, during the first period, the rotatable structure is rotatable in first and second directions, the first direction being opposite the second direction.

In some applications of the present invention, the apparatus includes a housing surrounding the rotatable structure, the housing being coupled in part to a cap having a surface that is disposed in parallel with the lower surface of the rotatable structure, and the depressible portion is disposed between the lower surface of the rotatable structure and the cap, and the cap is shaped to define a recessed portion thereof configured to receive the depressible portion during a depressed state of the depressible portion.

In some applications of the present invention, the apparatus includes a housing surrounding the rotatable structure, the housing being shaped to define a recessed portion thereof configured to receive the protrusion during the resting state of the mechanical element.

In some applications of the present invention the apparatus includes, a flexible, longitudinal member having first and second end portions thereof, and at least the first end portion of the longitudinal member is coupled to the rotatable structure in a manner in which, as a result of rotation of the rotatable structure:
   the first end portion of the longitudinal member advances with respect to the rotatable structure, and
   a configuration of the longitudinal member changes.

In some applications of the present invention, in the first end portion of the longitudinal member is reversibly coupled to the rotatable structure.

In some applications of the present invention, the apparatus includes an annuloplasty device having at least one end portion,
   the annuloplasty device defines the implant,
   the rotatable structure is coupled to the annuloplasty device;
   the longitudinal member is coupled at the second end portion thereof to the at least one end portion of the annuloplasty device, and
   the rotatable structure is rotatable to advance the first end portion of the longitudinal member with respect to the rotatable structure in a manner which alters a distance between the second end portion of the longitudinal member and the rotatable structure.

In some applications of the present invention, the rotatable structure includes a spool, and the longitudinal member is coupled at at least the first end portion thereof to the spool and is wrapped around the spool in response to rotation of the spool in a first direction.

In some applications of the present invention, during a first period:
   the elongate tool is configured to maintain the protrusion in a position in which it is dislodged from the recess, and
   the elongate tool is configured to rotate the spool, and during a second period:
   the elongate tool is configured to remove the elongate tool from the channel and to position the protrusion in the recess, and
   the spool is restricted from being rotated.

In some applications of the present invention, the apparatus includes an implant, and,
   the spool is coupled to at least a portion of the implant,
   and the longitudinal member is disposed in communication with the implant and coupled at at least a first end thereof to the spool, and
   in response to rotation of the spool in a first direction thereof, the flexible member is configured to be wound around the spool, and, responsively, to contract the implant.

In some applications of the present invention, in the longitudinal member is configured to be unwound from around the spool and to facilitate expansion of the implant in response to rotation of the spool in a second direction thereof that is opposite the first direction.

In some applications of the present invention, a second end of the longitudinal member is not coupled to the spool.

In some applications of the present invention, the implant includes a compressible element shaped to define a lumen thereof, and the longitudinal member is disposed within the lumen of the compressible element.

There is further yet provided in accordance with some applications of the present inventions, apparatus for adjusting at least one dimension of an implant, including:
   a rotatable structure having a first end shaped to define a first opening, and a second end shaped to define a second opening and having a lower surface thereof, the rotatable structure being shaped to define:
      a channel extending from the first opening to the second opening, the channel being configured for passage therethrough of an elongate tool, and
      a first coupling at the lower surface of the second end thereof; and
   a mechanical element having a surface coupled to the lower surface of the rotatable structure, the mechanical element being shaped to provide:
      a second coupling configured to engage the first coupling during a resting state of the mechanical element, in a manner that restricts rotation of the rotatable structure, and
      a depressible portion coupled to the protrusion, the depressible portion being disposed in communication with the second opening of the lower surface, and configured to disengage the first and second couplings in response to a force applied thereto by the elongate tool.

There is yet additionally provided in accordance with applications of the present invention, an annuloplasty structure configured for implantation along an annulus of a mitral valve of a heart of a subject, the structure including:
   a first portion that is flexible and longitudinally compressible; and
   a second portion in series with the first portion, the second portion being flexible and less longitudinally compressible than the first portion, and having first and second ends thereof and a body portion between the first and second ends, the annuloplasty structure being configured for implantation along the annulus in a manner in which:
the first end of the second portion is configured to be coupled to the annulus in a vicinity of a left trigone adjacent to the mitral valve,
the second end of the second portion is configured to be coupled to the annulus in a vicinity of a right trigone adjacent to the mitral valve, and
the body portion of the second portion is configured to be disposed along the annulus in a vicinity of the annulus that is between the left and right trigones.

In some applications of the present invention, the body portion is not compressible.

In some applications of the present invention, a radius of curvature at a center of the first portion is smaller than a radius of curvature at a center of the second portion, when no external force is applied to the annuloplasty structure.

In some applications of the present invention, the annuloplasty structure includes an annuloplasty ring.

In some applications of the present invention, the annuloplasty structure includes a partial annuloplasty ring.

In some applications of the present invention, the body portion disposed between the first and second ends of the second portion has a length of 10-50 mm.

There is also additionally provided, in accordance with some applications of the present invention:
a rotatable structure having a first end shaped to define a first opening, and a second end shaped to define a second opening and having a lower surface thereof, the rotatable structure being shaped to define:
a channel extending from the first opening to the second opening, and
a first coupling at the lower surface of the second end thereof;
a mechanical element having a surface coupled to the lower surface of the rotatable structure, the mechanical element being shaped to provide:
a second coupling configured to engage the first coupling during a resting state of the mechanical element, in a manner that restricts rotation of the rotatable structure, and
a depressible portion coupled to the protrusion, the depressible portion being disposed in communication with the second opening of the lower surface, and configured to disengage the first and second couplings; and
a delivery tool configured to deliver the rotatable structure to a tissue site of a patient, the delivery tool including:
at least a first rotatable knob;
a torque-delivering tool coupled to the first rotatable knob, the torque-delivering tool being shaped to define a torque-delivering-tool lumen;
a screwdriver head coupled to the torque-delivering tool at a distal end thereof, the screwdriver head being shaped to define a screwdriver head and configured to rotate the rotatable structure in response to toque delivered to the screwdriver head by the torque-delivering tool in response to rotation of the first rotatable knob; and
an elongate tool coupled to the knob at a proximal end, the elongate tool being slidably coupled to the delivery tool and disposed at least in part within the torque-delivering-tool lumen, the elongate tool:
having a proximal end coupled to the first rotatable knob and,
having a distal end thereof being advanceable distally, responsively to a distal pushing of the first rotatable knob, through the screwdriver head lumen and through the channel of the rotatable structure, the distal end of the elongate tool being configured to move the depressible portion in a manner in which the elongate tool disengages the first and second couplings.

There is yet provided, in accordance with some applications of the present invention, a method, including:
coupling a delivery tool to a rotatable structure by rotating a rotatable knob of the delivery tool and screwing a screwdriver head of the delivery tool to a proximal portion the rotatable structure without rotating the rotatable structure, the rotatable structure having a first end shaped to define a first opening, and a second end shaped to define a second opening and having a lower surface thereof, the rotatable structure being shaped to define a channel extending from the first opening to the second opening, and at least one first coupling at the lower surface of the second end thereof,
subsequently to the coupling, disengaging a second coupling from within the at least one first coupling of the rotatable structure by:
pushing distally the rotatable knob,
pushing distally a distal end of an elongate tool through the channel of the rotatable structure and beyond the second opening of the rotatable structure,
responsively to the pushing distally of the distal end of the elongate tool, moving a depressible portion that is coupled to the second coupling and disposed in communication with the second opening of the lower surface of the rotatable structure; and
subsequently to the disengaging, rotating the rotatable structure by rotating at least a portion of the delivery tool.

There is also provided, in accordance with some applications of the present invention, apparatus for adjusting at least one dimension of an implant, including:
a rotatable structure having a first end shaped to define a first opening, and a second end shaped to define a second opening and having a lower surface thereof, the rotatable structure being shaped to define:
a channel extending from the first opening to the second opening, the channel being configured for passage therethrough of an elongate tool, and
at least one first coupling at the lower surface of the second end thereof; and
a mechanical element having a surface coupled to the lower surface of the rotatable structure, the mechanical element being shaped to provide:
a second coupling configured to engage the first coupling during a resting state of the mechanical element, in a manner that restricts rotation of the rotatable structure, and
a depressible portion coupled to the protrusion, the depressible portion being disposed in communication with the second opening of the lower surface, and configured to disengage the at least one first coupling and the second coupling in response to a force applied thereto by the elongate tool.

There is also provided, in accordance with some applications of the present invention, the following inventive concepts:
1. A method, comprising:
providing an implant structure having first and second portions thereof, the implant structure including:

a spool coupled to the implant structure in a vicinity of the first portion of the structure; and
a flexible member coupled at a first end thereof to the spool, and not coupled at a second end thereof to the spool;
advancing the implant structure, in a first configuration thereof, toward an annulus of the subject;
coupling the structure to the annulus; and
rotating the spool, and thereby:
winding a portion of the flexible member around the spool;
contracting the implant structure by pulling on the second end of the flexible member and thereby drawing the first and second portions of the implant structure toward each other; and
contracting the annulus.

2. The method according to inventive concept 1, wherein coupling the structure to the annulus comprises:
coupling the structure to a mitral valve of the annulus;
coupling the first portion of the implant structure to a first location along the annulus in a vicinity of a first trigone adjacent to the mitral valve; and
coupling the second portion of the implant structure to a second location along the annulus in a vicinity of a second trigone adjacent to the mitral valve.

3. The method according to inventive concept 1, wherein advancing the implant structure comprises transcatheterally advancing the implant structure.

4. The method according to inventive concept 1, wherein advancing the implant structure in the first configuration comprises advancing the implant structure in a linear configuration thereof.

5. The method according to inventive concept 1, wherein contracting the implant structure comprises rotating the spool in a first direction thereof, and wherein the method further comprises expanding the implant structure by rotating the spool in a second direction thereof that is opposite the first direction.

6. The method according to inventive concept 1, wherein advancing the implant structure in the first configuration comprises forming the structure into a curved configuration and advancing the implant structure in the curved configuration thereof.

7. The method according to inventive concept 6, wherein advancing the implant structure in the first configuration comprises forming the structure into a substantially closed curved configuration and advancing the implant structure in the closed curved configuration thereof.

8. The method according to inventive concept 6, further comprising coupling a plurality of sutures to the annulus along at least a portion of a circumference thereof, wherein:
forming the structure into the curved configuration comprises coupling the plurality of sutures to respective portions of the implant structure; and
advancing the implant structure in the curved configuration thereof comprises advancing the implant structure along the plurality of sutures.

9. A method, comprising:
providing a rotatable structure coupled to a mechanical locking element having a surface coupled to a lower surface of the rotatable structure;
implanting the rotatable structure in cardiac tissue;
advancing an elongate tool through a channel provided by the rotatable structure;
unlocking the rotatable structure from the mechanical locking element by pushing a depressible portion of the surface of the locking element;
responsively to the pushing of the depressible portion, dislodging a protrusion protruding out of a plane of the surface of the mechanical element from within a recess defined by the rotatable structure; and
in response to the dislodging, rotating the rotatable structure.

10. The method according to inventive concept 9, wherein implanting the rotatable structure in the cardiac tissue comprises implanting the rotatable structure at an intraventricular site, such that the rotatable structure is disposed in a ventricular lumen of the ventricle and a portion of the rotatable structure does not extend beyond a pericardium of a heart of the patient.

11. The method according to inventive concept 9,
wherein rotating the rotating structure comprises, during a first period, facilitating the rotating of the rotating structure by:
pushing the depressible portion; and
maintaining the protrusion in a position in which it is dislodged from the recess, and
wherein the method further comprises, during a second period:
removing the elongate tool from within the channel and facilitating positioning of the protrusion in the recess; and
restricting rotation of the rotatable structure.

12. The method according to inventive concept 11, wherein rotating the rotatable structure comprises rotating the rotatable structure in first and second directions, the first direction being opposite the second direction.

13. The method according to inventive concept 9, wherein rotating the rotatable structure comprises rotating the rotatable structure in a first direction, and wherein the method further comprises advancing a first end portion of a longitudinal member in a first direction with respect to the rotatable structure, responsively to the rotating of the rotatable structure in the first direction.

14. The method according to inventive concept 13, further comprising:
rotating the rotatable structure in a second direction; and
responsively to the rotating of the rotatable structure in the second direction, advancing the first end portion of the longitudinal member in a second direction with respect to the rotatable structure, the second direction being opposite the first direction.

15. The method according to inventive concept 13, wherein:
the longitudinal member adjusts at least one dimension of an implant including an annuloplasty device,
a second end portion of the longitudinal member is coupled to at least one end portion of the annuloplasty device, the end portion being selected from the group consisting of: a first end portion of the annuloplasty device and a second end portion of the annuloplasty device, and
the method further comprises adjusting the at least one dimension of the implant responsively to the rotating by altering a distance between the second end portion of the longitudinal member and the rotatable structure.

16. The method according to inventive concept 13, wherein advancing the first end portion of the longitudinal member in the first direction comprises wrapping at least a portion of the first end portion of the longitudinal member around the rotatable structure.

17. The method according to inventive concept 16, further comprising:
rotating the rotatable structure in a second direction opposite the first direction; and unwrapping the at least a portion of the first end portion of the longitudinal member from around the rotatable structure.

18. The method according to inventive concept 13, further comprising coupling a second end portion of the longitudinal member to a portion of tissue of a heart of a patient, and wherein advancing the first end portion of the longitudinal member comprises drawing the portion of tissue and the rotatable structure toward each other.

19. The method according to inventive concept 18, wherein coupling the second end portion of the longitudinal member to the portion of tissue of the heart of the patient comprises coupling the second end portion of the longitudinal member to at least one leaflet of an atrioventricular valve of the patient, and wherein advancing the first end portion of the longitudinal member comprises drawing the at least one leaflet and the rotatable structure toward each other.

20. A method, comprising:
providing a rotatable structure, and a mechanical locking element that is coupled to a lower surface of the rotatable structure;
implanting the rotatable structure in cardiac tissue;
advancing an elongate tool through a channel provided by the rotatable structure;
unlocking the rotatable structure from the mechanical locking element by pushing a depressible portion of the locking element;
responsively to the pushing of the depressible portion, dislodging a first coupling provided by the rotatable structure from a second coupling provided by the mechanical element; and
in response to the dislodging, rotating the rotatable structure.

21. A method, comprising:
providing an annuloplasty structure having:
a first portion that is flexible and longitudinally compressible; and
a second portion in series with the first portion, the second portion being flexible and less longitudinally compressible than the first portion, and having first and second ends thereof and a body portion disposed between the first and second ends;
implanting the annuloplasty structure along an annulus of a valve of a subject by:
coupling the first end of the second portion to the annulus in a vicinity of a left trigone adjacent to the valve;
coupling the second end of the second portion the annulus in a vicinity of a right trigone adjacent to the valve; and
coupling the body portion of the second portion along the annulus in a vicinity of the annulus that is between the left and right trigones; and
compressing the first portion of the annuloplasty structure while substantially not compressing the second portion of the annuloplasty structure.

22. The method according to inventive concept 21, wherein providing the annuloplasty ring comprising providing an annuloplasty ring having a radius of curvature at a center of the first portion is smaller than a radius of curvature at a center of the second portion, when no external force is applied to the annuloplasty structure.

23. The method according to inventive concept 21, wherein providing the annuloplasty structure comprises providing a closed annuloplasty ring.

24. The method according to inventive concept 21, wherein providing the annuloplasty structure comprises providing a partial annuloplasty ring.

25. The method according to inventive concept 21, wherein attaching the second end of the second portion the annulus comprising attaching the second end of the second portion the annulus at a distance between from the first end of between 10 and 50 mm.

26. Apparatus, comprising:
a rotatable structure having a first end and a second end, the first end being shaped to receive a portion of a tool and having an upper surface thereof shaped to:
provide at least a portion thereof having a circumference, and
define one or more recesses at respective locations along the circumference;
a mechanical element having a planar surface coupled to the upper surface of the rotatable structure, the mechanical element being shaped to provide at least one protrusion protruding out of a plane of the planar surface of the mechanical element, the protrusion being disposed within one of the recesses during a resting state of the mechanical element, in a manner that restricts rotation of the rotatable structure; and
a compressible element coupled to the second end of the rotatable structure, the compressible element being configured to be compressed and facilitate dislodging of the protrusion from within the recess in response to a force applied to the rotatable element by the elongate tool.

27. The apparatus according to inventive concept 26, wherein the rotatable structure comprises a spool, and wherein the apparatus further comprises a flexible member configured to be coupled at at least a first end thereof to the spool and to be wrapped around the spool in response to rotation thereof.

28. The apparatus according to inventive concept 27, further comprising an implant, wherein:
the spool is coupled to at least a portion of the implant, and the flexible member is disposed in communication with the implant and coupled at at least a first end thereof to the spool, and
in response to rotation of the spool in a first direction thereof, the flexible member is configured to be wound around the spool, and, responsively, to contract the implant.

29. The apparatus according to inventive concept 28, wherein the flexible member is configured to be unwound from around the spool and to facilitate expansion of the implant in response to rotation of the spool in a second direction thereof that is opposite the first direction.

30. The apparatus according to inventive concept 28, wherein a second end of the flexible member is not coupled to the spool.

31. The apparatus according to inventive concept 28, wherein the implant comprises a compressible element shaped to define a lumen thereof, and wherein the flexible member is disposed within the lumen of the compressible element.

32. A method, comprising:
providing an annuloplasty structure having:
a first portion that is flexible and longitudinally compressible; and
a second portion in series with the first portion, the second portion being flexible and less longitudinally compressible than the first portion, and having first and second ends thereof and a body portion disposed between the first and second ends;

implanting the annuloplasty structure along an annulus of a valve of a subject by:
coupling the first end of the second portion to the annulus in a vicinity of a left trigone adjacent to the valve;
coupling the second end of the second portion the annulus in a vicinity of a right trigone adjacent to the valve; and
coupling the body portion of the second portion along the annulus in a vicinity of the annulus that is between the left and right trigones; and
compressing the first portion of the annuloplasty structure while substantially not compressing the second portion of the annuloplasty structure.

33. The method according to inventive concept 32, wherein providing the annuloplasty ring comprising providing an annuloplasty ring having a radius of curvature at a center of the first portion is smaller than a radius of curvature at a center of the second portion, when no external force is applied to the annuloplasty structure.

34. The method according to inventive concept 32, wherein providing the annuloplasty structure comprises providing a closed annuloplasty ring.

35. The method according to inventive concept 32, wherein providing the annuloplasty structure comprises providing a partial annuloplasty ring.

36. The method according to inventive concept 32, wherein attaching the second end of the second portion the annulus comprising attaching the second end of the second portion the annulus at a distance between from the first end of between 10 and 50 mm.

37. Apparatus, comprising:
a rotatable structure having a first end and a second end, the first end being shaped to receive a portion of a tool and having an upper surface thereof shaped to:
provide at least a portion thereof having a circumference, and
define one or more recesses at respective locations along the circumference;
a mechanical element having a planar surface coupled to the upper surface of the rotatable structure, the mechanical element being shaped to provide at least one protrusion protruding out of a plane of the planar surface of the mechanical element, the protrusion being disposed within one of the recesses during a resting state of the mechanical element, in a manner that restricts rotation of the rotatable structure; and
a compressible element coupled to the second end of the rotatable structure, the compressible element being configured to be compressed and facilitate dislodging of the protrusion from within the recess in response to a force applied to the rotatable element by the elongate tool.

38. The apparatus according to inventive concept 37, wherein the rotatable structure comprises a spool, and wherein the apparatus further comprises a flexible member configured to be coupled at at least a first end thereof to the spool and to be wrapped around the spool in response to rotation thereof.

39. The apparatus according to inventive concept 38, further comprising an implant, wherein:
the spool is coupled to at least a portion of the implant, and the flexible member is disposed in communication with the implant and coupled at at least a first end thereof to the spool, and in response to rotation of the spool in a first direction thereof, the flexible member is configured to be wound around the spool, and, responsively, to contract the implant.

40. The apparatus according to inventive concept 39, wherein the flexible member is configured to be unwound from around the spool and to facilitate expansion of the implant in response to rotation of the spool in a second direction thereof that is opposite the first direction.

41. The apparatus according to inventive concept 39, wherein a second end of the flexible member is not coupled to the spool.

42. The apparatus according to inventive concept 39, wherein the implant comprises a compressible element shaped to define a lumen thereof, and wherein the flexible member is disposed within the lumen of the compressible element.

43. A method, comprising:
providing a rotatable structure, and a mechanical locking element that is coupled to a lower surface of the rotatable structure;
implanting the rotatable structure in cardiac tissue;
advancing an elongate tool through a channel provided by the rotatable structure;
unlocking the rotatable structure from the mechanical locking element by pushing a depressible portion of the locking element;
responsively to the pushing of the depressible portion, dislodging a first coupling provided by the rotatable structure from a second coupling provided by the mechanical element; and
in response to the dislodging, rotating the rotatable structure.

The present invention will be more fully understood from the following detailed description of applications thereof, taken together with the drawings, in which:

BRIEF DESCRIPTION OF THE DRAWINGS

FIG. 5 is a schematic illustration of the annuloplasty structure, in accordance with some other applications of the present invention;

FIGS. 6A-B, 7, and 8A-B are schematic illustrations of the contracting mechanism that is used to contract the annuloplasty structure, in accordance with some applications of the present invention;

FIGS. 9-11, 12A-B, and 13 are schematic illustrations of a method for implanting the annuloplasty structure of FIGS. 1-4, in accordance with some applications of the present invention;

FIGS. 14A-C are schematic illustrations of a locking mechanism used to lock the contracting mechanism, in accordance with some applications of the present invention;

FIGS. 16A-C are schematic illustrations of respective components of an adjusting mechanism of a spool assembly, in accordance with some applications of the present invention;

FIGS. 18-19 are schematic illustrations of the delivery tool of FIG. 1 coupled to the adjusting mechanism, in accordance with some applications of the present invention;

FIGS. 21A-C are schematic cross-sectional illustrations of the delivery tool of FIG. 1, in accordance with some applications of the present invention;

FIGS. 22-23 are schematic illustrations of the delivery tool of FIG. 1 at different stages of use thereof, in accordance with some applications of the present invention;

FIG. 26 is a schematic illustration of the delivery tool of FIG. 1 coupled to the adjusting mechanism which comprises a pinion that is coupled to a rack, in accordance with some applications of the present invention;

DETAILED DESCRIPTION OF THE EMBODIMENTS

Figure 1:
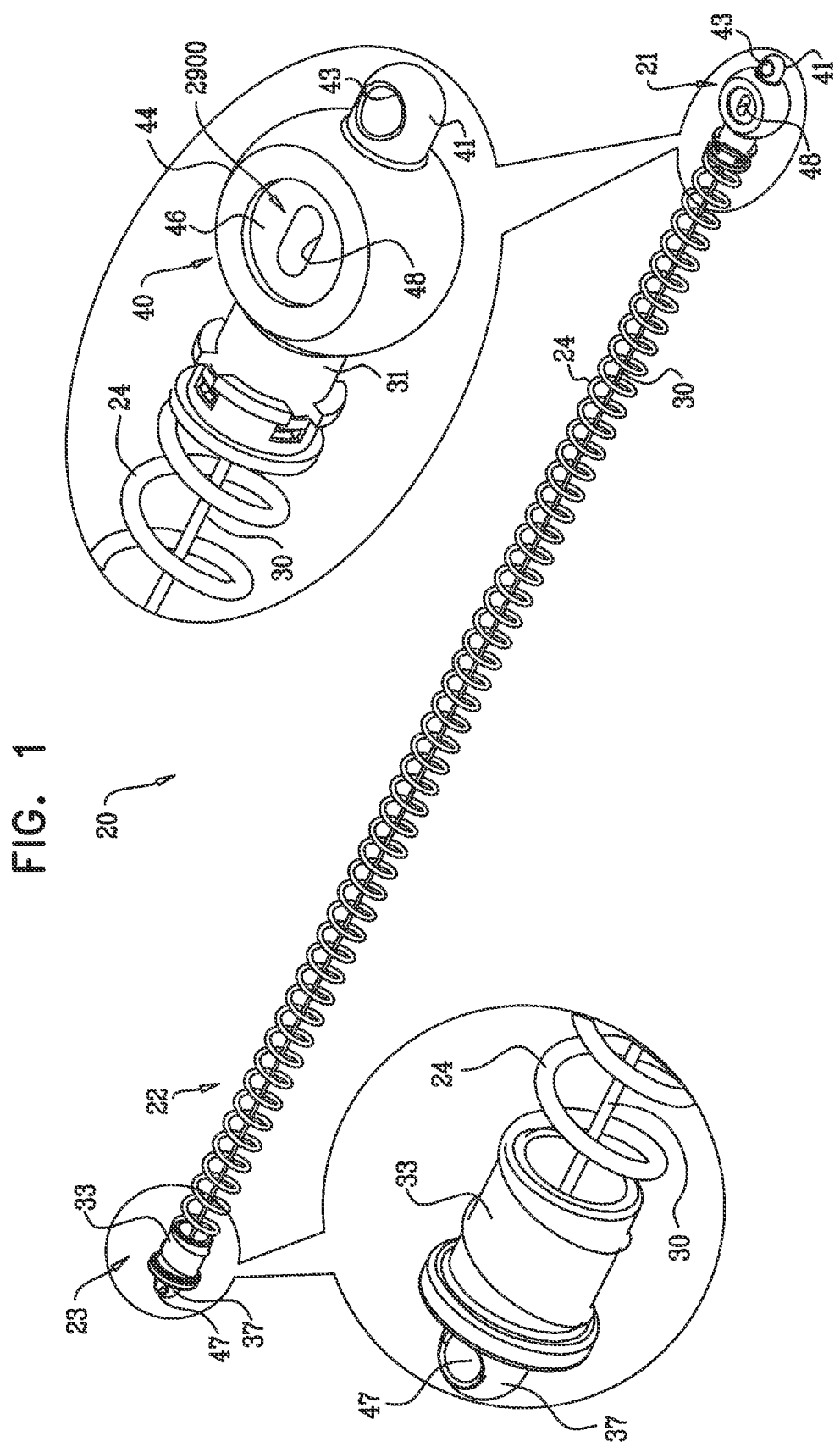
FIG. 1 is a schematic illustration of an annuloplasty structure in a resting state thereof, in accordance with some applications of the present invention.
Figure 2:
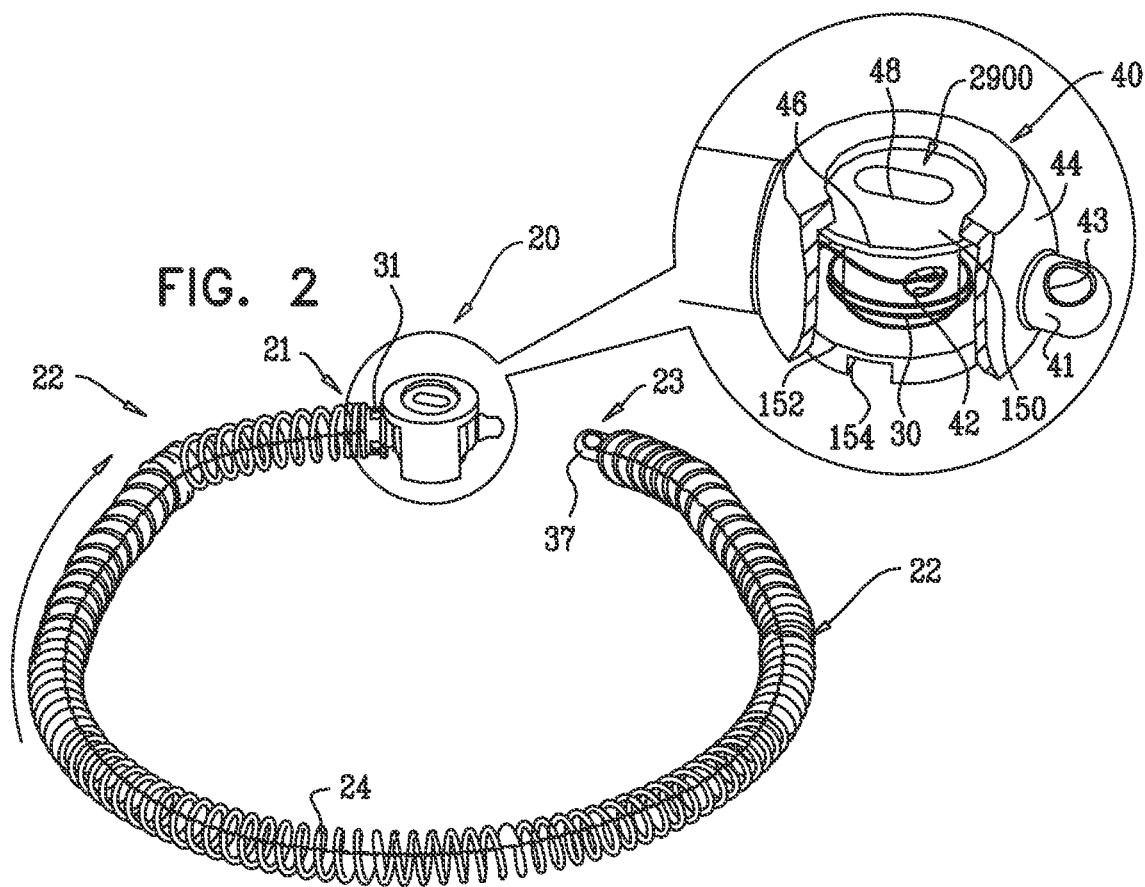
FIGS. 2-3 are schematic illustrations of the annuloplasty structure in respective contracted states thereof, in accordance with some applications of the present invention.
Figure 3:
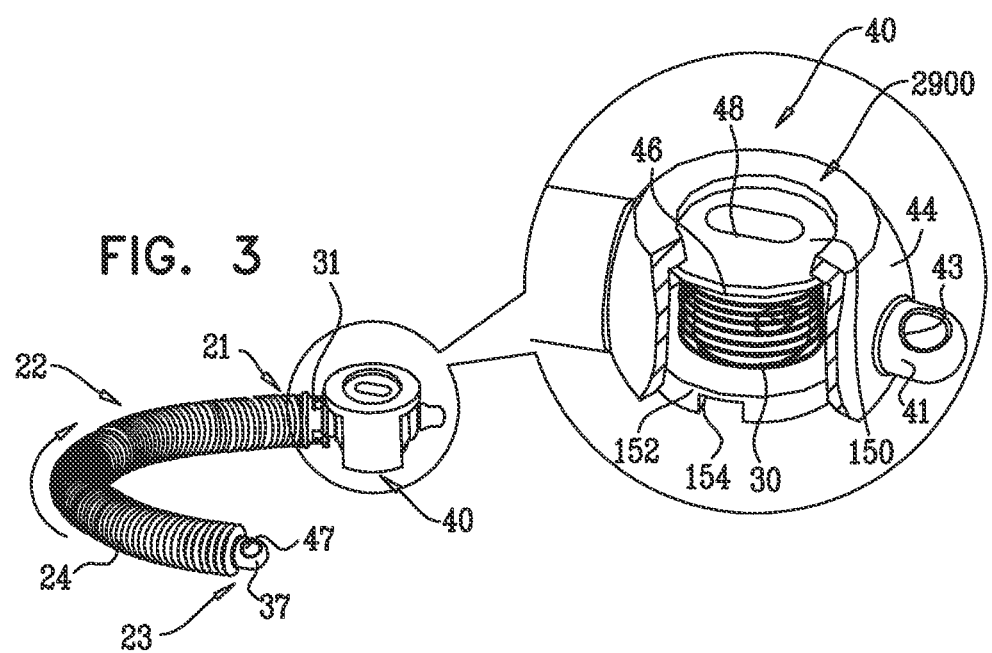

Reference is now made to FIGS. 1-3, which are schematic illustrations of a system 20 for repairing a dilated annulus of a subject comprising an implant structure, e.g., an annuloplasty structure 22, comprising a body portion 24, a flexible contracting longitudinal member 30 (herein referred to as "contracting member" or "flexible member"), and an adjusting mechanism 40, in accordance with some applications of the present invention. FIG. 1 shows structure 22 in a resting state thereof in which structure 22 defines a linear, elongate structure having a longitudinal axis thereof. At least a portion, e.g., the entirety, of body portion 24 comprises a compressible material, e.g., a coiled element, as shown by way of illustration and not limitation. For example, body portion 24 may comprise stent-like struts, or a braided mesh. Typically, body portion 24 defines a lumen along the longitudinal axis of structure 22 which houses flexible contracting member 30. Flexible contracting member 30 comprises a wire, a ribbon, a rope, or a band, comprising a flexible metal. Flexible contracting member 30 is coupled at a first end portion thereof to adjusting mechanism 40 which is coupled to a first end 21 of structure 22. A second end portion of flexible contracting member 30 is coupled to a second end 23 of structure 22. Typically, during the resting state, flexible contracting member 30 is disposed in parallel with the longitudinal axis of structure 22. That is, flexible member 30, for some applications does not comprise a continuous band that runs through the entire lumen of the annuloplasty devices described herein, and flexible member 30 has at least one free end portion.

Typically, flexible contracting member 30 comprises a wire, a cable, or a rope, and taken together with the compressible element of body portion 24 and the braided mesh surrounding body portion 24, imparts flexibility to the entire annuloplasty structure.

Typically, body portion 24 comprises a flexible biocompatible material, e.g., nitinol, stainless steel, platinum iridium, titanium, expanded polytetrafluoroethylene (ePTFE), or cobalt chrome. In some applications of the present invention, body portion 24 is coated with PTFE (Polytetrafluoroethylene). In other applications of the present invention, body portion 24 comprises accordion-like compressible structures which facilitate proper cinching of the annulus when structure 22 is contracted. Body portion 24, when compressed, e.g., typically along a longitudinal axis of structure 22, enables portions of annuloplasty structure 22 to contract and independently conform to the configuration of the annulus of the mitral valve of a given subject. Thus, the compressible element of body portion 24 facilitates contraction of the annulus in response to contraction of structure 22.

Typically, flexible contracting member 30 comprises a flexible and/or superelastic material, e.g., nitinol, polyester, stainless steel, or cobalt chrome, and is configured to reside chronically within structure 22. In some applications of the present invention, flexible contracting member 30 comprises a braided polyester suture (e.g., Ticron). In some applications of the present invention, flexible contracting member 30 is coated with polytetrafluoroethylene (PTFE). In some applications of the present invention, flexible contracting member 30 comprises a plurality of wires that are intertwined to form a rope structure.

Adjusting mechanism 40 comprises a housing 44 which houses a rotatable structure 2900, or a spool 46. Spool 46 has a cylindrical body that is disposed perpendicularly with respect to the longitudinal axis of structure 22. As shown in FIG. 2, spool 46 is shaped to provide a hole 42 for coupling of the first end of flexible contracting member 30 thereto and, thereby, to adjusting mechanism 40. For some applications of the present invention, spool 46 is shaped to define one or more holes 42 configured for looping a portion of contracting member 30 therethrough, as described hereinbelow. In such an application: (a) a middle portion, which defines a first end portion, of contracting member 30 is coupled to spool 46 by being looped through one or more holes 42, (b) first and second portions that extend from the first end portion looped through spool 46 extend toward a second end 23 of structure 22, and (c) first and second free ends of contracting member 30 are coupled to second end 23 of structure 22 and define a second end portion of contracting member 30.

Spool 46 is shaped to define a channel 48 which extends through the cylindrical portion of spool 46 from an opening provided by an upper surface 150 of spool 46 to an opening provided by a lower surface 152 of spool 46. Channel 48 provides a lumen which is disposed along an axis that is perpendicular to the longitudinal axis of structure 22 in its elongate, linear configuration. As described hereinbelow, a distal portion of a screwdriver engages spool 46 via channel 48 and rotates spool 46 in response to a rotational force applied to the screwdriver. The rotational force applied to the screwdriver rotates spool 46 via the portion of the screwdriver that is disposed within channel 48 of spool 46.

FIG. 2 shows partial contraction of structure 22 in response to a rotational force applied to spool 46. In response to the rotational force, a portion of flexible contracting member 30 is wrapped around spool 46, as shown in the enlarged image of FIG. 2. That is, during rotation of rotatable structure 2900 in a first direction, successive portions of member 30 contact spool 46. As flexible contracting member 30 is wrapped around spool 46, the second end of member 30 is pulled toward adjusting mechanism 40 in the direction as indicated by the arrow. Pulling the second end of flexible contracting member 30 toward mechanism 40 pulls second end 23 of structure 22 toward first end 21 of structure 22, in the direction as indicated by the arrow. Responsively, the compressible element of body portion 24 is longitudinally compressed, thereby contracting structure 22.

It is to be noted that the linear structure 22 contracts to form a curved structure 22, as shown, by way of illustration and not limitation. In some applications of the present invention, contraction of structure 22 forms the structure into a curved configuration. Alternatively, structure 22 is made to assume the curved configuration prior to contracting thereof, and during the contracting, the curved structure is contracted. That is, without being formed into a curved configuration prior to the contracting, structure 22 is compressed linearly along the longitudinal axis thereof.

In some applications of the present invention, the contracting of structure 22 enables structure 22 to assume the configuration shown. Alternatively, or additionally, prior to contraction, structure 22 is anchored, or otherwise fastened, at least in part to the annulus of the valve of the subject at respective locations along structure 22. The anchoring, or otherwise fastening, of structure 22 to the annulus enables structure 22 to assume the configuration shown, as described hereinbelow.

FIG. 3 shows further contraction of structure 22 in response to continued rotation of spool 46. As shown in the enlarged image of FIG. 3, a larger portion of flexible contracting member 30 is wrapped around spool 46 (i.e., member 30 is looped many times around element 46), as compared with the portion of flexible contracting member 30 that is wrapped around spool 46 (as shown in the enlarged image of FIG. 2). Responsively to the wrapping of flexible contracting member 30 around spool 46, the compressible element of body portion 24 is further longitudinally compressed, and structure 22 is further contracted. As such, structure 22 provides an adjustable partial annuloplasty ring.

Reference is now made to FIGS. 1-3. First end 21 of structure 22 comprises a coupling member 31 which couples a first end of body portion 24 to adjusting mechanism 40. Typically, the first end of body portion 24 is welded to coupling member 31. Adjusting mechanism 40 is coupled to a first suture fastener 41 that is shaped to define a hole 43 for passage therethrough of a suture. Second end 23 of structure 22 comprises a second suture fastener 37 that is shaped to define a hole 47 for passage therethrough of a suture. Second end 23 of structure 22 comprises a coupling member 33 which couples a second end of body portion 24 to suture fastener 37. Typically, the second end of body portion 24 is welded to coupling member 33.

Figure 4:
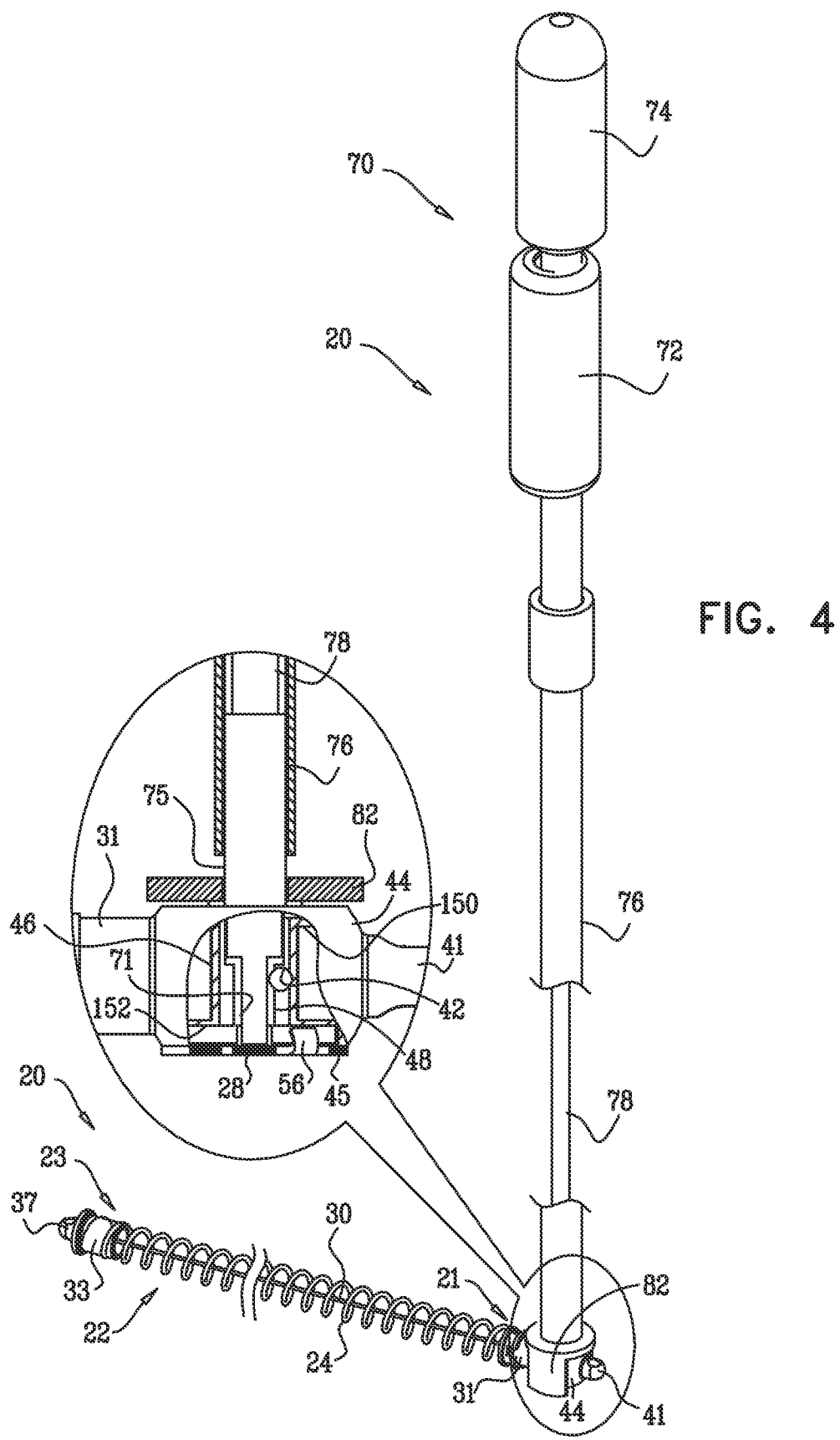
FIG. 4 is a schematic illustration of the annuloplasty structure of FIG. 1 being coupled to an elongate tool, in accordance with some applications of the present invention.

Reference is now made to FIG. 4, which is a schematic illustration of system 20 comprising an elongate tool 70 that is reversibly coupled to adjusting mechanism 40 of structure 22, in accordance with some applications of the present invention. Tool 70 comprises an elongate body portion 76 which houses a flexible rod 78 that is coupled at a distal end thereof to a screwdriver head 75. Typically, rod 78 functions as a screwdriver which applies force to screwdriver head 75 (that is disposed within channel 48 of spool 46) in order to rotate spool 46, and thereby facilitate contraction of structure 22. A proximal portion of tool 70 comprises rotatable structures 72 and 74 which rotate with respect to each other and cause flexible rod 78 to rotate with respect to body portion 76.

(In this context, in the specification and in the claims, "proximal" means closer to the orifice through which tool 70 is originally placed into the body of the subject, and "distal" means further from this orifice.)

In some applications of the present invention, tool 70 is coupled to an annuloplasty sizer and the annuloplasty structure is wrapped around at least a portion of the sizer. Once wrapped around the sizer, the flexible member is contracted such that the annuloplasty structure hugs and is stabilized around the sizer. The sizer helps position the annuloplasty structure along the annulus and stabilize the structure as it is being contracted.

Typically, tool 70 facilitates the advancement of structure 22 and subsequent contraction thereof. The distal portion of tool 70 comprises a housing 82 which surrounds housing 44 of structure 22 and stabilizes housing 44 during the advancement and contraction of structure 22. Flexible rod 78 is coupled at a distal end thereof to screwdriver head 75. Screwdriver head 75 is shaped to define a distal protrusion 71 which is disposed within channel 48 of spool 46 during the advancement of structure 22 toward the annulus of the subject, and during the contraction of structure 22.

In some applications of the present invention, an advancement tool other than tool 70 is used to facilitate advancement of structure 22 toward the annulus, e.g., the tool described hereinbelow with reference to FIGS. 17-26. Following coupling of structure 22 to the annulus, the advancement tool is decoupled from structure 22 and extracted from within the body of the subject. Subsequently, tool 70 may be advanced toward housing 44 of structure 22 and facilitate contraction of structure 22. In such applications of the present invention, the advancement tool may be coupled at a distal end thereof to an annuloplasty sizer and structure 22 is tightened around the sizer during the advancement of structure 22 toward the annulus.

A distal portion of protrusion 71 rests against a depressible portion 28 of a locking mechanism 45. Typically, locking mechanism 45 comprises a mechanical element having a planar surface that is coupled to spool 46. In some applications of the present invention, at least a portion of mechanism 45 is coupled to, e.g., soldered to or disposed adjacently to, housing 44. Typically, lower surface 152 of spool 46 is shaped to define one or more (e.g., a plurality, as shown) of recesses, e.g., holes (not shown for clarity of illustration). Locking mechanism 45 is shaped to provide a protrusion 56, or a first coupling, which protrudes out of the plane of the planar surface of the mechanical element of mechanism 45 and into one of the recesses, or a second coupling, of lower surface 152 of spool 46, as described hereinbelow.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

The enlarged image in FIG. 4 shows a cross-section of spool 46 and locking mechanism 45 in a resting state thereof in which protrusion 56 of locking mechanism 45 is disposed within one of the recesses of lower surface 152 of spool 46. In such a configuration, protrusion 56 locks in place spool 46 and restricts rotation thereof.

Protrusion 56 remains disposed within the recess of lower surface 152 of spool 46 until a force is applied to locking mechanism 45 which causes protrusion 56 to be dislodged from within the recess of lower surface 152 of spool 46. Typically, protrusion 56 is coupled to depressible portion 28 of locking mechanism 45. As described hereinbelow, tool 70 is pushed distally causes protrusion 71 of screwdriver head 75 to press down on depressible portion 28. As a result, protrusion 56 of locking mechanism 45 is pushed down together with depressible portion 28, and is thereby dislodged from within the recess of lower surface 152 of spool 46.

Once spool 46 is released from protrusion 56 of locking mechanism 45, flexible rod 78 of tool 70 is rotated in order to rotate screwdriver head 75, and thereby spool 46.

Typically, housing 82 of tool 70 functions to provide a reference force against housing 44 of structure 22 during the rotation of rotating element 46.

Tool 70 may be used in order to advance structure 22 toward the annulus in an open heart procedure, minimally-invasive procedure, and/or in a transcatheter procedure. For applications in which tool 70 is used during a transcatheter procedure, tool 70 comprises a substantially longer, more flexible body portion than if used during an open-heart or minimally-invasive procedure. In some applications of the present invention, tool 70 is used to advance structure 22 toward the annulus in a linear configuration (as shown), in a curved configuration (i.e., in manner in which structure 22 defines an annuloplasty band or a partial annuloplasty ring), or in a closed configuration (i.e., a configuration in which second end 23 of structure 22 is coupled to housing 44 such that structure 22 defines an annuloplasty ring).

FIG. 5 shows a system 120 for repairing a dilated annulus of a subject comprising an annuloplasty structure 122 that defines an annuloplasty ring, in accordance with some applications of the present invention. Annuloplasty structure 122 comprises first and second ends 21 and 23, respectively, which are coupled to (e.g., welded to) a housing 144 that houses adjusting mechanism 40. Housing 144 is shaped to provide first and second coupling members 31 and 35 which are coupled to first and second ends 21 and 23, of structure 122.

In some applications of the present invention, structure 122 comprises a linear, elongate structure in a resting configuration thereof. Prior to implantation, first and second ends 21 and 23 of structure 122 are welded or otherwise attached to coupling members 31 and 35, respectively, thereby facilitating the formation of structure 122 into a substantially ring-shaped structure. As described hereinabove with respect to structure 22 with reference to FIGS. 1-3, structure 122 comprises a body portion 24 defining a lumen for housing flexible contracting member 30. Typically, body portion 24 comprises a compressible element. As described hereinabove, a first end of flexible contracting member 30 is coupled to adjusting mechanism 40, while a second end of flexible contracting member 30 is coupled to second end 23 of structure 122.

It is to be noted that for some applications of the present invention, flexible contracting member 30 may be coupled at both its first and second end portions, e.g., first and second ends, to spool 46 of adjusting mechanism 40. In some applications of the present invention, a first end of flexible contracting member 30 is coupled to spool 46 while a second end of flexible contracting member 30 is coupled to the housing which houses spool 46. For some applications, contracting member 30 comprises a continuous band that is looped through a portion of spool 46.

As shown, structure 122 defines a substantially ring-shaped configuration, e.g., a "D"-shaped configuration, as shown, which conforms to the shape of the annulus of a mitral valve of the subject. Prior to contracting of structure 122, the compressible element of body portion 24 is relaxed and structure 122 defines a first perimeter thereof. Structure 122 provides portions 49 which comprise a material in a configuration in which portions 49 are flexible and less longitudinally compressible, e.g., not longitudinally compressible, with respect to the compressible element of body portion 24. Portions 49 are configured to be disposed along the fibrous portion of the annulus that is between the trigones of the mitral valve of the heart when structure 122 is anchored, sutured, fastened or otherwise coupled to the annulus of the mitral valve. Portions 49 impart rigidity to structure 122 in the portion thereof that is disposed between the fibrous trigones such that structure 122 better mimics the conformation and functionality of the mitral valve. That is, during rotation of spool 46, and the concurrent contraction or expansion of structure 122, energy is not expended on contracting or expanding portions 49.

Typically, both portions 49 have a combined length of 10-50 mm.

Thus, structure 122 defines a compressible portion and a non-compressible portion. Typically, a radius of curvature at a center of the compressible portion of body portion 24 is smaller than a radius of curvature at a center of less-compressible portions 49, when no external force is applied to the annuloplasty structure.

It is to be noted that the compressible element of body portion 24 and less-compressible portions 49 comprise flexible coiled elements by way of illustration and not limitation. For example, the compressible element of body portion 24 and less-compressible portions 49 may comprise stent-like struts, or a braided mesh. In either configuration, portions 49 are chronically longitudinally compressed in a resting state of structure 122.

Housing 82 of tool 70 is coupled to structure 122 by surrounding housing 144. Tool 70 facilitates contracting of structure 122 via adjusting mechanism 40 in a manner as described hereinabove with respect to the contracting of structure 22 with reference to FIGS. 1-4. Tool 70 is shown as comprising a coupling element 77 which couples screwdriver head 75 to flexible rod 78.

Reference is again made to FIG. 5. It is to be noted that, structure 122 may be provided independently of less-compressible portions 49. In such applications of the present invention, the annuloplasty structure comprises a fully compressible ring, e.g., a continuous ring.

Reference is again made to FIG. 5. It is to be noted that housing 144 may be disposed at any suitable location along structure 122, and not only in between portions 49. For example, housing 144 may be coupled to the section of body portion 24 that is compressible. In some applications of the present invention, housing 144 may be disposed in the middle of the section of body portion 24 that is compressible. In some applications of the present invention, housing 144 may be coupled to structure 122 at an interface between a first end of portion 49 and the section of body portion 24 that is compressible. In such applications of the present invention, portions 49 may be combined to form one substantially less-compressible portion having first and second ends that are in series with the compressible portion of body portion 24. For some applications, a plurality of housings and adjusting mechanisms 40 described herein may be coupled to the annuloplasty structure. Each adjusting mechanism 40 may be coupled to a respective contracting member 30 which controls a respective portion of the annuloplasty structure.

FIGS. 6A-B show a relationship between individual components of adjusting mechanism 40, in accordance with some applications of the present invention. As shown, housing 144 is shaped to provide coupling members 31 and 35 for coupling first and second ends of the annuloplasty structure thereto. Adjusting mechanism 40 is shown as comprising housing 144, by way of illustration and not limitation. For applications in which mechanism 40 comprises housing 44 (described hereinabove with reference to FIGS. 1-4), housing 44 comprises only coupling member 31 on one side, and a suture fastener on the other side of housing 44.

Spool 46 is configured to be disposed within housing 144 and defines an upper surface 150, a lower surface 152 and a cylindrical body portion disposed vertically between surfaces 150 and 152. Spool 46 is shaped to provide channel 48 which extends from an opening provided by upper surface 150 to an opening provided by lower surface 152. The cylindrical body portion of spool 46 is shaped to define one or more holes 42. Typically, flexible contracting member 30 is coupled to spool 46 via hole 42. In some applications of the present invention, flexible contracting member 30 comprises a continuous ring-shaped band which passes through hole 42 of spool 46.

Lower surface 152 of spool 46 is shaped to define one or more (e.g., a plurality, as shown) recesses 154 disposed between portions 155 of lower surface 152. Although four recesses 154 are shown by way of illustration and not limitation, it is to be noted that any suitable number of recesses 154 may be provided, e.g., between 1 and 10 recesses. It is to be noted that four recesses 154 are shown by way of illustration and not limitation and that any suitable number of recesses 154 may be provided.

Locking mechanism 45 is coupled to lower surface 152. In some applications of the present invention, at least a portion of locking mechanism 45 is welded to housing 144. For other applications, locking mechanism 45 rests against spool 46 and is held in place with respect to spool 46 by a distal cap, as described hereinbelow. Typically, locking mechanism 45 defines a mechanical element having a planar surface that has at least one slit 58. Locking mechanism 45 is shaped to provide a protrusion 56 which projects out of a plane defined by the planar surface of the mechanical element. Slit 58 defines a depressible portion 28 of locking mechanism 45 that is disposed in communication with protrusion 56. Depressible portion 28 is moveable in response to a force applied thereto typically by tool 70, as described hereinabove, and as shown in detail hereinbelow with reference to FIGS. 8A-B.

Reference is now made to FIGS. 6A-B. It is to be noted that locking mechanism 45 may be coupled to housing 44 as described hereinabove with reference to FIGS. 1-4.

Figure 7:
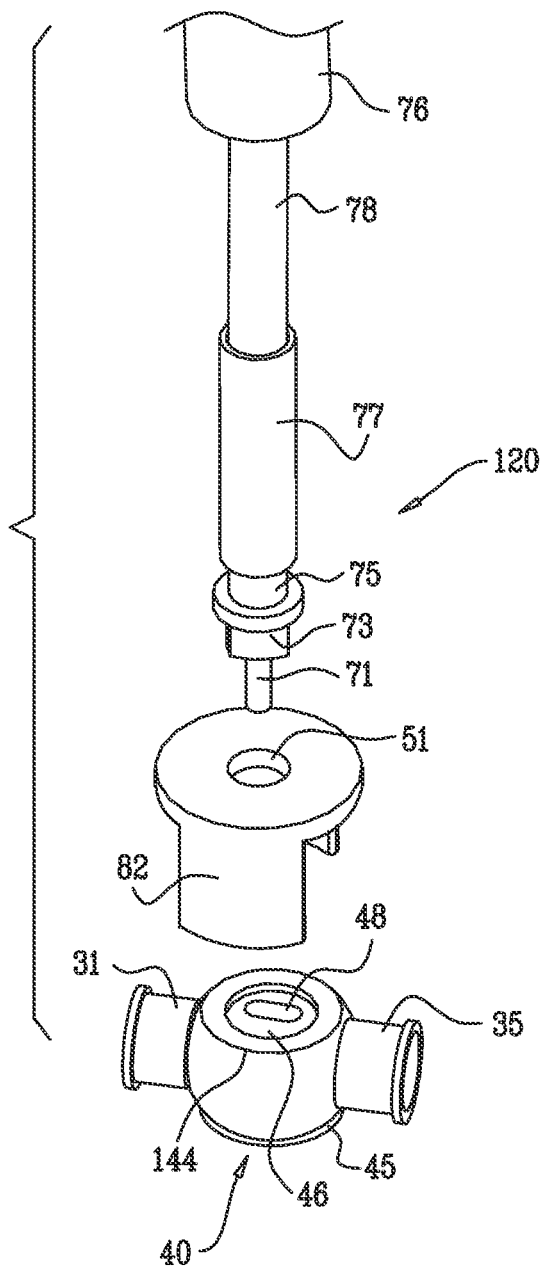

FIG. 7 is a schematic illustration adjusting mechanism 40 and components of tool 70 that is configured to be coupled to adjusting mechanism 40, in accordance with some applications of the present invention. Tool 70 comprises body 76, e.g., a sleeve, and a flexible, rotatable rod 78 disposed within a sleeve provided by body 76. A coupling element 77 couples screwdriver head 75 to flexible rod 78. Typically, screwdriver head 75 is shaped to define a proximal cylindrical structure which is housed within a lumen provided by coupling element 77. A distal end of screwdriver head 75 is shaped to define a distal insert portion 73 which is designated for insertion within channel 48 of spool 46. Housing 82 is coupled to a distal end of tool 70 and functions as a cage which surrounds housing 144. Typically, during rotating of spool 46 by tool 70, housing 82 provides a reference force which facilitates the applying of a force to spool 46 by tool 70.

Following sufficient contraction of the annuloplasty structure, tool 70 and housing 82 are disengaged from housing 144 of the annuloplasty structure and are extracted from within the heart of the subject.

FIGS. 8A-B are schematic illustrations of the locking and unlocking of spool 46, in accordance with some applications of the present invention. FIG. 8A shows adjusting mechanism 40 in a locked configuration in which protrusion 56 of locking mechanism 45 is disposed within a recess 54 of lower surface 152 of spool 46. FIG. 8B shows the unlocking of spool 46 by the dislodging of protrusion 56 from recess 54 of spool 46.

Reference is now made to FIGS. 6A-B, 7, and 8A-B. During a resting state of the locking mechanism, depressible portion 28 is disposed perpendicularly with respect to a longitudinal axis of channel 48, and protrusion 56 is disposed within one of recesses 154 and thereby locks spool 46 in place with respect to housing 144 such that rotation of spool 46 is restricted (FIG. 8A). In the resting state of locking mechanism 45, the distal portion of protrusion 71 of screwdriver head 75 rests against depressible portion 28 of locking mechanism 45.

FIG. 8B shows screwdriver head 75 of tool 70 applying a pushing force to locking mechanism 45 (in the direction as indicated by the arrow). The pushing force pushes downward protrusion 71 of screwdriver head 75 such that protrusion 71 pushes downward depressible portion 28, e.g., typically at a non-zero angle with respect to spool 46. Pushing portion 28 downward pushes downward protrusion 56 such that it is dislodged from within recess 154 of spool 46, and, thereby unlocking spool 46. Following the unlocking, tool 70 facilitates the rotation of screwdriver head 75 in order to rotate spool 46.

Channel 48 of spool 46 is shaped to accommodate the dimensions of insert 73 and protrusion 71 of screwdriver head 75. Insert 73 is shaped to provide an upper portion having a width that is wider than the protrusion 71 coupled thereto. In turn, channel 48 of spool 46 is shaped to accommodate insert 73 and protrusion 71 by defining an upper portion and a lower portion thereof in which the upper portion of channel 48 is wider than the lower portion. The narrower lower portion of channel 48 ensures that protrusion 71 is not advanced distally beyond a certain point as the narrower lower portion of channel 48 restricts passage therethrough of the upper, wider portion of insert 73.

It is to be noted that housing 144 and structure 122 are shown in FIGS. 6A-B, 7, and 8A-B by way of illustration and not limitation, and that applications described herein may be practiced in combination with housing 44 and/or structure 22.

Reference is again made to FIGS. 6A-B, 7, and 8A-B. Following rotation of spool 46 by tool 70, insert 73 of tool 70 is removed from within channel 48 spool 46 by pulling on tool 70, and depressible portion 28 returns to its resting state, i.e., perpendicular with respect to the longitudinal axis of channel 48. As depressible portion 28 returns to its resting state, protrusion 56 is introduced within one of the plurality of recesses 154 of lower surface 152 of spool 46 and thereby restricts rotation of spool 46.

It is to be noted that an outer sheath surrounds screwdriver portion 75 of tool 70 in FIGS. 8A-B. Screwdriver portion 75 is shaped to define a ring-shaped portion at a portion thereof that is disposed adjacently to housing 144. The ring-shaped portion has a diameter that is larger than the diameter of the opening provided by housing 144, and therefor is restricted from passage through housing 144. By pushing on tool 70, the ring shaped portion pushes against housing 144 in order to push the annuloplasty structure away from tool 70. As screwdriver portion 75 pushes against housing 144, the outer sheath is pulled proximally in order to pull tool 70 away from the annuloplasty structure.

Reference is now made to FIGS. 9-11, 12A-B, and 13, which are schematic illustrations of a method for implantation of structure 22 of system 20 along an annulus 92 of the mitral valve of the subject, in accordance with some applications of the present invention. Typically, prior to advancement of the annuloplasty structure toward the annulus, a plurality of sutures are sutured, anchored, fastened, or otherwise coupled around the annulus. Typically, the sutures are accessible from a site outside the body of the subject. FIG. 9 shows a plurality of sutures 110, e.g., metal or fabric such as polyester, that are coupled via respective anchors 108 to respective locations 98, 100, and 102 along annulus 92 of the mitral valve. The dilated mitral valve is shown as having anterior leaflet 94 and posterior leaflet 96. Typically, each suture 110 is coupled to a respective helical anchor 108. As shown, sutures 110 are looped around a portion of anchors 108. In some applications of the present invention, sutures 110 may be coupled at respective distal ends thereof to respective anchors 108. Anchors 108 are corkscrewed into tissue of annulus 92, thereby indirectly coupling sutures 110 to annulus 92.

Typically, during transcatheter procedures, sutures 110 are anchored to annulus 92, as shown in FIG. 9. It is to be noted that sutures 110 may be anchored to the annulus, as shown, during open-heart or minimally-invasive procedures.

It is to be noted that sutures 110 are anchored at locations 98, 100, and 102 by way of illustration and not limitation, and that sutures 110 may be anchored or otherwise fastened to any suitable location along annulus 92. Furthermore, it is to be noted that any suitable number of sutures 110 may be anchored or otherwise fastened to annulus 92, in accordance with the size of the dilated mitral valve of the subject. For example, between 2 and 20 sutures, typically between 2 and 14 sutures, may be anchored to annulus 92 via respective helical anchors 108.

During open-heart or minimally-invasive procedures to repair the dilated mitral valve, sutures 110 may be sutured directly to annulus 92 using techniques known in the art. Typically, a plurality of sutures are sutured along the entire circumference of the annulus in accordance with the size of the dilated annulus. In some applications of the present invention, adjacently-disposed sutures may overlap in part. In some applications of the present invention, the sutures are sutured to annulus in a manner in which the suture defines a portion disposed in the tissue, and first and second portions extending from either side of the portion of the suture that is disposed within the tissue. In such applications of the present invention, the suture may be sutured to the tissue in a manner in which the first and second portions of the tissue are disposed at a distance, e.g., 4 mm, from each other.

Figure 10:
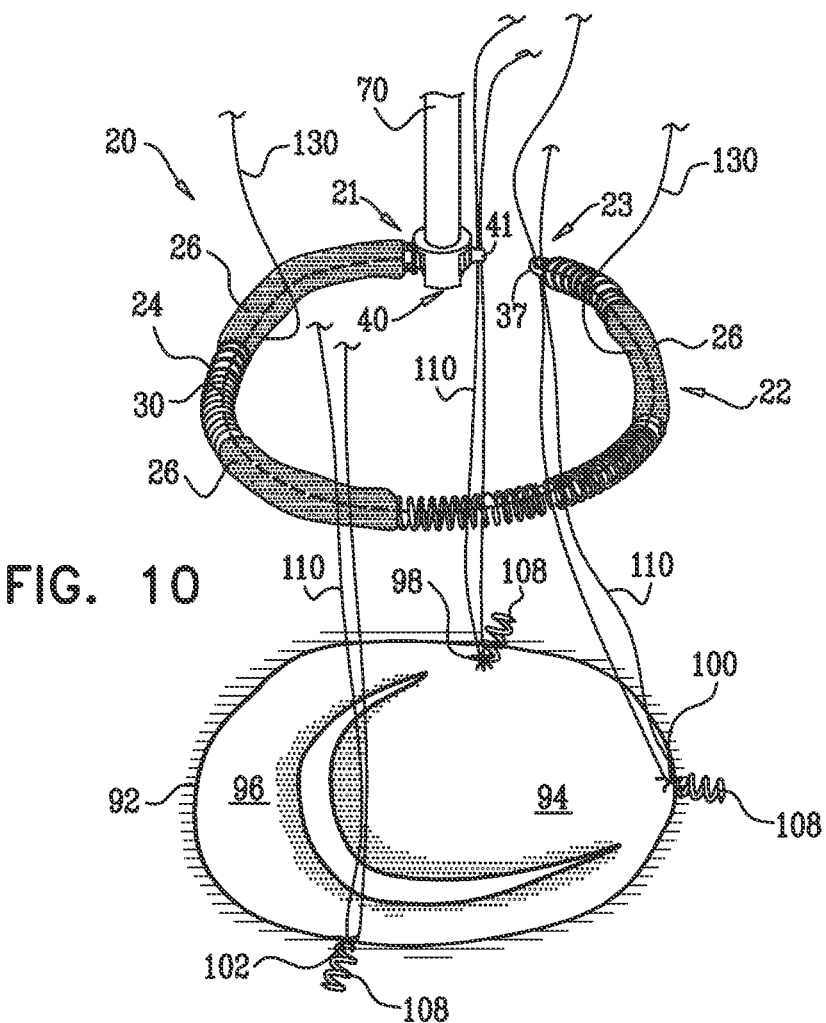

FIG. 10 shows the advancement of structure 22 along sutures 110 and toward annulus 92. Structure 22 is shown as comprising body portion 24 which houses flexible contracting member 30 and is surrounded by a braided mesh 26 (for clarity of illustration, portions of body portion 24 are shown as not being surrounded by mesh 26). Typically, body portion 24 comprises a compressible element, as described herein. Typically, braided mesh 26 comprises a flexible material, e.g., metal or fabric such as polyester, and is longitudinally compressible. Typically, body portion 24 comprises a compressible element. Mesh 26 compresses responsively to the compression of the compressible element of body portion 24.

Prior to advancement toward annulus 92, structure 22 is coupled to tool 70, as described hereinabove. For applications in which structure 22 is transcatheterally implanted along annulus 92, structure 22 may be advanced linearly through the advancement catheter and pushed therethrough by tool 70. Typically, the advancement catheter is transeptally advanced toward the left atrium of the heart of the subject and tool 70 is advanced through the catheter.

In some applications of the present invention, structure 22 may be coupled at respective ends thereof to housing 44 of adjusting mechanism 40 such that structure 22 is advanced in a closed, substantially ring-shaped configuration. For applications in which structure 22 is transcatheterally advanced in a closed configuration, structure 22 may be folded, or otherwise collapsed, such that it fits within the lumen of the advancement catheter.

As shown in FIG. 10, prior to advancement of structure 22 toward the annulus, sutures 110 are threaded through respective portions of structure 22 outside the body of the patient. Suture 110 that is sutured to location 98 of annulus 92 is threaded through suture fastener 41. Suture 110 that is sutured to location 100 is threaded through suture fastener 37. Suture 110 that is sutured to location 102 is threaded through mesh 26 at a portion along structure 22 that is between ends 21 and 23. Since locations 98, 100, and 102 are generally circumferential about annulus 92, following the threading of sutures 110 through structure 22, structure 22 is shaped (from its original linear configuration as shown in FIGS. 1 and 4) into a substantially circular, or curved, configuration, as shown, as it is advanced toward annulus 92. In some applications of the present invention, structure 22 comprises a shape-memory alloy, e.g., nitinol, which enables structure 22 to assume the configuration as shown, independently of the threading therethrough of sutures 110.

Typically, each suture 110 defines a portion that is looped around a portion of a respective anchor 108, and first and second portions extending from the looped portion. Respective ends of the first and second portions of each suture 110 are accessible from outside the body of the subject. As shown, the two portions of respective sutures 110 may be threaded through fasteners 41 and 37 and through mesh 26. Alternatively, a first portion of each suture 110 may be threaded through a respective hole defined by fasteners 41 and 37 and through mesh 26 while a second portion of each suture 110 may be threaded around respective fasteners 41 and 37 and around mesh 26. In such applications of the present invention, following the positioning of structure 22 along annulus 92, the first and second portions of sutures 110 are tied together around fasteners 41 and 37, and around mesh 26.

Typically, locations 98 and 100 are by way of illustration and not limitation, on or adjacently to the trigones of the heart that are near the mitral valve. Thus, first and second ends 21 and 23 of structure 22 will be disposed on or adjacently to the trigones. In such applications of the present invention, a portion of structure 22 is not disposed in an area between the fibrous trigones. In some applications of the present invention, respective portions of body portion 24 that are disposed adjacently to first and second ends 21 and 23 of structure 22 are less compressible, e.g., not compressible, as compared to the compressible element of body portion 24.

It is to be noted that first and second ends 21 and 23 of structure 22 are disposed in respective vicinities of the left and right trigones by way of illustration and not limitation, and that respective ends 21 and 23 may be coupled to any suitable portion along the annulus. That is, annuloplasty structure 22 may be coupled along the annulus in any suitable orientation and at any suitable location along the annulus.

Structure 22 is coupled to sutures 130, e.g., metal or fabric, at distal ends thereof. As described hereinbelow, sutures 130 facilitate the advancement of respective anchors toward structure 22 following its initial anchoring to annulus 92 via sutures 110. It is to be noted that only two sutures 130 are coupled to structure 22 by way of illustration and not limitation, and that any suitable number of sutures 130 may be coupled to structure 22. Typically, the number of sutures 130 coupled to structure 22 is determined in accordance with the size of the dilated annulus, and thereby the number of anchoring sites needed in order to properly anchor structure 22 to the dilated annulus.

Figure 11:
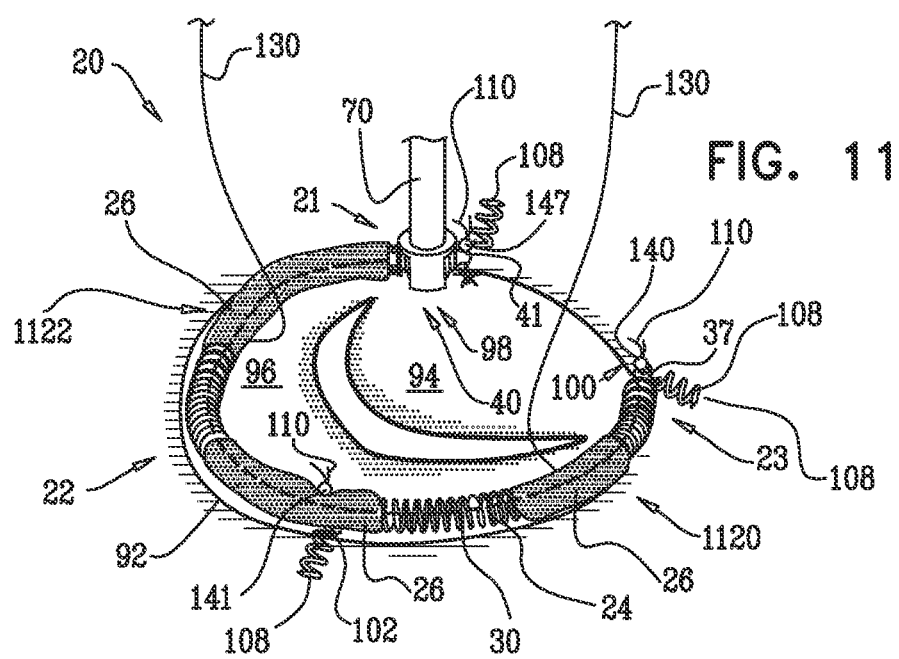

FIG. 11 shows structure 22 following the positioning and initial suturing thereof to annulus 92. Respective beads 140, 141, and 147 are slid along sutures 110 toward an upper surface of structure 22. Beads 140, 141, and 147 each comprise a crimping mechanism which crimps sutures 110 and, thereby beads 140, 141, and 147 lock sutures 110 in place with respect to structure 22, thereby locking in place structure 22 with respect to annulus 92. Excess portions of sutures 110 are clipped proximally to beads 140, 141, and 147 and removed from within the heart of the subject.

Following the initial locking of structure 22 with respect to annulus 92, sutures 130 remain extending from structure 22 and accessible from outside the body of the subject. Sutures 130 facilitate advancement of anchors toward structure 22 in order to further anchor structure 22 to annulus 92 at locations 1120 and 1122. It is to be noted that two sutures 130 are shown by way of illustration and not limitation, and that any suitable number of sutures 130 may be coupled to structure 22.

Following implantation of structure 22 along annulus 92 and prior to contraction of structure 22, structure 22 provides a partial annuloplasty ring, or band, having a distance between first and second ends 21 and 23 of structure 22 such that structure 22 defines a first perimeter thereof.

FIGS. 12A-B show further anchoring of structure 22 to annulus 92. A sheath 1151 has a lumen which houses an anchor advancement tube 1150, which in turn, has a lumen thereof. Sheath 1151 and advancement tube 150 are advanced along suture 130 and toward structure 22. A distal end of anchor advancement tube 1150 is coupled to an anchor which is used to anchor structure 22 to annulus 92. Typically, the anchor is advanced to annulus 92 with respect to structure 22. In some applications of the present invention, the anchor is advanced through body portion 24, as shown in FIGS. 12A-B. In some applications of the present invention, the anchors are advanced through braided mesh 26 that surrounds body portion 24.

FIG. 12A shows the anchor comprising a helical anchor 108 having a pointed distal tip. Anchor 108 is corkscrewed with respect to the compressible element of body portion 24 such that helical anchor 108 intertwines with the compressible element of body portion 24 and is thereby coupled to the compressible element. Further corkscrewing of helical anchor 108 advanced a distal portion of anchor 108 beyond structure 22 and into tissue of annulus 92, thereby further anchoring structure 22 to annulus 92.

FIG. 12B shows the anchor comprising a pronged anchor 105 having a substantially rigid, body portion and a plurality of prongs 107 each having a pointed distal end. Body portion of anchor 105 is coupled to structure 22 and prongs 107 are advanced through tissue of annulus 92. Typically, anchor 105 comprises a shape-memory alloy, e.g., nitinol, which enables prongs 107 to transition from the substantially straight configuration, to a curved configuration in which each prong 107 curves proximally to assume a substantially "U"-shaped configuration, as shown. Typically, during advancement of anchor 105 toward structure 22, anchor 105 is disposed within sheath 1151 in a configuration in which prongs are aligned in a straight configuration.

It is to be noted that anchor 105 is shown as comprising two prongs 107 by way of illustration and not limitation, and that any suitable number or prongs may be used.

Typically, anchor 105 is compressed within a tubular housing prior to being advanced through tissue of the annulus. The tubular housing is first advanced through the annuloplasty structure prior to the pushing of anchor 105 from within the tubular housing and into tissue of the annulus. In some applications of the present invention, the tubular housing comprises anchor advancement tube 1150 which is first advanced through a portion of the annuloplasty structure, e.g., is advanced between adjacent coils of the annuloplasty structure, prior to advancing anchor 105 from within tube 150 and into tissue of the annulus. As anchor 105 penetrates tissue of annulus 92, prongs 107 gradually bend away from a longitudinal axis of the body portion of anchor 105 in order to assume their respective bent configurations. As prongs 107 assume their respective bent configurations, their pointed ends puncture surrounding tissue in order to further anchor anchor 105 to tissue of the patient. In its expanded, bent configuration, anchor 105 is configured to restrict proximal motion of thereof through the tissue.

Once structure 22 is further anchored to annulus 92, a respective bead 146 and 148 is advanced along each suture 130 and toward an upper surface of structure 22 (FIG. 13). Beads 146 and 148 lock in place structure 22 at locations 1120 and 1122, respectively, in a manner as described hereinabove with respect to beads 140, 141, and 147. Following the advancing of beads 146 and 148 toward the upper surface of structure 22, excess portions of sutures 130 are clipped proximally to beads 146 and 148 and are removed from the heart of the subject.

FIG. 13 shows the contracting annulus 92 in response to the contracting of structure 22. Structure is typically contracted only following the locking in place structure 22 to annulus 92 by the beads. The flexible rod housed within tool 70 (as described hereinabove with reference to FIGS. 4-7, and 8A-B) is pushed downward, as shown by arrow 1, in order to release locking mechanism 45 from spool 46 of adjusting mechanism 40, as described hereinabove. Once free of locking mechanism 45, spool 46 is rotated in response to a rotational force applied thereto by tool 70, as indicated by arrow 2. Rotation of spool 46 contracts structure 22, by wrapping at least a portion of member 30 around spool 46, and thereby pulling on the second end of flexible contracting member 30 toward the first end of flexible contracting member 30 such that flexible member pulls on second end 23 of structure 22 toward first end 21 of structure 22 (in a direction as indicated by arrow 13), as described hereinabove with reference to FIGS. 2 and 3. At the same time, first end 21 of structure 22 is pulled toward second end 23 of structure 22.

Following the contraction of structure 22, first and second ends 21 and 23, respectively, of structure 22 are pulled toward each such that structure 22 assumes a second perimeter. The second perimeter following the contracting of structure 22 is smaller than the first perimeter of structure 22 prior to the contracting. Structure 22 may be contracted such that the second perimeter defines any suitable dimension.

It is to be noted that structure 22 may be anchored to annulus 92 such that structure 22 is positioned along the entire perimeter of annulus 92. Alternatively, structure 22 may be anchored to annulus 92 such that it is positioned partially along the perimeter of annulus 92.

Figure 14B:
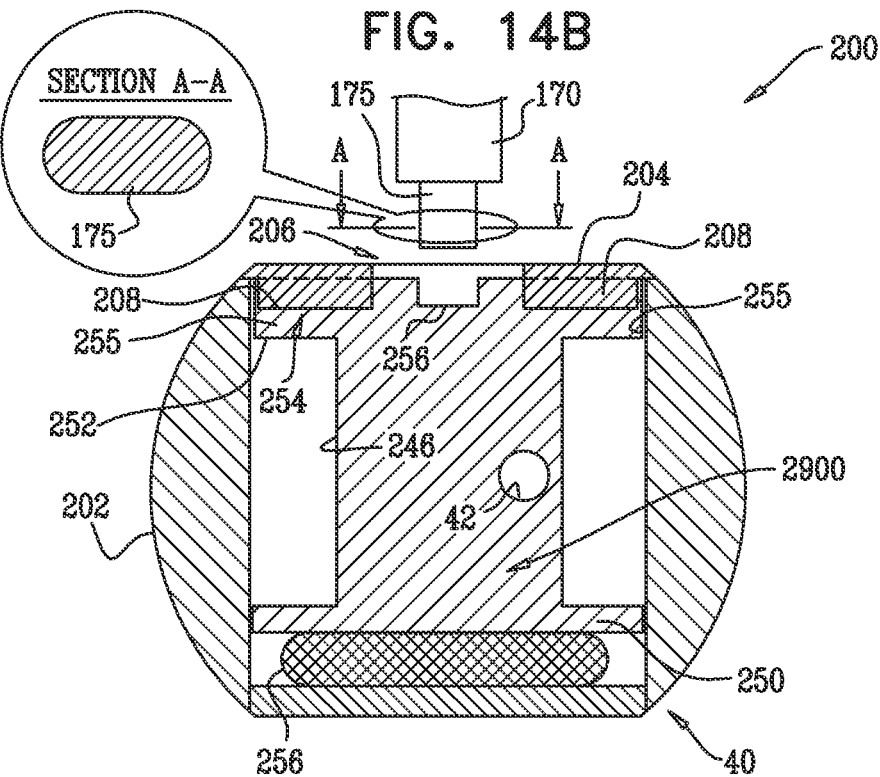
Figure 14C:
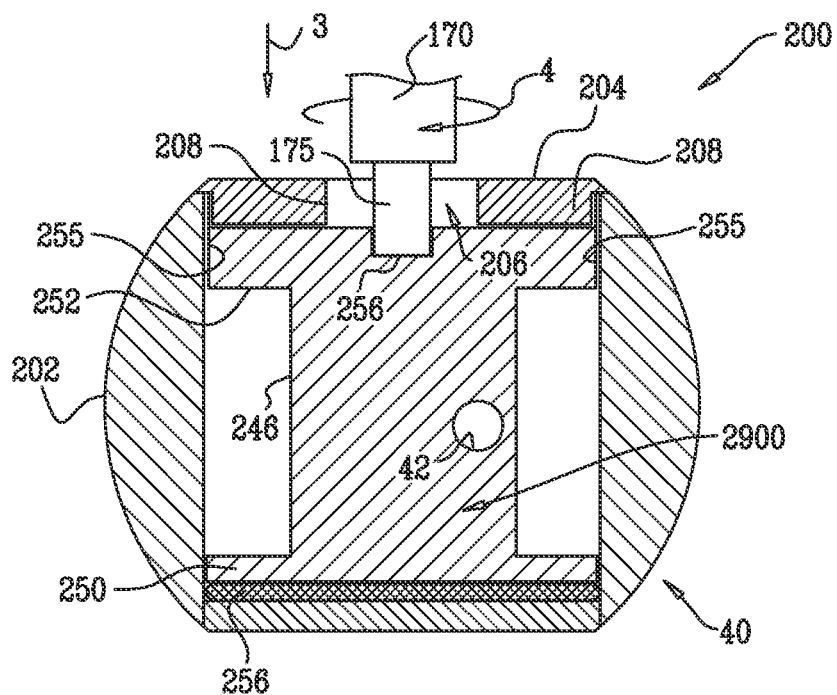

Reference is now made to FIGS. 14A-C, which are schematic illustrations of a locking mechanism 200 configured to lock in place adjusting mechanism 40 of the annuloplasty structures described herein, in accordance with some applications of the present invention. Locking mechanism 200 is disposed within housing 202, that is similar to housings 44 and 144 described hereinabove, with the exception that an underside of a planar upper surface 204 of housing 202 is shaped to define a plurality of projections 208 which (a) project out of a plane defined by planar upper surface 204 and downward into the body of housing 202, and (b) engage spool 246.

FIG. 14A shows components of locking mechanism 200. Upper surface 204 is welded or soldered to the body of housing 202. A spool 2246, in turn, has an upper portion 252 and a lower portion 250. Upper portion 252 is shaped to provide raised surfaces 255 which define a plurality of recesses 254. Although four recesses 254 are shown by way of illustration and not limitation, it is to be noted that any suitable number of recesses 254 may be provided, e.g., between 1 and 10 recesses. In turn, upper surface 204 may be shaped to provide a suitable number of projections 208, e.g., between 1 and 10 projections. Lower portion 250 of spool 2246 rests against a compressible element 256, e.g., a spring or stent-like element (as shown), that is coupled to a lower portion of housing 202.

Recesses 254 of upper portion 252 of spool are is shaped to define a screw-driver-engaging recess 256 extending 0.1-2.0 mm downward from an upper surface of spool 246. Recess 256 provides a means by which at least a distal portion of an elongate tool engages and facilitates rotation spool 246. Typically, a distal portion of the elongate tool is advanced through an opening 206 in upper surface 204 of housing 202 prior to engaging spool 246 via recess 256. As shown hereinbelow, opening 206 is shaped to accommodate a size of a screwdriver tool.

Typically, recesses 254 are disposed along a circumference of at least a portion of upper portion 252 of spool 246. Similarly, projections 208 of upper surface 204 of housing 202 are disposed along a circumference of at least a portion of upper surface 204 of housing 202.

FIG. 14B shows locking mechanism 200 in a resting state thereof. Lower portion 250 of spool 246 rests against compressible element 256 in a relaxed, uncompressed state thereof. As such, in the resting state of locking mechanism 200, upper portion 252 of spool 246 contacts upper surface 204 of housing 202 in a manner in which projections 208 of upper surface 204 are disposed within recesses 254 of upper surface 252 of spool 246. In such a manner, by being disposed within respective recesses 254 of spool 246, projections 208 restrict rotation spool 246.

FIG. 14C shows the unlocking of locking mechanism 200 in response to the disengaging of spool 246 from upper surface 204 of housing 202. A distal portion of an elongate tool 170 is advanced through hole 206 defined by upper surface 204, and subsequently into recess 256 provided by upper portion 252 of spool 246. Tool 170 is shaped to define a distal screwdriver portion 175 that first within recess 256 of spool 246 that is defined by grooves 154. As shown in section A-A of FIG. 14B, screwdriver portion 175 is shaped to define an elliptical cross-section by way of illustration and not limitation. For example, screwdriver portion 175 is shaped to define a rectangular cross-section. In some applications of the present invention, screwdriver portion 175 is shaped to define a "T"-shaped cross-section.

Tool 170 is pushed downward, as indicated by arrow 1, thereby pushing downward spool 246 and, responsively, compressing compressible element 256. In response to the compressing of compressible element 256, upper portion 252 of spool 246 is distanced from upper surface 204 of housing 202, and thereby, projections 208 are dislodged from within recesses 264 of upper portion 252 of spool 246. Once locking mechanism 200 is unlocked and spool 246 is free of projections 208, tool 170 is rotated (in the direction as indicated by arrow 2) in order to rotate spool 246 and wrap flexible contracting member 30 therearound, thereby facilitating contracting of the annuloplasty structure responsively to the rotating.

Following the rotating of spool 246 and the responsive contracting of the annuloplasty structure, tool 170 is pulled away from spool 246, allowing compressible element 256 to assume its relaxed, uncompressed state. As compressible element 256 assumes its relaxes, uncompressed state, compressible element 256 pushed spool 246 upwards in a manner in which recesses 254 are once again engaged by projections 208 of upper surface 204 of housing 202. Such engaging locks spool 246 in place and restricts rotation thereof.

It is to be noted that tool 170 may also be used to expand the annuloplasty structure by rotating in a direction that is opposite the direction used in order to contract the annuloplasty structure.

Figure 15:
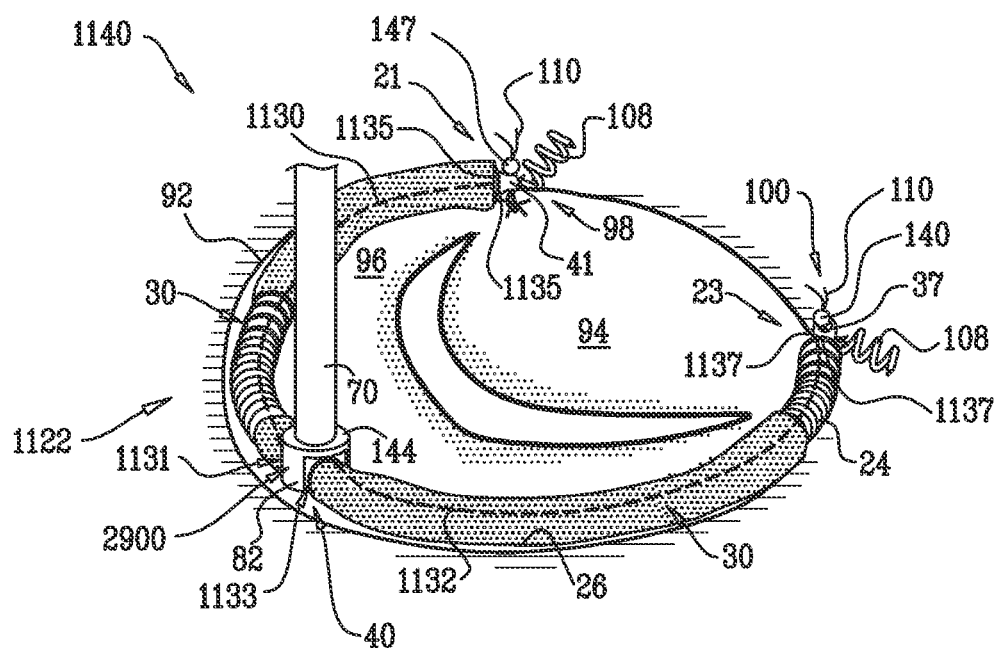
FIG. 15 is a schematic illustration of an annuloplasty structure for contracting the annulus, in accordance with some other applications of the present invention.

FIG. 15 shows a system 1140 comprising an annuloplasty structure 1122 comprising adjusting mechanism 40 coupled to one or more flexible members 30, in accordance with some applications of the present invention. Structure 1122 comprises a body portion 24 having a compressible element, as described hereinabove. Body portion 24 is typically surrounded by braided mesh 26, as described hereinabove.

It is to be noted that portions of braided mesh 26 are shown for clarity of illustration and that body portion 24 of structure 1122 may be entirely surrounded by braided mesh 26. Adjusting mechanism 40 is disposed with respect to structure 1122 at a portion thereof that is between first and second ends 21 and 23 thereof, e.g., at the center, as shown by way of illustration and not limitation. For some applications, the portions of structure 1122 disposed on either side of adjusting mechanism 40 may comprise distinct segments. It is to be further noted that adjusting mechanism 40 may be disposed with respect to annuloplasty structure 1122 at any portion thereof (e.g., generally in the middle of structure 1122, as shown).

Adjusting mechanism 40 comprises a spool 46 as described hereinabove. Spool 46 of adjusting mechanism 40 of system 1140 is coupled to a first end 1131 of a first flexible contracting member 1130 and to a first end 1133 of a second flexible contracting member 1132. A second end 1135 of first flexible member 1130 is coupled to first end 21 of structure 1122. A second end 1137 of second flexible member 1132 is coupled to second end 23 of structure 1122. Flexible members 1130 and 1132 each comprise a wire, a ribbon, a rope, or a band, comprising a flexible metal.

During rotation of spool 46 of adjusting mechanism 40, as described hereinabove, respective portions of first and second flexible members 1130 and 1132 are wrapped around spool 46. That is, successive portions of respective members 1130 and 1132 contact spool 46 during the rotation thereof. Responsively to the winding of the portions of first and second flexible members 1130 and 1132 around spool 46, second ends 1135 and 1137 of flexible members 1130 and 1132, respectively, are pulled toward adjusting mechanism 40. As second ends 1135 and 1137 of flexible members 1130 and 1132, respectively, are pulled toward adjusting mechanism 40, first and second ends 21 and 23 of structure 1122 are pulled toward adjusting mechanism 40, thereby drawing together first and second ends 21 and 23.

It is to be noted that system 1140 is shown are comprising first and second flexible members 1130 and 1132 by way of illustration and not limitation. For some applications, adjusting mechanism 40 may be coupled to more than two flexible members 30. For other applications, adjusting mechanism 40 of structure 1122 may be coupled to only one flexible contracting member 30. In such an application: (1) a first free end of the flexible contracting member 30 is coupled to first end 21 of structure 1122, (2) a second free end of contracting member 30 is coupled to second end 23 of structure 1122, and (3) a portion of member 30 disposed between the first and second free ends thereof is looped through spool 46 of adjusting mechanism 40. In such an application, rotating spool 46 in a first direction winds a middle portion of member 30 around spool 46 such that: (1) successive portions of member 30 contact spool, and (2) the first and second free ends of member 30 (and thereby, first and second ends 21 and 23, respectively, of structure 1122) are pulled toward adjusting mechanism 40.

FIG. 16A shows a relationship among individual components of adjusting mechanism 40, in accordance with some applications of the present invention. Adjusting mechanism 40 is shown as comprising spool housing 1042 which defines an upper surface 1041 and a recessed portion 142. Spool 46 is configured to be disposed within housing 1042 and defines an upper surface 150, a lower surface 152 and a cylindrical body portion disposed vertically between surfaces 150 and 152. Spool 46 is shaped to provide a driving interface, e.g., a channel 48, which extends from an opening provided by upper surface 150 to an opening provided by lower surface 152. Channel 48 of the driving interface is shaped to define a hexagonal channel or a channel having another shape. For some applications, as described herein, a portion of an inner wall of spool 46 that defines channel 48 is shaped so as to define a threaded portion for receiving a threaded screwdriver tool. The cylindrical body portion of spool 46 is shaped to define holes 42a and 42b which function as respective coupling sites for coupling flexible member 30 to spool 46.

Holes 42a and 42b may be shaped to define holes, as shown, or slits through which respective portions of flexible member 30 are looped therethrough. In some embodiments, the outer surface of spool 46 is shaped so as to define male projections, e.g., knobs or hooks, around which respective portions of flexible member 30 are ensnared or looped and thereby coupled to spool 46.

As described hereinabove, locking mechanism 45 is coupled to lower surface 152 and is coupled, e.g., welded, at least in part to a lower surface of spool housing 1042. Typically, locking mechanism 45 defines a mechanical element having a planar surface that defines slits 58. It is to be noted that the surface of locking mechanism 45 may also be curved, and not planar. Locking mechanism 45 is shaped to provide a protrusion 156 which projects out of a plane defined by the planar surface of the mechanical element. Slits 58 define a depressible portion 128 of locking mechanism 45 that is disposed in communication with and extends toward protrusion 156. Depressible portion 128 is moveable in response to a force applied thereto typically by screwdriver head 95, as shown in detail hereinbelow with reference to FIGS. 16B-C.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

A cap 1044 is provided that is shaped to define a planar surface and an annular wall having an upper surface 244 thereof. Upper surface 244 of the annular wall is coupled to, e.g., welded to, a lower surface provided by spool housing 1042. The annular wall of cap 1044 is shaped to define a recessed portion 1144 of cap 1044 that is in alignment with recessed portion 142 of spool housing 1042. For some applications, locking mechanism 45 is not welded to housing 1042, but rather, locking mechanism 45 is held in place by cap 1044.

Figure 16B:
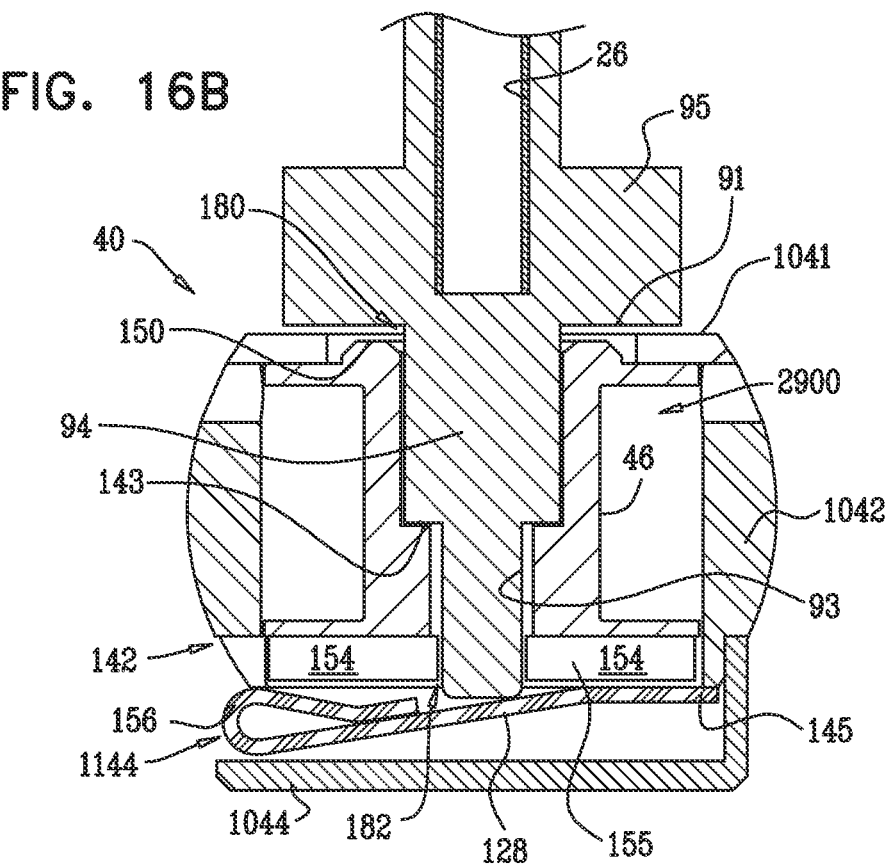
Figure 16C:
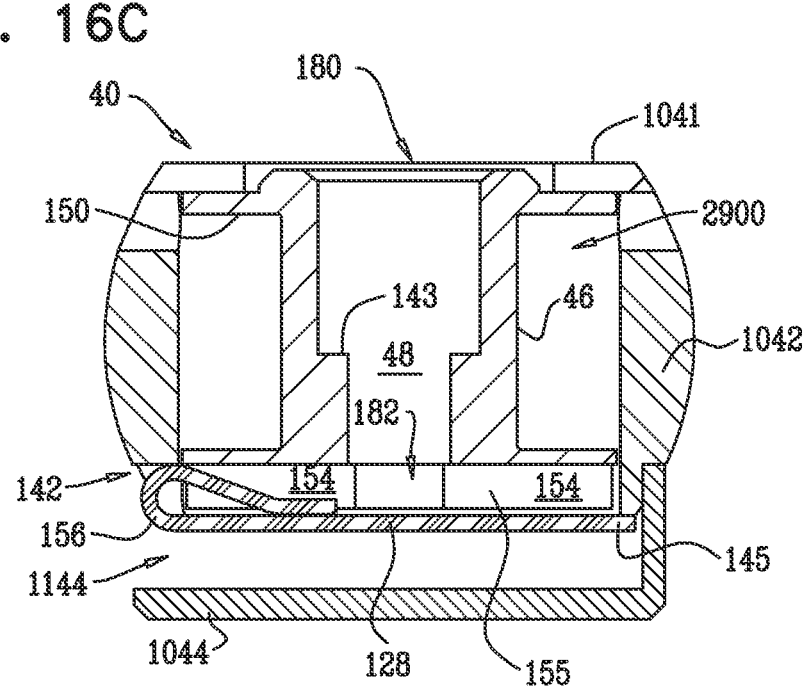

FIGS. 16B-C show adjusting mechanism 40 in respective locking states thereof, in accordance with some applications of the present invention. It is to be noted that contracting member 30 that is typically coupled to spool 46, is not shown for clarity of illustration. FIG. 16B shows adjusting mechanism 40 in an unlocked configuration in which protrusion 156 of a locking mechanism 145 is disposed within recessed portion 1144 of cap 1044. FIG. 16C shows the locked state of spool 46 by the positioning of protrusion 156 within a recess 154 of spool 46. It is to be noted that locking mechanism 145 is similar to locking mechanism 45, as described hereinabove with reference to FIGS. 1-15, with the exception that protrusion 156 and slits 58 of locking mechanism 145 are shaped differently than protrusion 56 and slit 58 of locking mechanism 45.

During (1) the delivery of the annuloplasty structure to which adjusting mechanism 40 is coupled toward the implantation site (i.e., the annulus of an atrioventricular valve), (2) the attachment of the annuloplasty structure to the implantation site, and (3) the subsequent bidirectional rotation of spool 46 to adjust the dimensions of the annuloplasty structure, adjusting mechanism 40 is disposed in an unlocked state, as shown in FIG. 16B. As shown in FIG. 16C, spool 46 is shaped to provide a first opening 180 at upper surface 150 thereof and a second opening 182 at a lower surface 152 thereof. Spool 46 defines a channel 48 that extends from first opening 180 toward second opening 182.

FIG. 16B shows adjusting mechanism 40 in an unlocked state thereof in which screwdriver head 95 is disposed within channel 48 of spool 46. Screwdriver head 95 comprises an elongate body shaped to define a proximal generally cylindrical structure and spool-rotating portion 94 which fits within channel 48 defined by spool 46. Spool-rotating portion 94 is shaped to define a distal force applicator 93 which is disposed proximally to and in communication with depressible portion 128 of locking mechanism 145. In the unlocked state of adjusting mechanism 40, screwdriver head 95 is disposed with respect to housing 1042 in a manner in which a distal end of force applicator 93 extends beyond second opening 182 of spool 46 and pushes against depressible portion 128 of locking mechanism 145. Depressible portion 128 is thus pushed downward, as shown.

Channel 48 of spool 46 is shaped to accommodate the dimensions of spool-rotating portion 94 and force application 93 of screwdriver head 95. Spool-rotating portion 94 has a width that is wider than the force applicator 93. In turn, channel 48 of spool 46 is shaped to accommodate spool-rotating portion 94 and force application 93 defining an upper portion and a lower portion thereof in which the upper portion of channel 48 is wider than the lower portion. The narrower lower portion of channel 48 ensures that force applicator 93 is not advanced distally beyond a certain point as the narrower lower portion of channel 48 restricts passage therethrough of the upper, wider portion of spool-rotating portion 94. Screwdriver head 95 is shaped to define a shelf portion 91 which rests against upper surface 1041 of spool housing 1042. Similarly, spool-rotating portion 94 is shaped to define a shelf portion 143 which rests against a horizontal wall of spool 46 which defines a portion of channel 48. During the unlocked state of adjusting mechanism 40, screwdriver head 95 is disposed in a manner in which shelf portion 91 thereof rests against upper surface 1041 of spool housing 1042, and shelf 143 of spool-rotating portion 94 rests against the horizontal wall of channel 48, as shown.

During the unlocked state of adjusting mechanism 40, depressible portion 128 is maintained in a pushed state by force applicator 93. In such a state, protrusion 156 of locking mechanism 145 is maintained in a pushed state toward the planar surface of cap 1044. It is to be noted that the surface of cap 1044 may also be curved, and not planar. As described hereinabove, cap 1044 is shaped to provide a recessed portion 1144 for receiving protrusion 156 in its pushed-down state. As depressible portion 128 is pushed downward, protrusion 156 is freed from within a recess 154 defined by structural barrier portions 155 of the lower portion of spool 46. Additionally, protrusion 156 is freed from within recessed portion 142 provided by spool housing 1042. Responsively, adjusting mechanism 40 is unlocked, and spool 46 may be rotated by screwdriver head 95 in either clockwise or counter-clockwise directions in response to torque delivered to head 95 by torque-delivering tool 26 coupled thereto. In response to the torque, spool-rotating portion 94 of screwdriver head 95 engages and pushes against the wall defining channel 48 in order to rotate spool 46.

Cap 1044 functions to restrict distal pushing of depressible portion 128 beyond a desired distance so as to inhibit deformation of locking mechanism 145. Once adjusting mechanism 40 is implanted in heart tissue, cap 1044 also provides an interface between adjusting mechanism 40 and the heart tissue. This prevents interference of heart tissue on adjusting mechanism 40 during the locking and unlocking thereof. Additionally, cap 1044 prevents damage to heart tissue by depressible portion 128 as it is pushed downward.

FIG. 16C shows adjusting mechanism 40 in a locked state thereof in which locking mechanism 145 is shown in a resting state thereof. In the resting state of locking mechanism 145, depressible portion 128 is disposed in a horizontal position (i.e., perpendicularly with respect to a longitudinal axis of channel 48) in response to removal of screwdriver head 95 from within channel 48 of spool 46. Depressible portion 128 has a tendency to assume the horizontal position, as shown, and in the absence of a downward pushing force applied to depressible portion 128 by screwdriver head 95, depressible portion 128 returns to its horizontal position from its pushed-down state, as shown in FIG. 4B. In this horizontal position, protrusion 156 of locking mechanism 145 is removed from recessed portion 1144 of cap 1044 and is returned within a recess 154 of spool 46 and thereby restricts movement of spool 46 and locks adjusting mechanism 40. Additionally, protrusion 156 of locking mechanism 145 returns in part within recessed portion 142 of spool housing 1042. Thus, recessed portion 142 of spool housing 1042 provides supplemental locking of locking mechanism 145.

Figure 17:
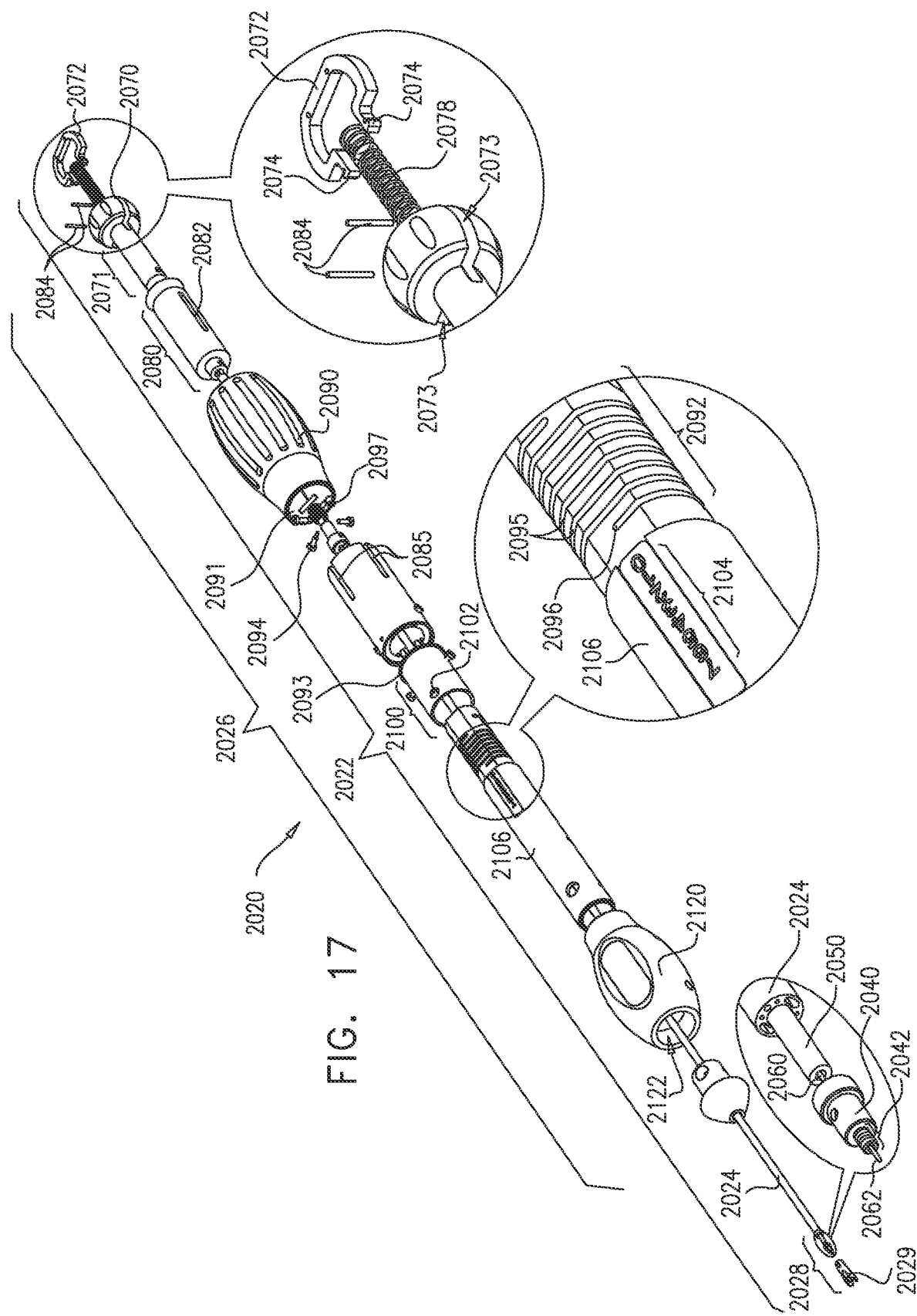
FIG. 17 is a schematic illustration of a delivery tool which facilitates rotation of a rotatable structure in an adjusting mechanism, in accordance with some applications of the present invention.
Figure 20A:
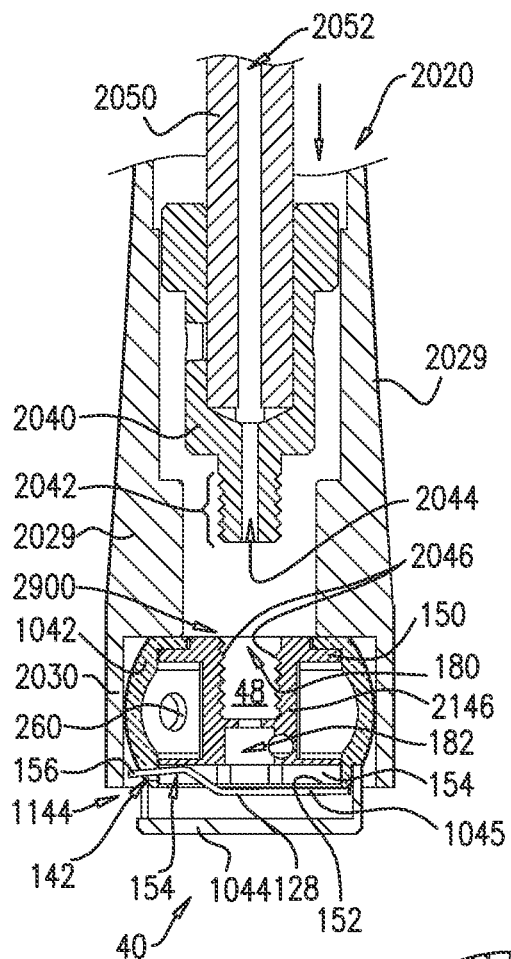
FIGS. 20A-C are schematic illustrations of respective components of the adjusting mechanism, in accordance with some applications of the present invention.
Figure 20B:
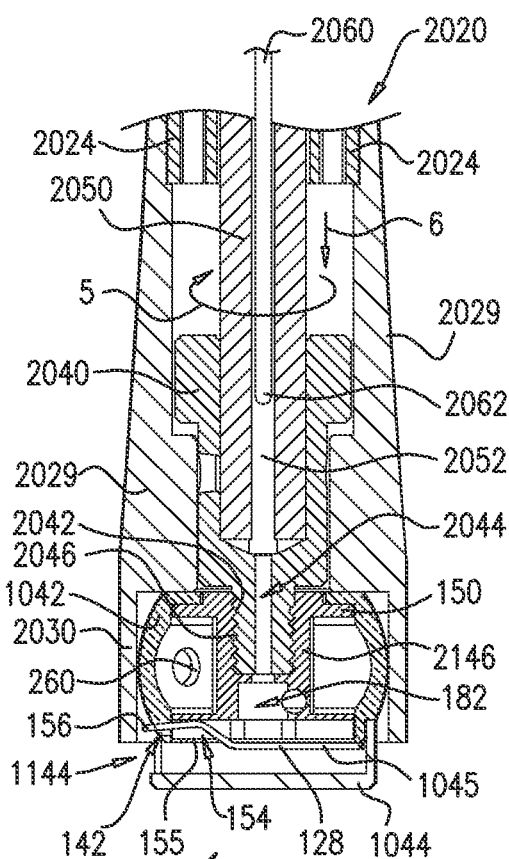
Figure 20C:
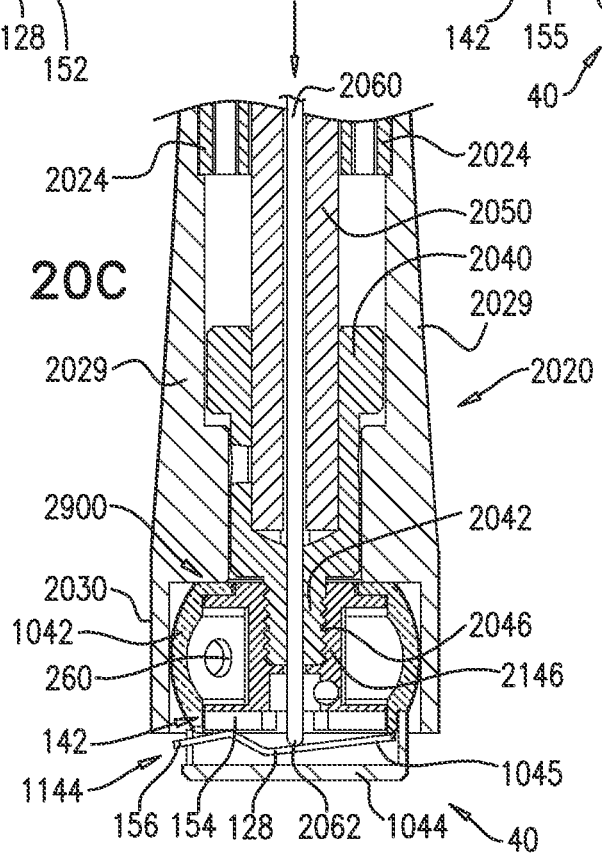

Reference is now made to FIG. 17, which is a schematic illustration of a system 2020 comprising a delivery tool 2022 for delivering an adjusting mechanism comprising a rotatable structure to tissue of a patient and facilitating rotation of rotatable structure, in accordance with some applications of the present invention. Reference is now made to FIGS. 18-19 which show delivery tool 2022 coupled at a distal portion 2028 thereof to adjusting mechanism 40 which comprises rotatable structure 2900, in accordance with some applications of the present invention. FIGS. 20A-C are schematic cross-sectional illustrations of delivery tool 2022 coupled to adjusting mechanism 40 comprising rotatable structure 2900, in accordance with some applications of the present invention.

FIG. 17 is an exploded view of tool 2022 showing the relationship of its components. Tool 2022 has an elongate shaft 2024 and a proximal handle portion 2026. For some applications, and as shown herein, shaft 2024 comprises a multilumen shaft, by way of illustration and not limitation. That is, shaft 2024 may be shaped to define only a single central lumen for passage therethrough of a torque-delivering tool 2050. Typically, shaft 2024 is sized for open-heart and/or minimally-invasive procedures and comprises a flexible material (e.g., a plastic or a plurality of strands of flexible metal such as stainless steel 304 that are bundled together) which may be bent to a desired angle. For some applications shaft 2024 is sized for transluminal, percutaneous, or endovascular, procedures for delivery of an adjusting mechanism, as described herein.

Proximal handle portion 2026 is shaped to define an ergonomic hand-grasping portion 2120 for the physician to grasp and thereby hold tool 2022. Handle portion 2026 comprises a central lumen 2122 that extends from the distal end of handle portion 2026 toward the proximal end of handle portion 2026. A proximal end portion of shaft 2024 is disposed within lumen 2122 and is thereby coupled to handle portion 2026.

A distal end portion 2028 of shaft 2024 is coupled to, e.g., welded to, an adjusting mechanism holder 2029 which comprises a housing portion 2030 for receiving and reversibly coupling adjusting mechanism 40. Holder 2029 is shaped to define a lumen for slidable passage therethrough of a manipulator 2040 which comprises a distal screwdriver head 2042. Screwdriver head 2042 is ultimately coupled to rotatable structure 2900 and facilitates rotation of rotatable structure 2900 responsively to the rotation of manipulator 2040. Manipulator 2040 is coupled at a proximal end thereof to a distal end of torque-delivering tool 2050 which delivers torque to manipulator 2040 and effects rotation of screwdriver head 2042. As is described hereinbelow, a proximal end of torque-delivering tool 2050 is coupled to the rotating mechanism at proximal handle portion 2026. Shaft 2024 is shaped to define a central lumen through which torque-delivering tool 2050 passes.

Reference is again made to FIGS. 18-19, which show distal portion 2028 of tool 2022 coupled to adjusting mechanism 40. Adjusting mechanism 40 comprises a rotatable structure housing 1042 which houses rotatable structure 2900. For some applications, rotatable structure 2900 comprises a spool 2146, by way of illustration and not limitation. It is to be noted that rotatable structure 2900 may comprise any suitable rotatable structure (e.g., a pinion of a rack and pinion, as described hereinbelow). Rotatable structure 2900 and knobs 2070 and 2090 typically rotate about a central axis 2200 of tool 2022.

Reference is now made to FIGS. 1-3, 5, 18, 24, and 25A-B, which are schematic illustrations of tool 2022 coupled to adjusting mechanism 40 which is, in turn, coupled to an annuloplasty device 1260, in accordance with respective applications of the present invention. Typically, adjusting mechanism 40 is configured for adjusting a perimeter of annuloplasty device 1260. As shown, implant 1260 comprises a full annuloplasty ring, by way of illustration and not limitation. The full annuloplasty ring may comprise annuloplasty structure 122 as described hereinabove with reference to FIG. 5. The scope of the present invention includes the use of adjusting mechanism 40 and tool 2022 in order to adjust the perimeter of any suitable annuloplasty device such as a full annuloplasty ring or a partial, or open, annuloplasty ring. The annuloplasty device may be implemented using any one of the techniques described in U.S. patent application Ser. No. 12/341,960 to Cabiri, which issued as U.S. Pat. No. 8,241,351, and which is incorporated herein by reference. Typically, these techniques describe a full or partial ring comprising a sleeve, a spool coupled to the sleeve, and a flexible longitudinal contracting member that is coupled to the spool and the sleeve, such that (1) winding the contracting member around the spool tightens the ring, and (2) unwinding the contracting member from around the spool relaxes and expands the ring. That is, during rotation of rotatable structure 2900 in a first direction, successive portions of member 30 contact spool 2146.

Reference is again made to FIGS. 1-3, 5, 15, 18, 24, and 25A-B. Housing 1042 typically comprises first and second coupling members 31 and 35 which facilitate coupling of adjusting mechanism to the annuloplasty device. For applications in which a full annuloplasty ring is adjusted by adjusting mechanism 40 (FIG. 24), coupling members 31 and 35 are coupled to first and second free ends of an annuloplasty device such that the coupling of the free ends to members 31 and 35 forms a full ring. For applications in which a partial annuloplasty device is adjusted by adjusting mechanism 40 (FIGS. 25A-B), housing 1042 comprises only one coupling member, and a first free end of the annuloplasty device is coupled to housing 1042 via the coupling member, and the second free end of the partial annuloplasty device is not coupled to housing 1042. For other applications in which a partial annuloplasty device is adjusted by adjusting mechanism 40 (e.g., structure 22, as described hereinabove with reference to FIGS. 1-3), depending on the positioning of housing 1042 with respect to the ring, comprises coupling members 31 and/or 35. That is, for applications in which the annuloplasty device comprises structure 22, as described hereinabove with reference to FIGS. 1-3, the housing of adjusting mechanism 40 comprises only coupling member 31. For applications in which the annuloplasty device comprises structure 1122, as described hereinabove with reference to FIG. 15, the housing of adjusting mechanism 40 comprises coupling members 31 and 35.

It is to be noted that adjusting mechanism 40 may be coupled to the annuloplasty device along any portion thereof. For some applications, the flexible longitudinal contracting member comprises an artificial chordea tendinea which is coupled at a first portion to the rotating member of adjusting mechanism 40 and at a second portion to a leaflet of an atrioventricular valve of the patient. In such an application, adjusting mechanism 40 functions to adjust a dimension of the artificial chordea tendinea. Such techniques for artificial chordal adjustment may be implemented using any one of the techniques described in U.S. patent application Ser. No. 12/548,991 to Maisano et al., which issued as U.S. Pat. No. 8,808,368, and which is incorporated herein by reference.

Reference is now made to FIGS. 20A-C, which are schematic illustrations of adjusting mechanism 40 comprising rotatable structure 2900. Adjusting mechanism 40 is shown as comprising housing 1042 which defines a recessed portion 142. Rotatable structure 2900 in some applications, comprises a spool 2146, as shown, to which is coupled at least a portion of a flexible longitudinal member (not shown for clarity of illustration). Rotation of the spool 2146 in a first direction winds the portions of the longitudinal member around spool 2146, while rotation of spool 2146 in a second direction opposite the first direction, unwinds the portion of the longitudinal member from around spool 2146.

Spool 2146 is disposed within housing 1042 and defines an upper surface 150, a lower surface 152 and a cylindrical body portion disposed vertically between surfaces 150 and 152. Spool 2146 is shaped to provide a driving interface, e.g., a channel 48, which extends from a first opening 180 provided by upper surface 150 to a second opening 182 provided by lower surface 152. A proximal portion of channel 48 of the driving interface is shaped to define a threaded portion 2046 which may or may not be tapered. The cylindrical body portion of spool 2146 is shaped to define one or more holes which function as respective coupling sites for coupling (e.g., looping through the one or more holes, or welding to spool 2146 in the vicinity of the one or more holes) of any number of longitudinal members (not shown for clarity of illustration) to spool 2146.

Lower surface 152 of spool 2146 is shaped to define one or more (e.g., a plurality, as shown) recesses 154 which define structural barrier portions 155 of lower surface 152. It is to be noted that any suitable number of recesses 154 may be provided, e.g., between 1 and 10 recesses, circumferentially with respect to lower surface 152 of spool 2146. It is to be noted that recesses 154 may be provided at lower surface 152 in a random pattern, and are not necessarily circumferentially oriented.

Reference is now made to FIGS. 18 and 20A-C. A locking mechanism 1045 is disposed in communication with lower surface 152 of spool 2146 and disposed in communication with at least in part to a lower surface of spool housing 1042. Typically, cap 1044 maintains locking mechanism in place with respect to lower surface 152 of spool 2146 and lower surface of spool housing 1042. For some applications, locking mechanism 1045 is coupled, e.g., welded or disposed adjacently, to the lower surface of housing 1042. Typically, locking mechanism 1045 defines a mechanical element having a planar surface that defines slits 58. It is to be noted that the surface of locking mechanism 1045 may also be curved, and not planar. Locking mechanism 1045 is shaped to provide a protrusion 156 which projects out of a plane defined by the planar surface of the mechanical element. Slits 58 (shown in the enlarged portion of FIG. 18) define a depressible portion 128 of locking mechanism 1045 that is disposed in communication with and extends toward protrusion 156. Depressible portion 128 is moveable in response to a force applied thereto typically by an elongate locking mechanism release rod 2060 which slides through a lumen 2052 of torque-delivering tool 2050, as shown in detail hereinbelow with reference to FIGS. 21A-C.

It is to be noted that the planar, mechanical element of locking mechanism 1045 is shown by way of illustration and not limitation and that any suitable mechanical element having or lacking a planar surface but shaped to define at least one protrusion may be used together with locking mechanism 1045.

A cap 1044 is provided that is shaped to define a planar surface and an annular wall having an upper surface thereof. The upper surface of the annular wall is coupled to, e.g., welded to, a lower surface provided by spool housing 1042. The annular wall of cap 1044 is shaped to define a recessed portion 1144 of cap 1044 that is in alignment with recessed portion 142 of spool housing 1042.

Reference is now made to FIG. 18. Housing 1042 surrounding spool 2146 is shown as not being coupled to cap 1044 for clarity of illustration. However, it is to be noted that housing 1042 as shown in FIG. 18 is, in fact, coupled to cap 1044, as shown in FIGS. 20A-C.

Reference is now made to FIGS. 20A-C, which are schematic illustrations of adjusting mechanism 40 in respective locking states thereof. FIG. 20C shows adjusting mechanism 40 in an unlocked configuration in which protrusion 156 of locking mechanism 1045 is disposed within recessed portion 1144 of cap 1044. FIGS. 20A-B show the locked state of spool 2146 by the positioning of protrusion 156 within a recess 154 of spool 2146.

Reference is now made to FIGS. 18, 19, 20A-C, and 21A-C. FIGS. 21A-C show tool 2022 coupled at distal portion 2028 to adjusting mechanism 40. As shown in FIG. 21A, adjusting mechanism 40 is coupled to a contracting member 30, as described hereinabove. In some applications, spool 2146 is shaped so as to define one or more holes for looping therethrough, and thereby coupling, of a portion of contracting member 30. As shown in the enlarged cross-sectional image of FIG. 20B, housing 1042 is surrounded by housing portion 2030 of adjusting mechanism holder 2029. Spool 2146 is disposed within housing 1042 and a threaded portion of screwdriver head 2042 is coupled to threaded portion 2046 of channel 48 of spool 2146. Manipulator 2040, comprising screwdriver head 2042, is coupled to the distal end of torque-delivering tool 2050. A proximal end of torque-delivering tool 2050 is coupled to a rotating mechanism in proximal handle portion 2026 of tool 2022. The rotating mechanism comprises torque-delivering rotator 2080 which is rotated at different times during a surgical procedure by knobs 2070 and 2090. Torque-delivering-tool rotator 2080 comprises a cylindrical structure which is shaped to define a lumen 2077 and an opening at a proximal end thereof. Lumen 2077 of rotator 2080 provides a slidable coupling arrangement for an elongate structural component 2071 that is coupled to knob 2070. One or more pins 2084 are coupled to a distal end of component 2071. Rotator 2080 is shaped to define one or more slits 2082 through which project respective portions of pins 2084 in order to couple component 2071 to rotator 2080. As the operating physician rotates knob 2070, structural component 2071 rotates and, since component 2071 is coupled to rotator 2080 via pins 2084, rotator 2080 rotates responsively. A distal portion of rotator 2080 is coupled to a proximal portion of torque-delivering-tool coupler 2086. Torque-delivering-tool coupler 2086 is shaped to define a lumen which houses the distal end torque-delivering tool 2050. The distal end of torque-delivering tool 2050 is typically coupled to, e.g., welded to, torque-delivering tool housing 2086. Torque-delivering tool housing 2086 rotates responsively to rotation of rotator 2080. Responsively, torque-delivering tool 2050 rotates, which, in turn, rotates screwdriver head 2042 and, in turn, rotatable structure 2900.

Prior to delivering and implanting adjusting mechanism 40, delivery tool 2022 is coupled to mechanism 40. Housing 2030 of adjusting mechanism holder 2029 surrounds housing 1042 of adjusting mechanism 40, which provides initial coupling of tool 2022 to adjusting mechanism 40. During the initial coupling, manipulator 2040 may be pushed proximally, along central axis 2200 of tool 2022, by the force of contact of adjusting mechanism 40 to tool 2022. Manipulator 2040 is coupled to a distal end of torque-delivering tool 2050, which in turn, is coupled at a proximal end thereof to torque-delivering-tool coupler 2086. Torque-delivering tool 2050 slides within a lumen provided by shaft 2024 of tool 2022. Tool 2022 enables such proximal pushing of manipulator 2040 by providing a tensile spring 2087 around torque-delivering-tool coupler 2086. As screwdriver head 2042 contacts adjusting mechanism 40, adjusting mechanism 40 responsively pushes and slides proximally (1) screwdriver head 2042 (2) manipulator 2040, (3) torque-delivering tool 2050, and (4) torque-delivering-tool coupler 2086. Responsively to the pushing of torque-delivering-tool coupler 2086, spring 2087 is compressed to enable such proximal sliding of (1) screwdriver head 2042 (2) manipulator 2040, (3) torque-delivering tool 2050, and (4) torque-delivering-tool coupler 2086.

Following the initial coupling of adjusting mechanism 40 to tool 2022, tool 2022 is then more firmly coupled to adjusting mechanism 40 by screwing screwdriver head 2042 into threaded portion 2046 of spool 2146 of adjusting mechanism 40. By the screwing, screwdriver head 2042 is advanced distally toward adjusting mechanism 40. This screwing of head 2042 is accomplished when the physician rotates knob 2070 (in the direction as indicated by arrow 1 in FIG. 4B), which, in conjunction, rotates (1) component 2071, (2) rotator 2080, (3) torque-delivering tool housing 2086, (4) torque-delivering tool 2050, and finally, (5) screwdriver head 2042 of manipulator 2040. Responsively, screwdriver head 2042 screws into threaded portion 2046 of spool 2146, and thereby, adjusting mechanism 40 is firmly coupled to tool 2022. Once tool 2022 is firmly coupled to adjusting mechanism 40, tool 2022 (1) frees spool 2146 from locking mechanism 1045, and (2) rotates spool 2146, as described hereinbelow.

Reference is now made to FIGS. 22 and 23, which are schematic illustrations of tool 2022 as it releases spool 2146 from locking mechanism 1045 and rotates spool 2146, in accordance with some applications of the present invention. Following the firm coupling of tool 2022 to adjusting mechanism 40, locking mechanism 1045 is released in order to allow for rotation of spool 2146 of adjusting mechanism 40.

Reference is now made to FIGS. 17, 19, 20A-C, 21A-C, and 22-23. Knob 2070 is shaped to define a groove 2073 (as shown in an enlarged image of knob 2070 in FIG. 17). A flexible, semi-rigid release clip 2072 is coupled to knob 2070 and is disposed within groove 2073. Clip 2072 is shaped to define male couplings 2074 at respective distal ends of clip 2072. Couplings 2074 function to lock knob 2070 with respect to handle 2026 during a pushed state of knob 2070. FIGS. 21A-B show knob 2070 in a resting state thereof, prior to the pushing of knob 2070 along central axis 2200 of tool 2022, in which a proximal portion of component 2071 is exposed proximal to lumen 2077 of rotator 2080, couplings 2074 are disposed proximally to the opening of rotator 2080, and pins 2084 are disposed in a proximal position within slits 2082 of rotator 2080. FIG. 21C shows knob 2070 in a pushed state in which the proximal portion of component 2071 is disposed within lumen 2077 of rotator 2080, a distal portion of clip 2072 is disposed within a proximal portion of lumen 2077 of rotator 2080, and male couplings 2074 are disposed, and locked in place within respective female couplings 2081 of rotator 2080. The coupling of male and female couplings 2074 and 2081 enable knob 2070 to remain in a locked position.

The pushing distally of knob 2070 compresses and applies load to a tension spring 2078 that is disposed within knob 2070 and component 2071. As shown in the enlarged image of FIG. 21C, a proximal end of elongate locking mechanism release rod 2060, is coupled to release rod holder 2061, which, in turn, is coupled to component 2071. Pushing distally of knob 2070 (and thereby component 2071) advances holder 2061 distally, which, in turn, pushes distally release rod 2060. Release rod 2060 extends through tool 2022 from handle 2026 and toward distal portion 2028 of tool 2022, and is surrounded, for the most part, by torque-delivering tool 2050. During a resting state of tool 2022 (i.e., when knob 2070 is not pushed distally), a distal end of rod 2060 is disposed within torque-delivering tool 2050 proximally to and does not engage adjusting mechanism 40.

It is to be noted that in order to release locking mechanism 1045 from spool 2146, protrusion 156 should be pushed distally by rod 2060 between 0.3 and 1.0 mm, e.g., 0.4 mm. When tool 2022 is decoupled from adjusting mechanism 40 and knob 2070 is disposed in a pushed state, the distal end portion of rod 2060 extends approximately 5 mm beyond the distal end of tool 2022. When adjusting mechanism 40 is coupled to tool 2022, and rod 2060 is pushed distally, distal end 2062 of rod 2060 contacts and is impeded by depressible portion 128 of locking mechanism 1045. Depressible portion 128 is capable of being depressed by an angle of up to 20 degrees, e.g., 7 degrees (i.e., cap 1044 restricts depressing of portion 128 beyond a certain angle). When the distal portion of rod 2060 contacts depressible portion 128, portion 128 restricts rod 2060 from extending further than 1 mm from second opening 182 of spool 2146. In order to compensate for the restricting of the extension of rod 2060 beyond a predetermined amount, spring 2078 contracts in order to slightly pull back rod 2060. Spring 2078 thus enables tool 2022 to be generally exacting in pushing protrusion 156 distally by 0.3-0.5, e.g., 0.4 mm.

Reference is again made to FIGS. 20B-C and 22. In response to the pushing of knob 2070 distally (i.e., in the direction as indicated by arrow 6), release rod 2060 slides distally within lumen 2052 of torque-delivering tool 2050 such that a distal portion of rod 2060 slides through lumen 2044 of manipulator 2040 (lumens 2052 and 2044 are shown in the enlarged image of FIG. 20B), through screwdriver head 2042, and then through channel 48 of spool 2146. A distal end 2062 of rod 2060 advances beyond the opening provided by lower surface 152 of spool 2146, and presses distally on depressible portion 128 of locking mechanism 1045. Since depressible portion 128 is connected to protrusion 156, pushing distally on depressible portion 128 pushes protrusion 156 distally from within recess 154 of spool 2146, thereby freeing spool 2146 from locking mechanism 1045 (as shown in FIG. 20C and in the enlarged image of FIG. 22). As protrusion 156 is pushed, it advances distally within recessed portion 1144 of cap 1044 and within recessed portion 142 of housing 1042.

It is to be noted that any elongate structure, e.g., a pull-wire, a rod, a thread, rope, or a suture, may be passed through lumen 2052 of torque-delivering tool 2050 independently of and/or in addition to rod 2060. It is to be noted that any elongate structure, e.g., a pull-wire, a rod, a thread, rope, or a suture, may be passed through the lumen of shaft 2024 independently of and/or in addition to tool 2050.

Typically, tool 2050 comprises a flexible material (e.g., a plastic or a plurality of strands of flexible metal such as stainless steel 304 that are bundled together). Once protrusion is displaced from within recess 154 of spool 2146, and spool 2146 is released from locking mechanism 1045, the physician rotates knob 2090 in a first direction thereof, as indicated by arrow 7, in order to rotate spool 2146, as described hereinbelow. The spool is free to rotate in either clockwise or counterclockwise direction, as long as protrusion 156 of locking mechanism 1045 is decoupled from spool 2146. The physician is able to freely rotate knob 2090 (and thereby spool 2146) without any obstruction from locking mechanism 1045 because locking mechanism 1045 is kept in an unlocked state (i.e., protrusion 156 remains outside of the recesses 154 of spool 2146) due to the pushed state of tool 2022. During this pushed state, knob 2070 is maintained in a pushed state as male couplings 2074 are coupled to female couplings 2081, and rod 2060 is maintained in a state in which distal end 2062 is disposed distally to the opening provided by lower surface 152 of spool 2146 and pushes on depressible portion 128 of locking mechanism 1045, as shown in the enlarged image of FIG. 22.

Reference is now made to FIGS. 17, 18, 21A-C, and 22. As described hereinabove, the pushing distally and locking in place of knob 2070 releases locking mechanism 1045 from spool 2146. Additionally, the pushing distally of knob 2070 engages the rotating mechanism of tool 2022 (which comprises rotator 2080 and torque-delivering-tool coupler 2086) with knob 2090. In a resting state of tool 2022, as shown in FIG. 18, knob 2070 is disposed in its proximal-most position and pins 2084 are disposed within slits 2082 of rotator 2080 proximally to knob 2090. As shown in FIGS. 21A-C, knob 2090 is shaped to define slits 2085 along respective portions of the inner wall thereof that defines a lumen in which a distal portion of rotator 2080 is disposed.

Slits 2082 of rotator 2080 enable slidable advancement of pins 2084 during the distal sliding of component 2071 within lumen 2077 of rotator 2080 responsively to pushing distally knob 2070. During the resting state of tool 2022, as shown in FIGS. 18 and 21A-B, knob 2070 is not pushed and a proximal portion of component 2071 is exposed from within lumen 2077 of rotator 2080. Pins 2084 are disposed proximally to knob 2090, as shown in the enlarged image of FIG. 18. During the pushed state of knob 2070, pins slide distally along slits 2082 of rotator 2080 and along slits 2085 of knob 2090.

Sections A-A and B-B of FIG. 21A show slits 2085 of knob 2090 and how pins 2084 pass through slits 2085 of knob 2090. As shown in the cross-section, knob 2090 is shaped to define 4 slits 2085 by way of illustration and not limitation. That is knob 2090 may be shaped to define two slits 2085 or one slit 2085. Prior to pushing distally of knob 2070, pins 2084 are disposed proximally to the proximal ends of respective slits 2085. In order to engage pins 2084 with respective slits 2085, the physician may need to rotate knob 2070, e.g., by 30 degrees. This engaging of pins 2084 within slits 2085 further couples knob 2090 to rotator 2080. It is to be further noted that tool 2022 comprises two pins 2084 by way of illustration and not limitation, and that any suitable number of pins 2084 may be coupled to tool 2022 in accordance with the number of slits 2085. For example, if tool 2022 has 4 slits, as shown, tool 2022 may comprise between 1 and 4 pins 2084.

Since knob 2090 is coupled to rotator 2080, (and spool 2146 is now freed from locking mechanism due to the pushed state of knob 2070, as described hereinabove) rotation of knob 2090 in a first direction thereof (as indicated by arrow 7 in FIG. 22), rotates spool 2146 in the first direction. For applications in which spool 2146 is coupled to contracting member 30, as shown in FIG. 21A, rotation of spool 2146 in the first direction winds contracting member 30 around spool 2146. Once freed from locking mechanism 1045, manipulator 2040 of tool 2022 can rotate spool 2146 bidirectionally. Rotation of knob 2090 in a direction opposite the first direction rotates spool 2146 in the opposite direction and unwinds contracting member 30 from around spool 2146.

Reference is now made to FIGS. 17, 21C, and 22. Tool 2022 is shaped to define a helical groove 2092 that is shaped to define an indented track 2095. As described hereinabove, knob 2090 is coupled to the rotation mechanism of tool 2022, i.e., to rotator 2080 following the pushing of knob 2070 and the concurrent engaging and locking in place of pins 2084 with slits 2085 of knob 2090 (as shown in FIG. 21C). Knob 2090 is coupled at a distal end thereof to a tiered, or terraced, screw 2094, as shown in FIG. 21A. A narrow end portion of screw 2094 is disposed within a portion of track 2095 and is helically advanceable distally and proximally responsively to rotation of knob 2090. FIGS. 21C and 22 show tool 2022 prior to rotation of knob 2090 in the first direction (as indicated by arrow 7 in FIG. 22) in which screw 2094 is disposed in a proximal portion of track 2095 of helical groove 2092.

Knob 2090 is coupled at a distal end 2091 thereof to a sliding indicator 2100 which is shaped to define a window 2102. Rotation of knob 2090 in the first direction (as indicated by arrow 7 in FIG. 22) helically advances screw 2094 distally. This motion pushes distally sliding indicator 2100. Sliding indicator 2100 slides distally and proximally along a cylindrical body component 2106 responsively to rotation of knob 2090 in first and second directions, respectively. Component 2106 displays a series of numerical indicators 2104. As indicator 2100 slides along component 2106, window 2102 displays one or a portion of one or more numbers of indicators 2104, in order to indicate the number of rotations of spool 2146. Typically, in a resting state of tool 2022, indicator 2100 is disposed at a proximal-most position in which window 2102 displays the first number in the series of indicators 2104.

Typically, adjusting mechanism 40 is coupled to an annuloplasty device, as described herein (specifically with reference to FIGS. 24 and 25A-B, in accordance with some applications of the present invention), and tool 2022 is configured to indicate the number of rotations of spool 2146 (i.e., the number of times contracting member 30 winds around spool 2146) which corresponds to the contraction of device 1260, when knob 2090 is rotated in a first direction thereof (as indicated by arrow 7 in FIG. 22). That is, in such applications, numerical indicators 2104 may comprise the range of sizes of the valve, e.g., between 24 and 40 by way of illustration and not limitation. Generally, for applications in which numerical indicators range between 1-7, as shown, these numbers correlate to the range of sizes of the valve, e.g., between 24 and 40.

Reference is now made to FIGS. 17 and 22. The proximal annular portion of sliding indicator 2100 is shaped so as to define a plurality of teeth 2093. Knob 2090 is coupled to and houses at a distal end 2091 thereof a plunger 2097 (shown in FIG. 17). As knob 2090 is rotated, plunger 2097 rotates along teeth 2093 of the proximal annular portion of indicator 2100 and thereby provides an audible indication of the number of times the physician rotates knob 2090. For embodiments in which adjusting mechanism 40 is coupled to an adjustable annuloplasty device (as described hereinbelow), the device comprises a compressible element which has a tendency to passively expand as it is being actively contracted by adjusting mechanism 40. In order to counter the tendency of the compressible element of the annuloplasty device to expand, plunger 2097 prevents this expansion by providing a resistive force to knob 2090 as it advances along teeth 2093.

Reference is now made to FIG. 23, which is a schematic illustration of tool 2022 following rotation of knob 2090, in accordance with some applications of the present invention. As described hereinabove, knob 2090 is rotated in the first direction in order to helically advance screw 2094 distally along track 2095 of helical groove 2092.

Reference is now made to FIGS. 17, 21C and 23. Helical groove 2092 is shaped to define a certain number of rotations (e.g., 7, as shown by way of illustration and not limitation in the figures). A distal end 2096 of groove 2092 (shown in FIG. 17) provides a termination point at which screw 2094 is restricted from being advanced further distally, and rotation of knob 2090 in the first direction is thereby restricted. Restriction of rotation of knob 2090 beyond a predetermined point restricts rotation of spool 2146 beyond a predetermined amount of rotations, e.g., 7 as shown by way of illustration and not limitation. It is to be noted that because knob 2070 is also coupled to rotator 2080, rotation of knob 2070 also facilitates rotation of spool 2146. However, rotation of spool 2146 via knob 2070 does not rotate screw 2094 along groove 2092, and thereby rotation of spool 2146 is not restricted nor indicated by indicator 2100. Alternatively, rotation of spool 2146 using knob 2090 is (1) eventually restricted by the distal end of groove 2092, and (2) indicated by sliding indicator 2100.

As knob 2090 is rotated, it advances together with indicator 2100 distally along body component 2106 of tool 2022.

Following rotation of spool 2146 responsively to the rotation of knob 2090, screw 2094 is disposed at a distal end of groove 2092 (e.g., near or at distal end 2096 of groove 2092), and indicator 2100 is disposed at a distal position in which window 2102 approaches the distal-most number (i.e., number 7) in the series of numerical indicators 2104, indicating (1) that spool 2146 has been rotated about 7 times, (2) that contracting member 30 has been wound around spool 2146 about 7 times, and/or (3) the level of contraction of the annuloplasty device that is coupled to adjusting mechanism 40 in some applications.

Reference is now made to FIGS. 17, 22, and 23. Rotation of knob 2090 in the first direction (as indicated by arrow 7 in FIG. 22), and thereby spool 2146, winds a portion of contracting member 30 around spool 2146, (as shown in the enlarged cross-sectional image of FIG. 23). As described herein, rotation of knob 2090 in the second direction opposite the first direction advances screw 2094 proximally along groove 2092, and rotates spool 2146 in the second direction thereof. Winding of spool 2146 in the second direction unwinds the portion of contracting member 30 from around spool 2146 in accordance with the number of rotations of knob 2090 in the second direction.

Reference is again made to FIGS. 21C and 23. Following rotation of spool 2146, tool 2022 is decoupled from adjusting mechanism 40. FIG. 21C shows knob 2070 in a pushed state in which male couplings 2074 of clip 2072 are locking in place within female couplings 2081 of rotator 2080 (shown in the enlarged cross-sectional image of FIG. 21C). Additionally, in the pushed state of knob 2070, spring 2078 is compressed. In order to lock spool 2146 in place following rotation of spool 2146 following a desired level of rotation of spool 2146 (and in some applications, a desired level of contraction of an annuloplasty device, as described hereinbelow with reference to FIGS. 24 and 15A-B), the operating physician pushes inwardly the lateral portions of clip 2072 coupled to knob 2070 in order to release knob 2070 from its pushed state (FIG. 23). Male couplings 2074 of clip 2072 are pushed inwardly as the lateral portions of clip 2072 are pushed toward the central axis of tool 2022. This pushing of male couplings 2074 inwardly frees male couplings 2074 from within respective female couplings 2081 (shown in FIG. 21C). Responsively, spring 2078 expands from its compressed state, and knob 2070 is pushed proximally (in the direction as indicated by arrow 8 in FIG. 23) in response to the force of spring 2078. As spring 2078 expands, it pulls proximally release rod holder 2061 and release rod 2060 coupled thereto. As rod 2060 is pulled proximally, it slides proximally within lumen 2052 of torque-delivering tool 2050 such that distal end 2062 of rod 2060 no longer pushed distally depressible portion 128 of locking mechanism 1045 (as shown in the enlarged cross-sectional image of FIG. 23). Responsively to the retracting proximally of rod 2060, depressible portion 128 returns to its resting state and thereby returns protrusion 156 into one of the recesses 154 of spool 2146 and back into (1) recessed portion 1144 of cap 1044, and (2) recessed portion 142 of housing 1042. Once protrusion 156 is placed in recess 154 of spool 2146, spool 2146 is locked in place by locking mechanism 1045 and is restricted from being rotated by tool 2022.

In order to release knob 2070, the physician pushes inwardly the lateral portions of clip 2072 and knob 2070 is responsively pushed proximally from the proximal end of knob 2090 by expansion of spring 2078. As knob 2070 advances proximally, component 2071 that is coupled to knob 2070 slides proximally within lumen 2077 of rotator 2080 and pins 2084 slide proximally along slits 2082 of rotator 2080 and along slits 2085 of knob 2090.

The physician then rotates knob 2070 in the direction as indicated by arrow 9 in FIG. 23 (i.e., the direction opposite the direction as indicated by arrow 5 in FIG. 20B) in order to unscrew screwdriver head 2042 from threaded portion 2046 of spool 2146. Unscrewing screwdriver head 2042 from spool 2146 decouples manipulator 2040 from spool 2146. The physician then pulls proximally tool 2022 in order to release housing 1042 of adjusting mechanism 40 from within housing portion 2030 of adjusting mechanism holder 2029, and thereby decouple tool 2022 from adjusting mechanism 40.

Figure 24:
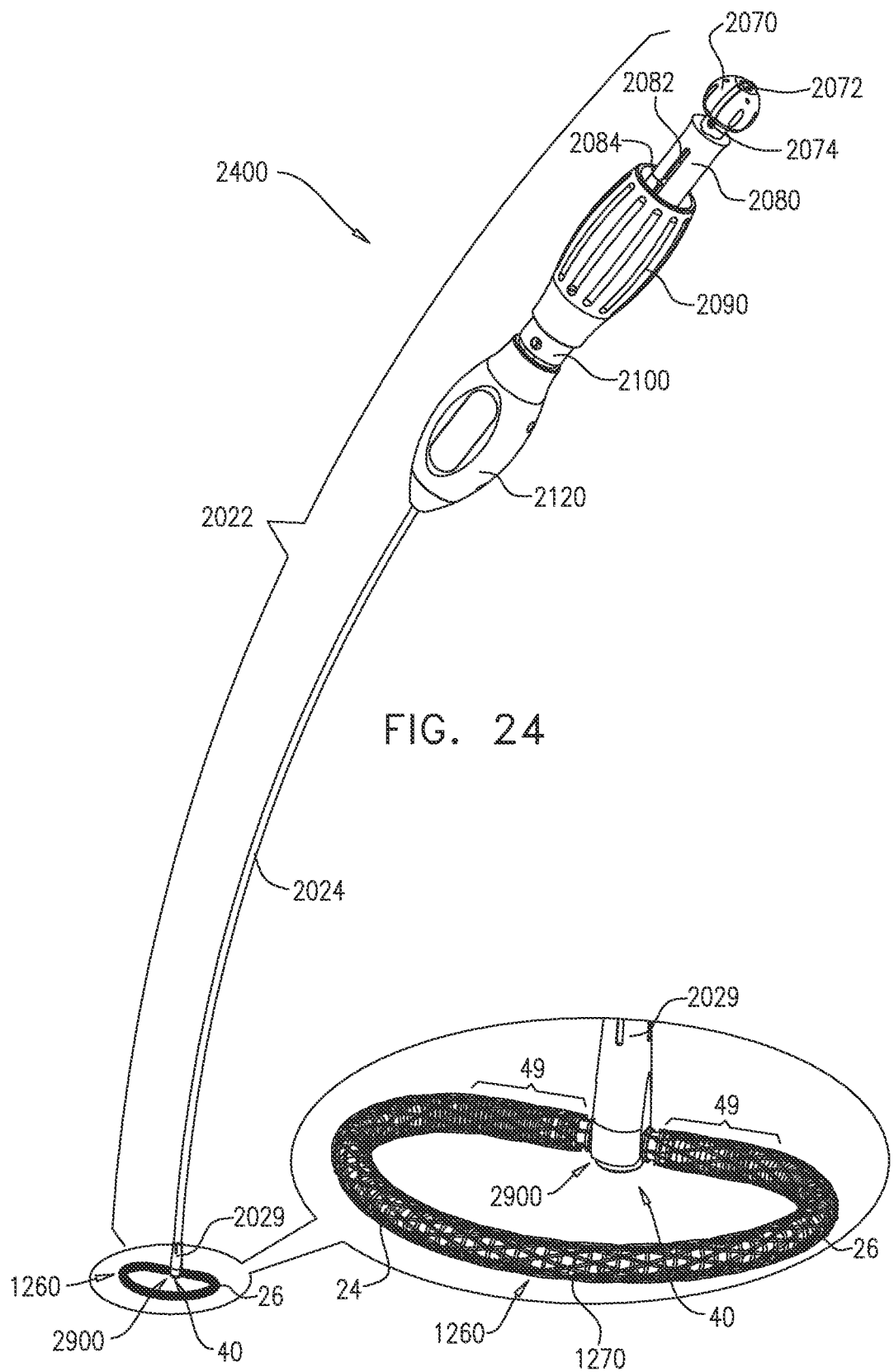
FIG. 24 is a schematic illustration of the delivery tool of FIG. 1 coupled to the adjusting mechanism which is, in turn, coupled to and facilitates adjustment of an annuloplasty device, in accordance with some applications of the present invention.
Figure 25A:
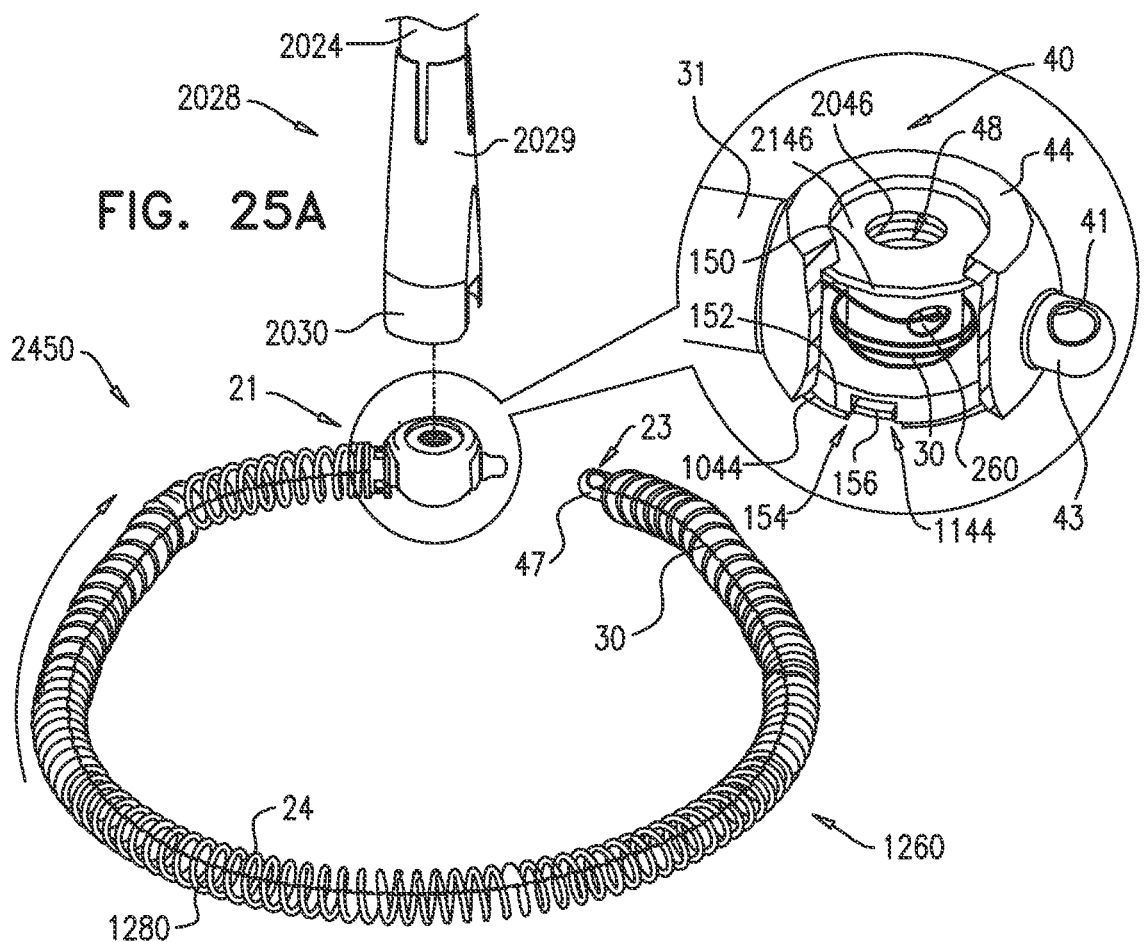
FIGS. 25A-B are schematic illustrations of the delivery tool of FIG. 1 coupled to the adjusting mechanism which is, in turn, coupled to and facilitates adjustment of an annuloplasty device, in accordance with some other applications of the present invention.
Figure 25B:
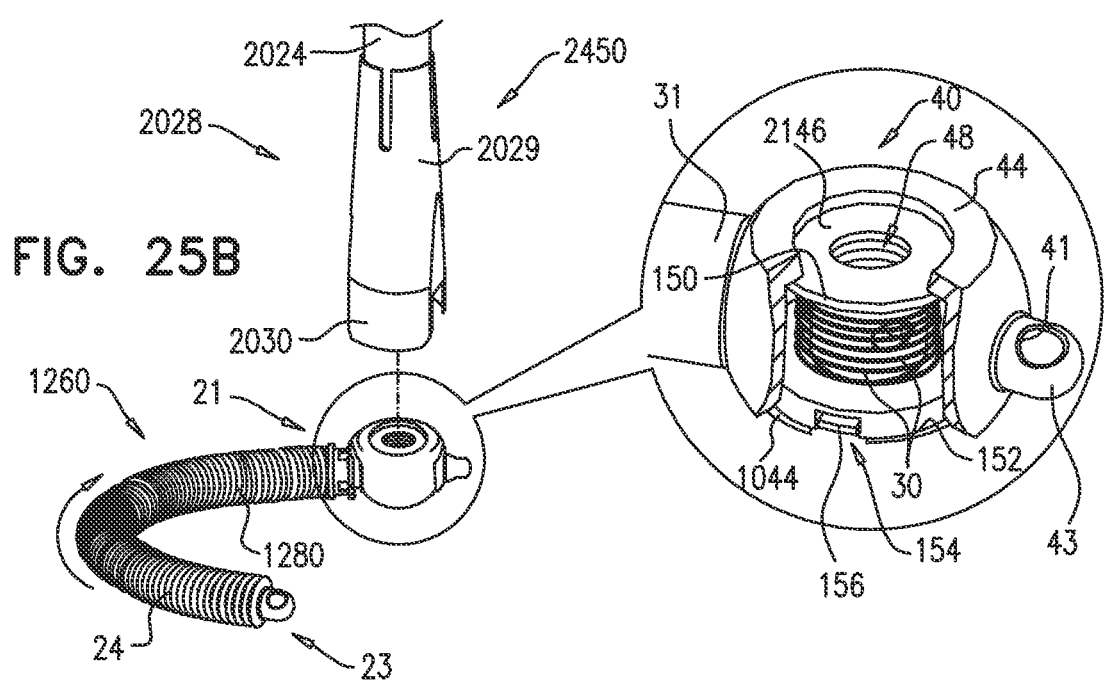

Reference is now made to FIGS. 1-3, 5, 15, 24, and 25A-B, which are schematic illustrations of systems 2400 and 2450 for repairing a dilated annulus of a patient comprising an implant structure, e.g., annuloplasty device 1260, comprising a body portion 24, flexible contracting member 30, and adjusting mechanism 40, in accordance with some applications of the present invention. FIG. 24 shows device 1260 comprising a full annuloplasty ring 1270 (e.g., for some applications, ring 1270 comprises annuloplasty structure 122, as described hereinabove with reference to FIG. 5). FIGS. 25A-B show device 1260 comprising a partial, open, or non-continuous annuloplasty ring 1280 (e.g., for some applications, ring 1280 comprises one or more annuloplasty structures 22, as described hereinabove with reference to FIGS. 1-3 and 15). At least a portion, e.g., the entirety, of body portion 24 comprises a compressible material, e.g., a coiled element, as shown by way of illustration and not limitation. For example, body portion 24 may comprise stent-like struts, or a braided mesh. Typically, body portion 24 defines a lumen along the longitudinal axis of device 1260 which houses contracting member 30. Contracting member 30 comprises a wire, a ribbon, a rope, or a band, comprising a flexible metal.

Typically, body portion 24 comprises a biocompatible material, e.g., nitinol, stainless steel, platinum iridium, titanium, expanded polytetrafluoroethylene (ePTFE), or cobalt chrome. In some applications, body portion 24 is coated with PTFE (Polytetrafluoroethylene). In some applications, body portion 24 comprises accordion-like compressible structures which facilitate proper cinching of the annulus when device 1260 is contracted. Body portion 24, when compressed, e.g., typically along a longitudinal axis of device 1260, enables portions of annuloplasty device 1260 to contract and independently conform to the configuration of the annulus of the mitral valve of a given subject. Thus, the compressible element of body portion 24 facilitates contraction of the annulus in response to contraction of device 1260.

Typically, contracting member 30 comprises a flexible and/or superelastic material, e.g., nitinol, polyester, stainless steel, or cobalt chrome, and is configured to reside chronically within device 1260. In some applications, contracting member 30 comprises a braided polyester suture (e.g., Ticron). In some applications, contracting member 30 is coated with polytetrafluoroethylene (PTFE). In some applications, contracting member 30 comprises a plurality of wires that are intertwined to form a rope structure.

As shown in FIG. 25A, spool 2146 has a cylindrical body that is disposed perpendicularly with respect to the longitudinal axis of device 1260. Spool 2146 is shaped to define one or more holes 260 for coupling of the first end of contracting member 30 thereto and, thereby, to adjusting mechanism 40. Spool 2146 is shaped to define a channel 48 which extends through the cylindrical portion of spool 2146 from an opening provided by upper surface 150 of spool 2146 to an opening provided by a lower surface 152 of spool 2146. Channel 48 provides a lumen which is disposed along an axis that is perpendicular to the longitudinal axis of device 1260 in its elongate, linear configuration. As described herein, screwdriver head 2042 engages spool 2146 via threaded portion 2046 of channel 48 and rotates spool 2146 in response to a rotational force applied to screwdriver head 2042. The rotational force applied to the screwdriver rotates spool 2146 via the portion of the screwdriver that is disposed within channel 48 of spool 2146.

FIG. 24 shows a system 2400 in which tool 2022 is coupled to annuloplasty device 1260. Typically, for such an application, tool 2022 is used for open-heart or minimally-invasive procedures, and shaft 2024 comprises a flexible material as described hereinabove, that enables shaft 2024 to conform to a desired angle when shaft 2024 is bent by the operating physician. As shown, device 1260 comprises a penetrable sleeve comprising a braided fabric mesh 26. Device 1260 may also comprise a coiled implant in addition to or independently of the sleeve. Ring 1270 comprises a compressible portion 24 and less compressible portions 49. This less compressible portion is designated for implantation between the trigones of the heart of the patient. The portion of tissue between the trigones typically does not contract as much as other portions of tissue of the annulus of the valve. Less compressible portions 49 help minimize the amount of contracting of the ring in areas of the annulus which do not lend themselves to being tightened anyway.

A first area of ring 1270 (i.e., a first end of portion 24 that is coupled to adjusting mechanism 40) comprises a first swivel snap which is coupled to coupling member 31 of housing 1042, and thereby couples a first end of body portion 24 to adjusting mechanism 40. A second area of ring 1270 (i.e., a second end of portion 24 that is coupled to adjusting mechanism 40) comprises a second swivel snap which is coupled to coupling member 35 of housing 1042, and thereby couples a second end of body portion 24 to adjusting mechanism 40. Typically, (1) the first end of body portion 24 is welded to the first snap, and the first snap is loosely coupled to coupling member 31, and (2) the second end of body portion 24 is welded to the second snap, and the second snap is loosely coupled to coupling member 35. This configuration enables swiveling of adjusting mechanism 40 with respect to ring 1270, e.g., while ring 1270 remains stationary.

FIG. 25A shows ring 1280 in a semi-contracted state thereof in which ring 1280 is contracted from a linear, elongate state having a longitudinal axis thereof. Contracting member 30 is coupled at a first end thereof to adjusting mechanism 40 which is coupled to a first end 21 of ring 1280. A second end of contracting member 30 is coupled to a second end 23 of ring 1280. Typically, during the resting state, contracting member 30 is disposed in parallel with the longitudinal axis of structure 1280.

FIG. 25A shows partial contraction of ring 1280 in response to a rotational force applied to spool 2146. In response to the rotational force, a portion of contracting member 30 is wrapped around spool 2146, as shown in the enlarged image of FIG. 25A. As contracting member 30 is wrapped around spool 2146, the second end of member 30 is pulled toward adjusting mechanism 40 in the direction as indicated by the arrow. Pulling the second end of contracting member 30 toward mechanism 40 pulls second end 23 of ring 1280 toward first end 21 of device 1260, in the direction as indicated by the arrow. Responsively, the compressible element of body portion 24 is longitudinally compressed, thereby contracting device 1260.

In some applications, the contracting of device 1260 enables device 1260 to assume the configuration shown. Alternatively, or additionally, prior to contraction, device 1260 is anchored, or otherwise fastened, at least in part to the annulus of the valve of the subject at respective locations along device 1260. The anchoring, or otherwise fastening, of device 1260 to the annulus enables device 1260 to assume the configuration shown, as described hereinbelow.

FIG. 25B shows further contraction of device 1260 in response to continued rotation of spool 2146. As shown in the enlarged image of FIG. 25B, a larger portion of contracting member 30 is wrapped around spool 2146 (i.e., member 30 is looped many times around element 46), as compared with the portion of contracting member 30 that is wrapped around spool 2146 (as shown in the enlarged image of FIG. 25A). Responsively to the wrapping of contracting member 30 around spool 2146, the compressible element of body portion 24 is further longitudinally compressed, and device 1260 is further contracted. As such, device 1260 provides adjustable partial annuloplasty ring 1280.

Reference is now made to FIGS. 25A-B. First end 21 of ring 1280 comprises a swivel snap which is coupled to coupling member 31 of housing 1042 and thereby couples a first end of body portion 24 to adjusting mechanism 40. Typically, the first end of body portion 24 is welded to the snap, and the snap is loosely coupled to coupling member 31 so as to enable swiveling of adjusting mechanism 40 with respect to ring 1280, e.g., while ring 1280 remains stationary. Adjusting mechanism 40 is coupled to a first suture fastener 41 that is shaped to define a hole 43 for passage therethrough of a suture. Second end 23 of ring 1280 comprises a second suture fastener 37 that is shaped to define a hole 47 for passage therethrough of a suture. Second end 23 of ring 1280 comprises a coupling member 33 which couples a second end of body portion 24 to suture fastener 37. Typically, the second end of body portion 24 is welded to coupling member 33. Applications as described herein with reference to FIGS. 25A-B also apply to applications described herein with reference to FIGS. 1-3 and 15.

Reference is again made to FIGS. 24 and 25A-C. It is to be noted that the winding of member 30 around spool 2146, as shown in FIGS. 25A-B applies also to the mode of operation of adjusting mechanism 40 of FIG. 24. Techniques and devices described herein may be practiced in combination with techniques and devices comprise any device as described in U.S. patent application Ser. No. 12/341,960 to Cabiri, entitled "Adjustable partial annuloplasty ring and mechanism therefor," filed on Dec. 22, 2008, which issued as U.S. Pat. No. 8,241,351, and which is incorporated herein by reference.

Reference is now made to FIGS. 20A-C, 24, and 25A-B. Adjusting mechanism 40 (and thereby device 1260) is first coupled to tool 2022, as described hereinabove. That is, first knob 2070 is rotated in order to screw screwdriver head 2042 into threaded portion 2046 of spool 2146, and then knob 2070 is pushed distally in order to release protrusion 156 of locking mechanism 1045 from spool 2146. For some applications, tool 2022 places device 1260 on the annulus and device 1260 is then sutured or anchored to the annulus. For other applications, a plurality of sutures are first sutured to the annulus. The plurality of sutures are then threaded through mesh 26 of device 1260 and device 1260 is then slid toward the annulus along the plurality of sutures. Once device 1260 is positioned on the annulus, the sutures are locked in place or tied proximally to device 1260, and then the sutures are clipped. Following the suturing or anchoring of device 1260 to the annulus, the heart is closed around shaft 2024 of tool 2022, e.g., using a purse-string stitch, and the patient is removed from the cardiopulmonary bypass pump. As the heart is beating, the operating physician rotates knob 2090 in order to rotate spool 2146 in a first direction thereof (as described hereinabove) in order to wind a portion of contracting member 30 around spool 2146. It is to be noted, and as described herein, rotation of spool 2146 may also be accomplished by rotation of knob 2070. In such a case, indicator 2100 will not be advanced in accordance with rotation of knob 2070 (i.e., because it is typically advanced as knob 2090 is rotated) and will thus not indicate the number of times contracting member 30 winds around spool 2146 or the level of contraction of device 1260.

Once tool 2022 is disengaged from adjusting mechanism 40 following the adjusting of the dimension of the annuloplasty device, and thereby of the annulus of the valve, tool 2022 is extracted from the heart. Holder 2029 is shaped so as to define a cone-shaped proximal portion which acts as an obturator to enlarge the opening surrounded by the purse-string stitch. This shape enables ease and atraumatic extracting of distal portion 2028 of tool 2022. Following the extracting of tool 2022, the opening in the heart is closed, e.g., sutured, and the access site to the body of the patient is sutured.

Reference is now made to FIG. 26, which is a schematic illustration of a system 2500 comprising a first flexible portion 813 of an implant structure that is shaped so as to define a rack 814, in accordance with some applications of the present invention. In such an application, flexile contracting member 30 comprises first flexible portion 813. In such applications, rotatable structure 2900 of adjusting mechanism 40 comprises a pinion 812. Geared teeth of pinion 812 matingly engage a plurality of engaging element, e.g., teeth, of rack 814, such that first portion 813 passes between rotatable structure 2900 and a second rotatable structure 816 that rotates on an axel 818 that is coupled to a second portion 820 of the implant structure. Pinion 812 and second rotatable structure 816 are maintained at an appropriate distance from each other using a housing or bracket (not shown, for clarity of illustration). For example, the housing or bracket may connect the axels of the rotatable structures on the sides thereof.

Reference is now made to FIGS. 17, 18, 21A-C, 22, and 26. Pinion 812 is shaped so as to define a channel having a proximal threaded portion (similarly to channel 48 of spools 46 and 2146, as described hereinabove). The distal portion of pinion is coupled to locking mechanism 1045, as described hereinabove with reference to spools 46 and 2146 being coupled to locking mechanism 1045. Adjusting mechanism holder 2029 of tool 2022 is coupled to pinion 812 or to a housing surrounding pinion 812. Screwdriver head 2042 engages pinion 812 in a manner similar to the engaging of spool 2146 by screwdriver head 2042. That is, screwdriver head 2042 is screwed into the proximal portion of pinion 812 responsively to the rotation of knob 2070. Subsequently, pinion 812 is released from locking mechanism 1045 responsively to the pushed state of knob 2070, as described hereinabove. Rotation of knob 2090 in the first direction (as indicated by arrow 7 in FIG. 22) facilitates rotation of pinion 812 in the first direction enables first portion 813 to pass between pinion 812 and second rotatable structure 816 in a first linear direction. Once freed from locking mechanism 1045, manipulator 2040 of tool 2022 can rotate spool 2146 bidirectionally. Rotation of knob 2090 in a direction opposite the first direction rotates pinion 812 in the opposite direction and, thereby, first portion 813 passes between pinion 812 and second rotatable structure 816 in a second linear direction opposite the first linear direction.

Reference is now made to FIGS. 1, 5, 15, and 26. For applications in which the implant structure comprises a full band, such as a full annuloplasty ring (as shown in FIG. 5), the first and second portions 813 and 820 of the implant structure are opposite ends of the same continuous structure. For applications in which implant structure comprises at least one partial band, such as a partial annuloplasty ring (e.g., as shown in FIGS. 1 and 15), the respective portions of first and second portions 813 and 820 are coupled near respective ends of a sleeve, or themselves define the ring. In either application in which the implant structure comprises a full band or a partial band, the band is surrounded by a braided fabric mesh which facilitates anchoring, suturing, or otherwise coupling the implant structure to the annulus of the valve. For some applications, a compressible structure, e.g., a coil, is disposed between a full or partial band and the braided mesh.

It is to be noted that, for some applications, system 2500 described herein, may be provided independently of second rotatable structure 816. Also, for some applications, the plurality of engaging elements of first portion 813 are shaped so as to define a plurality of window (i.e., and not teeth, as shown). As rotatable structure 2900 is rotated, successive portions of member 30 contact rotatable structure 2900. Geared teeth of pinion 812 matingly engage the windows of portion 813, such that successive portions of member 30 pass between rotatable structure 2900 and a second rotatable structure 816.

Reference is again made to FIGS. 15 and 26. For some applications, flexible members 1130 and 1132 comprise bands each having respective first ends 1131 and 1133, which each define a respective portion 813 (only one portion 813 is shown in FIG. 26 for clarity of illustration). That is, a first portion 813 is disposed with respect to rotatable structure, as shown in FIG. 26, while a second portion 813 is disposed opposite the first portion 813 (i.e., first portion 813 is disposed at 6 o'clock with respect to rotatable structure 2900, while a second portion 813 is disposed at 12 o'clock with respect to structure 2900). As described hereinabove, the second ends of members 1130 and 1132 are coupled to portions 21 and 23, respectively, of structure 1122. Rotation of rotatable structure 2900, i.e., pinion 812, in a first direction thereof causes portions 813 to advance with respect to rotatable structure 2900 in a opposite linear directions with respect to each other such that successive portions of the respective first and second portions 813 contact structure 2900. That is, rotation of structure 2900 in a first direction causes first portion 813 to advance to the right of structure 2900 while the second portion 813 advances to the left of structure 2900. Rotating structure 2900 in a second direction opposite the first direction causes first and second portions 813 to advance in reverse directions to those in which they advanced when structure 2900 was advanced in the first direction.

Figure 27A:
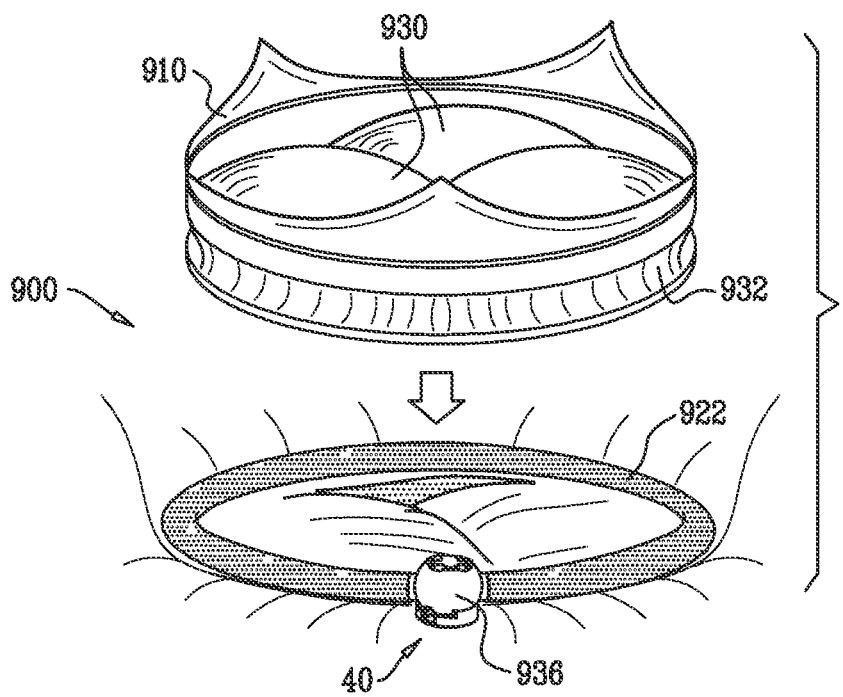
FIGS. 27A-B and 28 are schematic illustrations of a valve prosthesis assembly, in accordance with some applications of the present invention.
Figure 27B:
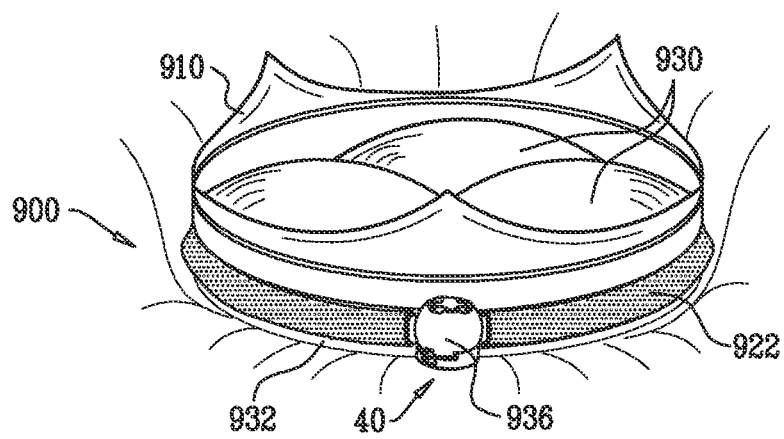
Figure 28:
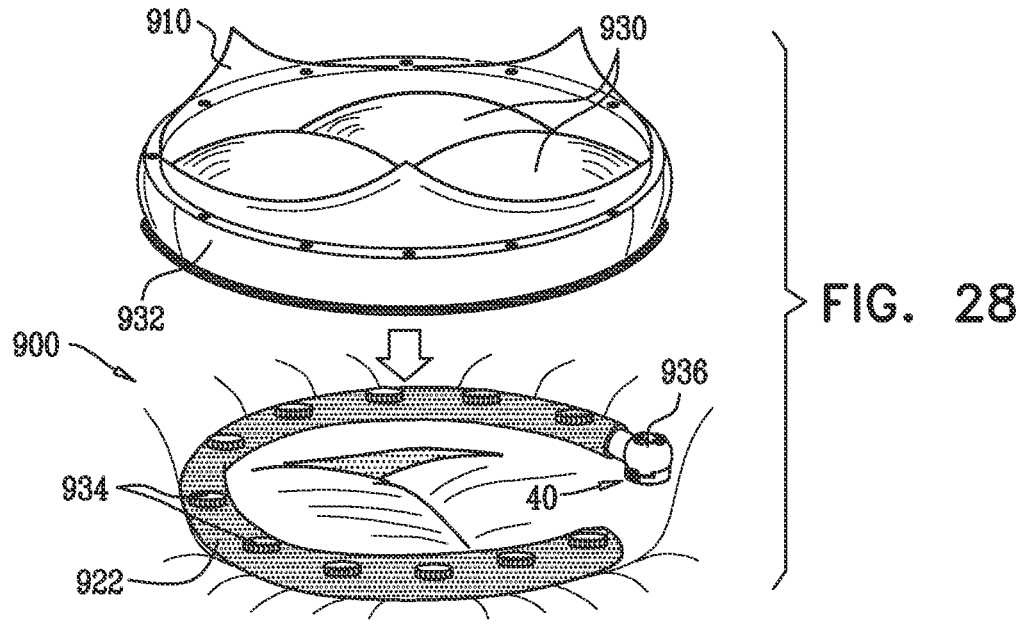

Reference is made to FIGS. 27A-B and 28, which are schematic illustrations of a valve prosthesis assembly 900, in accordance with an application of the present invention. Valve prosthesis assembly 900 comprises a prosthetic heart valve 910 that is couplable to a base ring 922. Prosthetic heart valve 910 is used to replace a native diseased heart valve. Valve 910 comprises a plurality of artificial leaflets 930, which comprise a pliant material. Valve 910 may implement techniques known in the artificial valve art, such as described, for example, in US Patent Application Publication 2007/0255400 to Parravicini et al., US Patent Application Publication 2004/0122514 to Fogarty et al., US Patent Application Publication 2007/0162111 to Fukamachi et al., and/or US Patent Application Publication 2008/0004697 to Lichtenstein et al.

Valve 910 further comprises an annular base 932, to which leaflets 930 are coupled. Annular base is configured to be couplable to base ring 922 during an implantation procedure. For example, as show in FIG. 28, base ring 922 may comprise one or more coupling elements 934, such as clips or magnets, which are configured to be coupled to corresponding coupling elements on a lower surface of annular base 932 (not visible in the figures). Alternatively or additionally, annular base 932 may be configured to be placed within the opening defined by base ring 922, as shown in FIG. 27A. To hold the annular base coupled to the base ring, the base ring is tightened around the annular base, as shown in FIG. 27B, typically using one or more of the techniques described hereinabove for contracting implant structures.

Base ring 922 implements one or more of the techniques of annuloplasty ring 22 described hereinabove. In particular, base ring 922 may be coupled to the annulus of the native diseased valve using the anchoring techniques described hereinabove. In addition, base ring 922 typically comprises a rotatable structure 936, such as a spool, which is typically implemented using techniques described herein. The rotatable structure is arranged such that rotation thereof contracts base ring 922, typically using techniques described herein. Such tightening may serve to couple base ring 922 to annular base 932, as shown in FIG. 27B. Alternatively or additionally, such tightening sets the desired dimensions of the base ring, in order to align the coupling elements of the base ring with those of valve 910, thereby enabling tight coupling, such as for the applications described with reference to FIG. 28.

For some applications, base ring 922 comprises a partial ring, as shown in FIG. 28, while for other applications, the base ring comprises a full ring, as shown in FIGS. 27A-B.

Valve prosthesis assembly 900 is typically implanted in a minimally invasive transcatheter procedure. The procedure begins with the introduction and implantation of base ring 922 into the heart, such as using techniques for implanting annuloplasty ring 22, described hereinabove with reference to FIGS. 9-11 and 17-26. Prosthetic heart valve 910 is subsequently introduced into the heart and coupled to base ring 922, as described above. Valve prosthesis assembly 900 is typically used for replacement of a diseased native mitral valve, aortic valve, tricuspid valve, or pulmonary valve.

Figure 29:
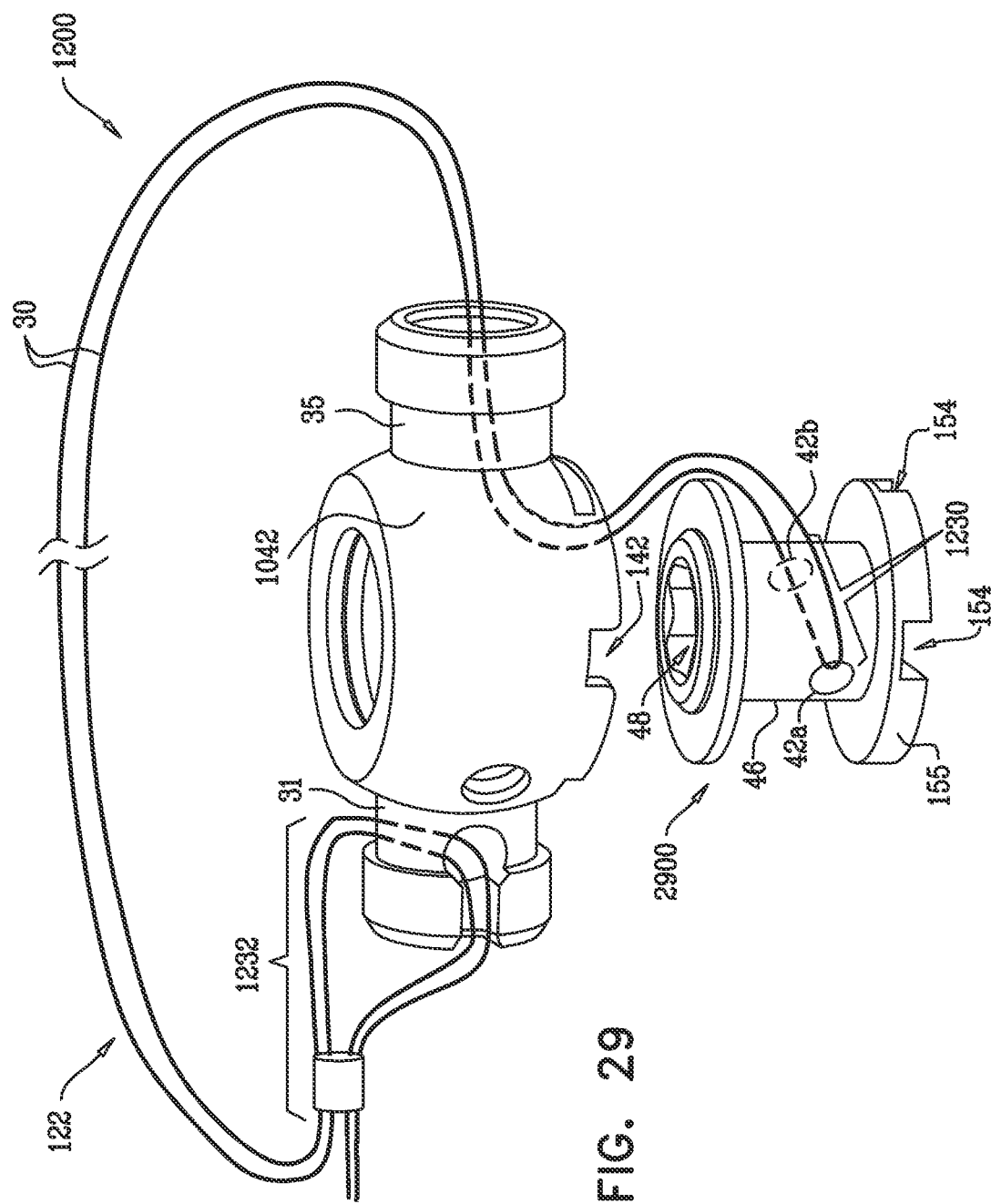
FIG. 29 is a schematic illustration of a contracting member coupled to the annuloplasty structure, in accordance with some applications of the present invention.

FIG. 29 shows a system 1200 in which contracting member 30 is coupled to spool 2146 by being looped through spool 2146, in accordance with some applications of the present invention. Spool 2146 is shaped to define one or more holes 42 (e.g., two holes 42*a* and 42*b*, as shown) configured for looping a portion of contracting member 30 therethrough, as described hereinbelow. In such an application:

(a) a middle portion, which defines a first end portion 1230, of contracting member 30 is coupled to spool 2146 by being looped through one or more holes 42, (b) first and second portions that extend (1) through coupling member 35 of housing 1042, from the first end portion looped through spool 2146 (2) through coupling member 31 of housing 1042, and (3) toward a second end 23 of structure 22, and (c) first and second free ends (and respective portions of contracting member 30) are coupled to second end 23 of structure 122 and define a second end portion 1232 of contracting member 30.

Reference is now made to FIGS. 5 and 29. It is to be noted that contracting member 30 of structure 122, for some applications, is disposed with respect to structure 122 in a manner as shown in FIG. 29.

Reference is now made to FIGS. 1 and 29. It is to be noted that contracting member 30 of annuloplasty structure 22, for some applications, is disposed with respect to annuloplasty structure 22 in a manner as shown in FIG. 29, with the exception that second end portion 1232 is coupled to second end 23 of structure 22 by being coupled to (1) a portion of the compressible element of body portion 24, or (2) to a portion of suture fastener 37. That is second end portion 1232 is not coupled spool 46 or to a portion of the housing surrounding spool 46.

Figure 30A:
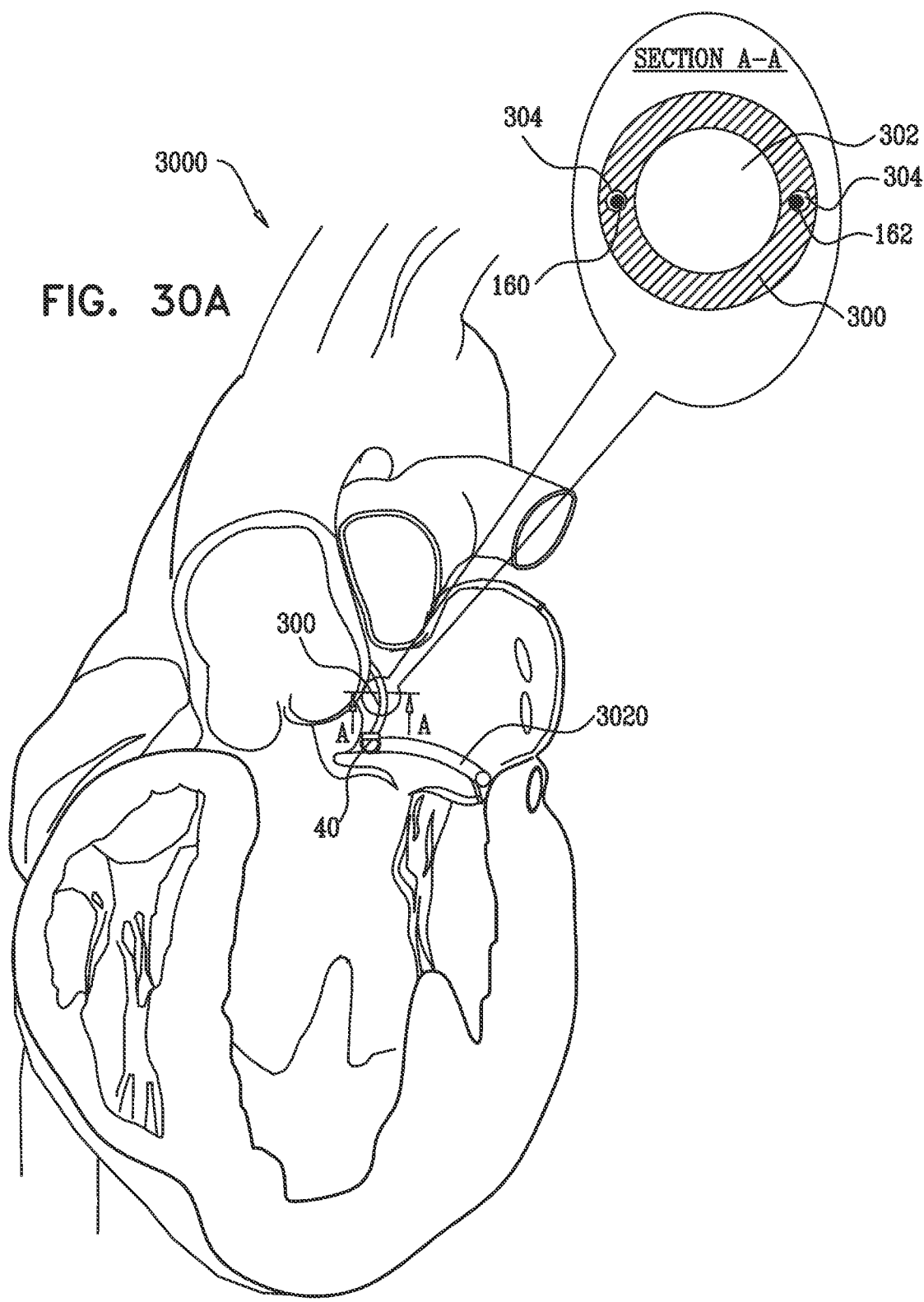
FIGS. 30A-B show a multilumen guide tube coupled at a distal end thereof to the adjusting mechanism, in accordance with some applications of the present invention.
Figure 30B:
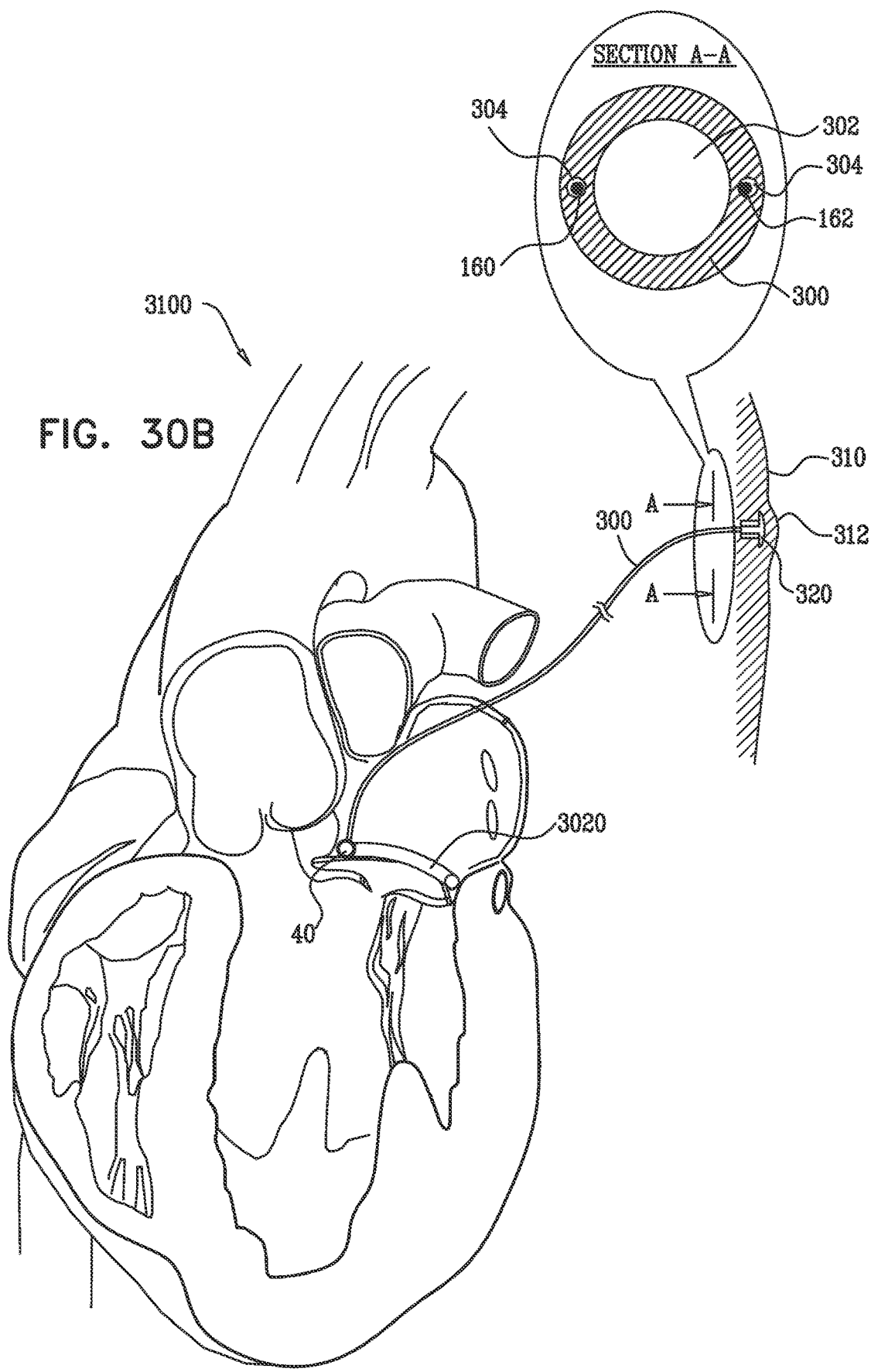

FIGS. 30A-B show a multilumen guide tube 300 coupled at a distal end thereof to adjusting mechanism 40 coupled to an annuloplasty structure 3020, in accordance with some applications of the present invention. Annuloplasty structure comprises any annuloplasty structure as described hereinabove, with specific reference to FIGS. 1-3, 5, 13, and 15. For some applications, the housing of adjusting mechanism 40 is coupled to one or more guide wires (e.g., two guide wires 160 and 162, as shown). It is to be noted that tube 300 may be directly coupled to adjusting mechanism 40, independently of guide wires. Following the implantation of the annuloplasty structures described herein, guide tube 300 is advanced toward the implantation site along guide wires 160 and 162. As shown in section A-A, guide tube 300 defines a primary lumen 302 and respective secondary lumens 304 which surround guide wires 160 and 162. Guide tube 300 is advanced along guide wires 160 and 162 through an opening 330 in the heart, and ultimately toward adjusting mechanism 40. A distal end of guide tube 300 is coupled to the housing of adjusting mechanism 40, and a proximal end of guide tube 300 is coupled to a portion of subcutaneous tissue of the patient. A port 320 is coupled to a proximal end of guide tube 300 and is implanted subcutaneously beneath skin 310 of the patient.

For some applications, as shown in a system 3000 in FIG. 30A, tube 300 extends from adjusting mechanism 40 at the annulus, through the inter-atrial septum (e.g., through the fossa ovalis), through the right atrium. Tube then extends through the inferior vena cava, and through the femoral vein (not shown for clarity of illustration). In such an application, port 320 comprises a transfemoral port. FIG. 30B shows a system 3100 in which tube 300 exits the heart through opening 330 and toward a vicinity of the ribcage by way of illustration and not limitation. In either application, port 320 projects slightly under skin 310 to create a bump 312 (FIG. 30B).

Reference is made to FIGS. 9-11, 12A-B, 13, 14A-C, 15, 16A-C, and 17-30A-B. It is to be noted that although structure 22 is shown as being implanted along annulus 92, structure 122 (as described hereinabove with reference to FIGS. 5, 6A-B, 7, and 8A-B) and structure 1122 (as described hereinabove with reference to FIG. 15) may be implanted along annulus 92 in a similar manner. Since structure 122 does not comprise suture fasteners 41 and 37, sutures are threaded through braided sheath 26 of structure 122 at respective locations along the "D"-shaped ring. As described hereinabove, structure 122 is placed along annulus 92 such that portions 49 of structure 122 are disposed between the trigones of the heart.

For applications in which structure 122 is transcatheterally advanced toward annulus 92, structure 122 may be folded, or otherwise collapsed, such that it fits within the lumen of the advancement catheter.

Reference is again made to FIGS. 9-11, 12A-B, 13, 14A-C, 15, 16A-C, and 17-30A-B. It is to be noted that for applications in which structures 22 and 122 are implanted during an open-heart or minimally-invasive procedure, an incision is made in the heart, and a plurality of sutures are sutured along the annulus are used to facilitate advancement of the annuloplasty structure toward the annulus. Prior to advancement of the annuloplasty structure, portions of the plurality of sutures are threaded through respective portions of the annuloplasty structure. A tool which delivers and facilitates contraction of the annuloplasty structure is coupled to the annuloplasty structure and advances the annuloplasty structure toward the annulus. Once the annuloplasty structure is positioned along the annulus and anchored thereto, the incision is closed around the tool using a purse string stitch. The subject is removed from the cardiopulmonary bypass pump and the heart is allowed to resume its normal function. While the heart is beating, the annuloplasty structure is then contracted, as described hereinabove, and responsively, the annulus is contracted.

Reference is yet again made to FIGS. 9-11, 12A-B, 13, 14A-C, 15, 16A-C, and 17-30A-B. It is to be noted that the annuloplasty structure may be advanced toward the annulus using any suitable delivery tool. Following the positioning of the annuloplasty structure along the annulus, the delivery tool is disengaged from the annuloplasty structure. Then, tools 70 or 2022 may be advanced toward housings 44, 144, or 1042 and engage spools 46, 246, or 2146. In some applications of the present invention, tools 70 or 2022 are advanced toward the annuloplasty structure along a suture coupled to the annuloplasty structure at one end and accessible outside the body of the subject and another end.

It is to be noted that for applications in which structures 22, 122, and 1122, and device 1260 are implanted during an open-heart or minimally-invasive procedure, structures 22, 122, and 1122 and device 1260 may be provided independently or in combination with sutures 130.

Reference is now made to FIGS. 1-30A-B. It is to be noted that the contraction of structures 22, 122, and 1122 and device 1260 described herein is reversible. That is, rotating spool 46 in a rotational direction that opposes the rotational direction used to contract the annuloplasty structure, unwinds a portion of flexible contracting member 30 from around spools 46 or 2146. Unwinding the portion of flexible contracting member 30 from around spool 46 or 2146 thus feeds the portion of flexible contracting member 30 back into the lumen of body portion 24 of structures 22, 122, and 122 and device 1260, thereby slackening the remaining portion of flexible contracting member 30 that is disposed within the lumen of body portion 24. Responsively, the annuloplasty structure gradually relaxes (i.e., with respect to its contracted state prior to the unwinding) as the compressible element of body portion 24 gradually expands.

Reference is again made to FIGS. 1-30A-B. Typically, flexible member 30 comprises a rope or cable that is constructed by coupling (e.g., twisting, braiding, or otherwise coupling) a plurality of strands of metal, polymer, or fabric. This coupling of the strands enables member 30 to conform to the external surface of the spool while not being structurally deformed by the winding of member 30 around the spool. The annuloplasty structures described herein are flexible. That is, when in a contracted state of the structures described herein, contracting member 30 does not have a tendency to expand radially or annularly. Additionally, the braided mesh surrounding the compressible elements of body portion 24 of the annuloplasty devices described herein keeps the entire device from expanding once the device has been contracted. The mesh provides a controlled regulation of the tendency to expand of the compressible elements of the body portion of the annuloplasty devices.

Reference is again made to FIGS. 1-30A-B. It is to be noted that structures 22, 122, and 1122 and device 1260 may be stapled to the annulus using techniques known in the art.

Reference is yet again made to FIGS. 1-30A-B. It is to be noted that following initial contraction of annuloplasty structures 22, 122, and 1122 and device 1260, structures 22, 122, and 1122 and device 1260 may be further contracted or relaxed at a later state following the initial implantation thereof. Using real-time monitoring, tactile feedback and optionally in combination with fluoroscopic imaging, tools 70, 170, and 2022 used to contract or relax annuloplasty structures 22, 122, and 1122 and device 1260 may be reintroduced within the heart and engage spools 46, 246, or 2146.

Reference is yet again made to FIGS. 1-30A-B. It is to be noted that flexible contracting member 30 may be disposed outside the lumen defined by structures 22, 122, and 1122, and device 1260. For example, flexible contracting member 30 may be disposed alongside an outer wall of structures 22, 122, and 1122 and device 1260. In such applications of the present invention, structures 22, 122, and 1122 and device 1260 may not be shaped to define tubular structures having respective lumens thereof, but rather be shaped as bands or ribbons which are not shaped to define a lumen.

It is to be noted that systems 20, 120, 1140, 2020, 2400, 2450, 2500, and assembly 900 for repairing a dilated annulus of the subject may be used to treat a valve of the subject, e.g., the tricuspid valve. It is to be still further noted that systems described herein for treatment of valves may be used to treat other annular muscles within the body of the patient. For example, the systems described herein may be used in order to treat a sphincter muscle within a stomach of the subject.

For some applications, techniques described herein are practiced in combination with techniques described in one or more of the references cited in the Background section and Cross-references section of the present patent application.

Additionally, the scope of the present invention includes applications described in one or more of the following:

PCT Publication WO 06/097931 to Gross et al., entitled "Mitral Valve treatment techniques," filed Mar. 15, 2006;

U.S. Provisional Patent Application 60/873,075 to Gross et al., entitled

"Mitral valve closure techniques," filed Dec. 5, 2006;

U.S. Provisional Patent Application 60/902,146 to Gross et al., entitled

"Mitral valve closure techniques," filed on Feb. 16, 2007;

U.S. Provisional Patent Application 61/001,013 to Gross et al., entitled "Segmented ring placement," filed Oct. 29, 2007;

PCT Patent Application PCT/IL07/001503 to Gross et al., entitled "Segmented ring placement," filed on Dec. 5, 2007, which published as WO 08/068756;

U.S. patent application Ser. No. 11/950,930 to Gross et al., entitled "Segmented ring placement," filed on Dec. 5, 2007, which published as US Patent Application Publication 2008/0262609 and which issued as U.S. Pat. No. 8,926,695;

U.S. Provisional Patent Application 61/132,295 to Gross et al., entitled "Annuloplasty devices and methods of delivery therefor," filed on Jun. 16, 2008;

U.S. patent application Ser. No. 12/341,960 to Cabiri, entitled "Adjustable partial annuloplasty ring and mechanism therefor," filed on Dec. 22, 2008, which issued as U.S. Pat. No. 8,241,351;

U.S. Provisional Patent Application 61/207,908 to Miller et al., entitled

"Actively-engageable movement-restriction mechanism for use with an annuloplasty structure," filed on Feb. 17, 2009;

U.S. patent application Ser. No. 12/435,291 to Maisano et al., entitled "Adjustable repair chords and spool mechanism therefor," filed on May 4, 2009, which issued as U.S. Pat. No. 8,147,542;

U.S. patent application Ser. No. 12/437,103 to Zipory et al., entitled "Annuloplasty ring with intra-ring anchoring," filed on May 7, 2009, which issued as U.S. Pat. No. 8,715,342;

PCT Patent Application PCT/IL2009/000593 to Gross et al., entitled "Annuloplasty devices and methods of delivery therefor," filed on Jun. 15, 2009, which published as WO 10/004546;

U.S. patent application Ser. No. 12/548,991 to Maisano et al., entitled "Implantation of repair chords in the heart," filed on Aug. 27, 2009, which issued as U.S. Pat. No. 8,808,368;

U.S. Provisional Patent Application 61/283,445 to Sheps et al., entitled "Delivery tool for rotation of spool and adjustment of annuloplasty device," filed Dec. 2, 2009; and/or U.S. Provisional Patent Application 61/265,936 to Miller et al., entitled "Delivery tool for implantation of spool assembly coupled to a helical anchor," filed Dec. 2, 2009.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, for use at a valve of a heart of a subject, the apparatus comprising an annuloplasty implant that comprises:
a flexible member;
a plurality of helical anchors, configured to anchor the flexible member at least partway around the valve by each of the helical anchors being screwed into tissue of the heart; and
non-compressible portions,
wherein:
each of the non-compressible portions comprises a helical coil having a plurality of turns, and at rest has a helix pitch that contacts each turn of the coil with an adjacent turn of the coil,
the flexible member extends through the non-compressible portions, and
the implant is configured such that applying tension to the flexible member from one end thereof contracts the implant, thereby drawing the anchors closer to each other, the helical coil of each of the non-compressible portions inhibiting contraction of the implant at the non-compressible portion.

2. The apparatus according to claim 1, wherein each of the non-compressible portions is flexible.

3. The apparatus according to claim 1, wherein the non-compressible portions include a first non-compressible portion and a second non-compressible portion, and a combined length of the first non-compressible portion and the second non-compressible portion is 10-50 mm.

4. The apparatus according to claim 1, further comprising an anchor advancement tube, configured to screw each of the anchors into the tissue.

5. The apparatus according to claim 1, further comprising a locking mechanism having:
an unlocked state in which the locking mechanism is configured to facilitate the contraction of the implant by facilitating application of the tension to the flexible member, and
a locked state in which the locking mechanism is configured to maintain the contraction of the implant by maintaining the tension on the flexible member.

6. The apparatus according to claim 5, further comprising an elongate tool, configured to maintain the locking mechanism in the unlocked state during contraction of the implant.

7. The apparatus according to claim 6, wherein:
the locking mechanism comprises a compressible element that is biased to put the locking mechanism into the locked state,
the elongate tool maintains the locking mechanism in the unlocked state by maintaining the compressible element compressed, and
the apparatus is configured such that removal of the elongate tool from the locking mechanism allows the compressible element to relax, thereby putting the locking mechanism into the locked state.

8. An annuloplasty implant that comprises:
a flexible member;
a plurality of anchors, configured to anchor the flexible member at least partway around the valve by each of the plurality of anchors being inserted into tissue of the heart; and
non-compressible portions,
wherein:
each of the non-compressible portions comprises a helical coil having a plurality of turns, and at rest has a helix pitch that contacts each turn of the coil with an adjacent turn of the coil,
the flexible member extends through the non-compressible portions, and
the implant is configured such that applying tension to the flexible member from one end thereof contracts the implant, thereby drawing the anchors closer to each other, the helical coil of each of the non-compressible portions inhibiting contraction of the implant at the non-compressible portion.

9. The annuloplasty implant according to claim 8, wherein each of the non-compressible portions is flexible.

10. The annuloplasty implant according to claim 8, wherein the non-compressible portions include a first non-compressible portion and a second non-compressible portion, and a combined length of the first non-compressible portion and the second non-compressible portion is 10-50 mm.

11. The annuloplasty implant according to claim 8, wherein the anchors are helical and configured to be screwed into the tissue.

12. The annuloplasty implant according to claim 8, further comprising a locking mechanism having:
an unlocked state in which the locking mechanism is configured to facilitate the contraction of the implant by facilitating application of the tension to the flexible member, and
a locked state in which the locking mechanism is configured to maintain the contraction of the implant by maintaining the tension on the flexible member.

13. The annuloplasty implant according to claim 12, further comprising an elongate tool, configured to maintain the locking mechanism in the unlocked state during contraction of the implant.

14. The annuloplasty implant according to claim 13, wherein:
the locking mechanism comprises a compressible element that is biased to put the locking mechanism into the locked state, the elongate tool maintains the locking mechanism in the unlocked state by maintaining the compressible element compressed, and the annuloplasty implant is configured such that removal of the elongate tool from the locking mechanism allows the compressible element to relax, thereby putting the locking mechanism into the locked state.

15. A system, for use at a valve of a heart of a subject, the system comprising:

an annuloplasty implant that comprises:
  a flexible member;
  a plurality of helical anchors, configured to anchor the flexible member at least partway around the valve by each of the helical anchors being screwed into tissue of the heart; and
  non-compressible portions comprising a helical coil having a plurality of turns, wherein at rest each turn of the coil contacts an adjacent turn of the coil, and wherein the flexible member extends through the non-compressible portions;
an anchor advancement tube, configured to screw each of the anchors into the tissue; and
a locking mechanism having an unlocked state in which the locking mechanism is configured to facilitate the contraction of the implant by application of the tension to the flexible member and a locked state in which the locking mechanism is configured to maintain the contraction of the implant by maintaining the tension on the flexible member;

wherein the implant is configured such that applying tension to the flexible member from one end thereof contracts the implant, thereby drawing the anchors closer to each other, the helical coil of each of the non-compressible portions inhibiting contraction of the implant at the non-compressible portion.

16. The system according to claim 15, wherein each of the non-compressible portions is flexible.

17. The system according to claim 15, wherein the non-compressible portions include a first non-compressible portion and a second non-compressible portion, and a combined length of the first non-compressible portion and the second non-compressible portion is 10-50 mm.

18. The system according to claim 15, further comprising an elongate tool, configured to maintain the locking mechanism in the unlocked state during contraction of the implant.

19. The system according to claim 15, wherein:

the locking mechanism comprises a compressible element that is biased to put the locking mechanism into the locked state, the elongate tool maintains the locking mechanism in the unlocked state by maintaining the compressible element compressed, and the system is configured such that removal of the elongate tool from the locking mechanism allows the compressible element to relax, thereby putting the locking mechanism into the locked state.

\* \* \* \* \*